(12) United States Patent
Kaltenboeck et al.

(10) Patent No.: US 10,293,044 B2
(45) Date of Patent: May 21, 2019

(54) PARTICULATE FORMULATIONS FOR IMPROVING FEED CONVERSION RATE IN A SUBJECT

(71) Applicant: Auburn University, Auburn, AL (US)

(72) Inventors: Bernhard Kaltenboeck, Auburn, AL (US); Ram B. Gupta, Auburn, AL (US); Erfan U. Chowdhury, Auburn, AL (US); Courtney A. Ober, Carlisle, PA (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 15/332,308

(22) Filed: Oct. 24, 2016

(65) Prior Publication Data

US 2017/0072051 A1    Mar. 16, 2017

Related U.S. Application Data

(63) Continuation-in-part of application No. 14/674,711, filed on Mar. 31, 2015, now abandoned.

(60) Provisional application No. 61/986,148, filed on Apr. 30, 2014, provisional application No. 61/981,328, filed on Apr. 18, 2014.

(51) Int. Cl.
| | |
|---|---|
| *A61K 9/16* | (2006.01) |
| *A61K 31/47* | (2006.01) |
| *A61K 47/10* | (2017.01) |
| *C12N 7/00* | (2006.01) |
| *A61K 39/12* | (2006.01) |
| *A61K 39/118* | (2006.01) |
| *A61K 39/39* | (2006.01) |
| *A61K 31/472* | (2006.01) |
| *A61K 9/00* | (2006.01) |
| *A61K 39/00* | (2006.01) |

(52) U.S. Cl.
CPC ............ *A61K 39/39* (2013.01); *A61K 9/0043* (2013.01); *A61K 9/1641* (2013.01); *A61K 9/1647* (2013.01); *A61K 31/47* (2013.01); *A61K 31/472* (2013.01); *A61K 39/118* (2013.01); *A61K 39/12* (2013.01); *A61K 47/10* (2013.01); *C12N 7/00* (2013.01); *A61K 2039/552* (2013.01); *A61K 2039/55511* (2013.01); *A61K 2039/55555* (2013.01); *A61K 2039/57* (2013.01); *A61K 2039/572* (2013.01); *C12N 2720/10034* (2013.01); *C12N 2740/10034* (2013.01)

(58) Field of Classification Search
None
See application file for complete search history.

(56) References Cited

U.S. PATENT DOCUMENTS

| | | |
|---|---|---|
| 5,443,458 A | 8/1995 | Eury |
| 5,670,161 A | 9/1997 | Healy et al. |
| 5,766,710 A | 6/1998 | Turnlund et al. |
| 5,788,979 A | 8/1998 | Alt et al. |
| 5,980,551 A | 11/1999 | Summers et al. |
| 6,372,223 B1 | 4/2002 | Kistner et al. |
| 6,527,801 B1 | 3/2003 | Dutta |
| 6,699,272 B2 | 3/2004 | Slepian et al. |
| 6,709,452 B1 | 3/2004 | Valimaa et al. |
| 6,830,747 B2 | 12/2004 | Lang et al. |
| 7,094,260 B2 | 8/2006 | Jing et al. |
| 7,128,755 B2 | 10/2006 | Su et al. |
| 7,252,937 B2 | 8/2007 | Kaltenboeck |
| 7,390,333 B2 | 6/2008 | Dutta |
| 7,470,283 B2 | 12/2008 | Dutta |
| 8,658,603 B2 | 2/2014 | Holoshitz |
| 8,669,355 B2 | 3/2014 | Poobalane et al. |
| 9,056,095 B2 | 6/2015 | Nishio et al. |
| 2002/0009466 A1 | 1/2002 | Brayden |
| 2002/0019661 A1 | 2/2002 | Datta et al. |
| 2002/0082610 A1 | 6/2002 | Cioanta et al. |
| 2002/0143388 A1 | 10/2002 | Datta et al. |
| 2002/0183830 A1 | 12/2002 | Su et al. |
| 2003/0027940 A1 | 2/2003 | Lang et al. |
| 2003/0045924 A1 | 3/2003 | Datta et al. |
| 2003/0097173 A1 | 5/2003 | Dutta |
| 2003/0105245 A1 | 6/2003 | Amsden |
| 2003/0105518 A1 | 6/2003 | Dutta |

(Continued)

FOREIGN PATENT DOCUMENTS

| | | |
|---|---|---|
| CN | 101601860 | 12/2009 |
| EP | 2402032 | 1/2012 |

(Continued)

OTHER PUBLICATIONS

Bergmann et al., "Th1 or Th2: How an Appropriate T Helper Response can be Made", Bulletin of Mathematical Biology, 63:405-430, 2001.

(Continued)

*Primary Examiner* — Nicole Kinsey White
(74) *Attorney, Agent, or Firm* — Andrus Intellectual Property Law, LLP

(57) ABSTRACT

Disclosed are compositions, kits, and methods for improving feed conversion rate in an animal in need thereof. The methods typically comprise administering orally to the animal a composition comprising biodegradable particles, the biodegradable particles comprising a polymer or a copolymer comprising polylactide (PLA) and having an effective average diameter of 0.5-5 μm. In the methods, the animal is administered a dose of the biodegradable particles that is effective for improving feed conversion rate in the animal in comparison to an animal that is not administered the composition.

20 Claims, 35 Drawing Sheets

(56) References Cited

U.S. PATENT DOCUMENTS

| | | |
|---|---|---|
| 2003/0109647 A1 | 6/2003 | Lang et al. |
| 2003/0118692 A1 | 6/2003 | Wang et al. |
| 2003/0144730 A1 | 7/2003 | Datta et al. |
| 2003/0153971 A1 | 8/2003 | Chandrasekaran |
| 2003/0153972 A1 | 8/2003 | Helmus |
| 2004/0230316 A1 | 11/2004 | Cioanta et al. |
| 2004/0260386 A1 | 12/2004 | Shalaby |
| 2005/0010280 A1 | 1/2005 | Jing et al. |
| 2005/0013869 A1* | 1/2005 | Chaw .............. A61K 9/1647 424/501 |
| 2005/0019404 A1 | 1/2005 | Sung et al. |
| 2005/0169968 A1 | 8/2005 | Elmaleh et al. |
| 2005/0177246 A1 | 8/2005 | Datta et al. |
| 2005/0232971 A1 | 10/2005 | Hossainy et al. |
| 2005/0267565 A1 | 12/2005 | Dave et al. |
| 2005/0278015 A1 | 12/2005 | Dave et al. |
| 2005/0283224 A1 | 12/2005 | King |
| 2006/0002979 A1 | 1/2006 | Ashammakhi et al. |
| 2006/0009839 A1 | 1/2006 | Tan |
| 2006/0018948 A1 | 1/2006 | Guire et al. |
| 2006/0051394 A1 | 3/2006 | Moore et al. |
| 2006/0147491 A1 | 7/2006 | DeWitt et al. |
| 2006/0193892 A1 | 8/2006 | Furst et al. |
| 2006/0198868 A1 | 9/2006 | DeWitt et al. |
| 2006/0264531 A1 | 11/2006 | Zhao |
| 2006/0286138 A1 | 12/2006 | Malshe et al. |
| 2006/0287710 A1 | 12/2006 | Lendlein et al. |
| 2007/0005130 A1 | 1/2007 | Glauser et al. |
| 2007/0014831 A1 | 1/2007 | Sung et al. |
| 2007/0026076 A1 | 2/2007 | Wu et al. |
| 2007/0043433 A1 | 2/2007 | Chandrasekaran |
| 2007/0043434 A1 | 2/2007 | Meerkin et al. |
| 2007/0050018 A1 | 3/2007 | Wainwright |
| 2007/0106371 A1 | 3/2007 | Datta et al. |
| 2007/0123973 A1 | 3/2007 | Roth et al. |
| 2007/0129790 A1 | 6/2007 | Peng |
| 2007/0129793 A1 | 6/2007 | Su et al. |
| 2007/0141100 A1 | 6/2007 | Sung et al. |
| 2007/0184068 A1* | 8/2007 | Renner .............. A61K 39/39 424/204.1 |
| 2007/0196423 A1 | 8/2007 | Ruane et al. |
| 2007/0203564 A1 | 8/2007 | Rusk et al. |
| 2007/0219626 A1 | 9/2007 | Rolando et al. |
| 2007/0224234 A1 | 9/2007 | Steckel et al. |
| 2007/0224244 A1 | 9/2007 | Weber et al. |
| 2007/0224247 A1 | 9/2007 | Chudzik et al. |
| 2007/0237803 A1 | 10/2007 | Cheng et al. |
| 2007/0264307 A1 | 11/2007 | Chen et al. |
| 2007/0275033 A9 | 11/2007 | Moore et al. |
| 2007/0281117 A1 | 12/2007 | Kaplan et al. |
| 2007/0287987 A1 | 12/2007 | Katsarava et al. |
| 2007/0288088 A1 | 12/2007 | Bureau et al. |
| 2007/0298066 A1 | 12/2007 | Alferiev et al. |
| 2008/0008735 A1 | 1/2008 | Diener |
| 2008/0051880 A1 | 2/2008 | Gale et al. |
| 2008/0069858 A1 | 3/2008 | Weber |
| 2008/0071357 A1 | 3/2008 | Girton et al. |
| 2008/0091262 A1 | 4/2008 | Gale et al. |
| 2008/0103583 A1 | 5/2008 | Dutta |
| 2008/0119927 A1 | 5/2008 | Lessar |
| 2008/0152690 A1 | 6/2008 | Kohn et al. |
| 2008/0154351 A1 | 6/2008 | Leewood et al. |
| 2008/0220048 A1 | 9/2008 | Chen et al. |
| 2008/0233168 A1 | 9/2008 | Cheng et al. |
| 2008/0233169 A1 | 9/2008 | Chen et al. |
| 2008/0243240 A1 | 10/2008 | Doty et al. |
| 2008/0249633 A1 | 10/2008 | Wu |
| 2009/0004243 A1 | 1/2009 | Pacetti et al. |
| 2009/0011993 A1* | 1/2009 | Murthy .............. A61K 31/70 514/20.1 |
| 2009/0081270 A9 | 3/2009 | Moore et al. |
| 2009/0082853 A1 | 3/2009 | Dutta |
| 2009/0087494 A1* | 4/2009 | Kompella .............. A61K 47/60 424/499 |
| 2009/0105352 A1 | 4/2009 | Bezwada |
| 2009/0110713 A1 | 4/2009 | Lim et al. |
| 2009/0117039 A1 | 5/2009 | Richard |
| 2009/0149568 A1 | 6/2009 | Pacetti |
| 2009/0169634 A1 | 7/2009 | Cheng et al. |
| 2009/0171455 A1 | 7/2009 | Benco et al. |
| 2009/0182404 A1 | 7/2009 | Shokoohi |
| 2009/0182415 A1 | 7/2009 | Wang |
| 2009/0192588 A1 | 7/2009 | Shin et al. |
| 2009/0232863 A1 | 9/2009 | Cheng et al. |
| 2009/0299465 A1 | 12/2009 | Shalaby |
| 2009/0319041 A1 | 12/2009 | Cannas et al. |
| 2012/0009220 A1 | 1/2012 | Li et al. |
| 2012/0189700 A1 | 7/2012 | Aguilar et al. |

FOREIGN PATENT DOCUMENTS

| | | |
|---|---|---|
| WO | 200243705 | 6/2002 |
| WO | 2010033923 | 3/2010 |
| WO | 2010098432 A1 | 9/2010 |
| WO | 2012006359 | 1/2012 |
| WO | 2013049106 | 4/2013 |

OTHER PUBLICATIONS

Bergmann et al., "How Instruction and Feedback Can Select the Appropriate T Helper Response", Bulletin of Mathematical Biology, 64:425-446, 2002.

Chadwick et al., Advanced Drug Delivery Reviews, 2010, 62:394-407.

Chaplin, David, "Overview of the Immune Response", J. Allergy Clin. Immunol. Feb. 2010; 125(2 Suppl 2): S3-23.

Cotter et al., "Dissemination of Chlamydia trachomatis Chronic Genital Tract Infection in Gamma Interferon Gene Knockout Mice", Infection and Immunity, 65:(6)2145-2152, Jun. 1997.

Evans et al., "QS-21 promotes an adjuvant effect allowing for reduced antigen dose during HIV-1 envelope subunit immunization in humans", Vaccine, 2001, 19:2080-2091.

International Preliminary Report on Patentability for PCT/US2015/023567 dated Oct. 18, 2016.

International Search Report for PCT/US2015/023567 dated Jul. 1, 2015.

Katare, Y.K. et al., "Indluence of particle size, antigen load, dose and additional adjuvant on the immune response from antigen loaded PLA microparticles", International Journal of Pharmaceutics, Sep. 14, 2005, 301(1-2):149-160.

Kawaguchi et al., Biomaterials 7:61-66 (1986).

Kenney et al., "Dose Sparing with Intradermal Injection of Influenza Vaccine", The New England Journal of Medicine, 351(22):2295-2301, Nov. 25, 2004.

Krenis et al., Proc. Soc. Exp. Med., 107:748-750 (1961).

Leon-Rodriquez, L. et al., "Biodegradable microparticles covalently linked to surface antigens of the scuticociliate parasite P. dicentrarchi promote innate immune responses in vitro", Fish & Shellfish Immunology, Jan. 1, 2013, 34(1):236-243.

Li et al., "Novel Chlamydia pneumoniae vaccine candidates confirmed by Th1-enhanced genetic immunization", Vaccine, 28(6):1598-1605, Feb. 10, 2010.

Lin et al., "Protective effects of oral microencapsulated Mycoplasma hyopneumoniae vaccine prepared by co-spray drying method", J Vet Med Sci. Jan. 2003;65(1):69-74.

Lin et al., "In vivo and in vitro comparisons of spray-drying and solvent- evaporation preparation of microencapsulated Mycoplasma hyopneumoniae for use as an orally administered vaccine for pigs", Am J Vet Res. Aug. 2002;63(8): 1118-23.

Lu et al., "Chlamydia trachomatis Mouse Pneumonitis Lung Infection in IL-18 and IL-12 Knockout Mice: IL-12 Is Dominant over IL-18 for Protective Immunity", Molecular Medicine, 6(7):604-612, 2000.

Morrison et al., "Gene Knockout Mice Establish a Primary Protective Role for Major Histocompatibility Complex Class II-Restricted Responses in Chlamydia trachomatis Genital Tract Infection", Infection and Immunity, 63(12):4661-4668, Dec. 1995.

(56) References Cited

OTHER PUBLICATIONS

Perry et al., "Immunity to Chlamydia trachomatis is mediated by T helper 1 cells through IFN-y-dependent and -independent pathways", Journal of Immunology, 1997, 158:3344-3352.
Rosa et al., Journal of Controlled Release, 2000, 69:283-295.
Rottenberg et al., "Regulation and Role of IFN-gamma in the Innate Resistance to Infection with Chlamydia pneumoniae", The Journal of Immunology, 164:4812-4818, 2000.
Rudt et al., J. Contr. Rel. 22: 263-272 (1992).
Scheifele et al., "Safety and Immunogenicity of a Pentavalent Combination Vaccine (Diphtheria, Tetanus, Acellular Pertussis, Polio and Haemophilus Influenzae Type b Conjugate) When Administered as a Fourth Dose at 15 to 18 Months of Age", Human Vaccines, 1(5)180-186, Nov. 4, 2005.
Silva, J.M. et al., "Immune system targeting by biodegradable nanoparticles for cancer vaccines", Journal of Controlled Release, Mar. 21, 2013, 168(2):179-199.
Spellberg et al., "Type 1/Type 2 Immunity in Infectious Diseases", Clin. Infect. Dis. 2001;32:76-102.
Stemke-Hale et al., "Screening the whole genome of a pathogen in vivo for individual protective antigens", Vaccine, 2005, 23:3016-3025.
Torchinsky et al., "Innate immune recognition of infected apoptotic cells directs TH17 cell differentiation", Nature, Mar. 2009, 485:78.
Truptimayee et al., "Antigen adsorbed surface modified polycaprolactone microspheres stimulates both adaptive and innate immune response in fish", Vaccine, May 12, 2012, 30(35): 5278-5284.
Vuola et al., "Acquired Immunity to Chlamydia pneumoniae Is Dependent on Gamma Interferon in Two Mouse Strains That Initially Differ in This Respect after Primary Challenge", Infection and Immunity, 68(2):960-964, Feb. 2000.
Wang et al., "IFN-gamma knockout mice show Th2-associated delayed-type hypersensitivity and the inflammatory cells fail to localize and control chlamydial infection", European Journal of Immunology, 29:3782-3792, 1999.
Written Opinion for PCT/US2015/023567 dated Jul. 1, 2015.
Dwivedi et al., "PLGA nanoparticle entrapped killed porcine reproductive and respiratory syndrome virus vaccine helps in viral clearance in pigs," Veter. Micro. 166 (2013), 47-58.
Chinese Office Action for CN 201580020400.1 dated Dec. 18, 2018.

* cited by examiner

PARTICULATE FORMULATIONS FOR IMPROVING FEED CONVERSION RATE IN A SUBJECT

CROSS-REFERENCE TO RELATED APPLICATIONS

This application is a continuation-in-part of U.S. application Ser. No. 14/674,711, filed on Mar. 31, 2015, and published as U.S. Publication No. 2015/0297706 on Oct. 22, 2015, and now abandoned, which application claims the benefit under 35 U.S.C. § 119(e) to U.S. Provisional Application No. 61/981,328, filed on Apr. 18, 2014 and to U.S. Provisional Application No. 61/986,148, filed on Apr. 30, 2014, the contents of which are incorporated herein by reference in their entireties.

BACKGROUND

The present invention relates generally to the field of compositions, kits, and methods for inducing an immune response. In particular, the invention relates to particulate vaccine formulations for inducing innate or adaptive immunity against an infection or a disease.

T-helper (Th) lymphocytes may be categorized into two distinct subsets of effector cells based on their functional capabilities and cytokine profiles. Th1 cells produce IFN-γ, TNF-β, and IL-2 and help to activate macrophages and cytotoxic T lymphocytes. In addition, Th1 cells assist other immune cells in the production of those antibody isotypes that promote opsonization. Th2 cells trigger B cells to produce and secrete antibodies. In contrast, Th2 cells are particularly effective at inducing B cells to produce certain antibody isotypes such as IgE and IgA, which neutralize intercellular pathogens and help opsonization, complement, mast cell, and eosinophil activation. Because of these functional differences, Th1 and Th2 exhibit different efficiency in elimination of a selected pathogen. Diseases that can be prevented or treated successfully by Th1 responses include mycobacterial infections such as tuberculosis, leprosy, leishmaniasis, and schistosomiasis, which are intracellular infections, and certain viral diseases. Th2 responses are protective against helminths and some bacteria such as pneumo- and meningococcii.

Th1 and Th2 cells arise from a common precursor cell called Th0. Differentiation of T-helper cells into Th1 and Th2 cells is an important event in determining the outcome of an immune response (i.e., whether a pathogen will persist, whether the host will be protected, and/or whether the host will experience immunopathogenesis). Infectious pathogens may exhibit a predisposition to induce a cell-mediated form of immunity versus a humoral form of immunity. Successful defense against intracellular pathogens tends to be associated with Th1 dominance and resultant cellular cytolytic activity, whereas resistance to extracellular infectious pathogens is most often dominated by Th2 effectors, which lead to the production of high levels of antigen-specific immunoglobulins. Therefore, a better understanding of the factors that contribute to differentiation of Th0 cells into Th1 and Th2 cells will help facilitate preparation of more effective prevention and treatment strategies.

SUMMARY

Disclosed are compositions, kits, and methods for inducing an immune response. The immune response induced by the composition, kits, and methods preferably is a Th1 cell immune response versus a Th2 cell immune response.

The compositions and kits disclosed herein include biodegradable particles having an effective average diameter that is small enough such that the disclosed biodegradable particles are phagocytosed by antigen presenting cells, such as macrophage and dendritic cells, when the biodegradable particles are administered to a subject in need thereof. Typically, the biodegradable particles are effective in stimulating an innate or adaptive immune response. As such, particulate immunogenic compositions and vaccine formulations for inducing an innate or adaptive immune response are disclosed herein.

The biodegradable particles of the compositions and kits disclosed herein may have an effective average diameter of less than about 5.0 µm, 4.0 µm, or 3.0 µm. In some embodiments, the biodegradable particles have an average effective diameter of about 0.5-5.0 µm, 0.5-4.0 µm, or 0.5-3.0 µm.

The disclosed particles of the compositions and formulations are biodegradable and may include polymeric or non-polymeric material. In some embodiments, the biodegradable particles comprise polymeric material formed from carbohydrate monomers. The biodegradable particles may be formed by a process that includes spray-drying a liquid composition to form the biodegradable particles.

The compositions and formulations optionally may include excipients for the biodegradable particles. In some embodiments, the compositions and formulations include a powder excipient. In other embodiments, the compositions and formulations comprise a suspension of the biodegradable particles in an excipient that includes a non-ionic surfactant solution.

The disclosed compositions and formulations comprising the biodegradable particles may be administered to a subject in order to induce an immune response. In some embodiments, the disclosed compositions and formulations are administered to the subject at a dose that delivers the biodegradable particles to the subject in an amount between about $(BW/20)^{3/4}$ µg and $100\times((BW/20)^{3/4})$µg, wherein BW is the body weight of the subject in grams.

The disclosed compositions and formulations comprising the biodegradable particles may include additional agents for modulating an immune response. In some embodiments, the disclosed compositions and formulations comprising the biodegradable particles further comprise an adjuvant. In even further embodiments, the disclosed compositions and formulations comprising the biodegradable particles further comprise an apoptosis inhibitor.

In some embodiments, the disclosed compositions and formulations comprising the biodegradable particles may be administered to a subject in a method for inducing innate immunity in the subject. For example, the compositions and formulations may consist of the biodegradable particles and optionally an adjuvant and/or an apoptosis inhibitor, and the vaccine formulation may not comprise an antigen for inducing adaptive immunity.

In other embodiments, the disclosed compositions and formulations comprising the biodegradable particles may be administered to a subject in a method for inducing adaptive immunity. For example, the compositions and formulations may comprise the biodegradable particles and optionally an adjuvant and/or an apoptosis inhibitor, and the compositions and formulations further may comprise an antigen for inducing adaptive immunity.

In embodiments in which the compositions and formulations comprising the biodegradable particles further comprise an antigen for inducing adaptive immunity, the antigen may be present at a concentration that is relative to the concentration of the biodegradable particles. In some embodiments, the compositions and formulations comprise particles and antigens at a molar ratio of 0.2, 0.5, 1.0, 2.0, or 5.0, and preferably at a molar ratio approaching 1.0. In embodiments in which the antigens are small peptide antigens (e.g., peptide antigens having 10-50 amino acids), the peptide antigen may present in the compositions and formulations at a suitable concentration ratio such as 0.00018 antigen/µg biodegradable particles, 0.0018 fmole antigen/µg biodegradable particles, 0.018 fmole antigen/µg biodegradable particles, 0.18 fmole antigen/µg biodegradable particles, 1.8 fmole antigen/µg biodegradable particles, 18.0 fmole antigen/µg biodegradable particles, and ratios within ranges defined by any pairs of these suitable ratios (e.g., 0.18-1.8 fmole antigen/µg biodegradable particles).

In embodiments in which the compositions and formulations comprising the biodegradable particles further comprise an antigen for inducing adaptive immunity, the vaccine formulations may be administered to the subject at a dose that delivers the antigen to the subject at a suitable dose level. In some embodiments, the compositions and formulations may be administered to the subject at a suitable dose levels such as 0.0009 fmole antigen/g body weight of the subject, 0.009 fmole antigen/g body weight of the subject, 0.09 fmole antigen/g body weight of the subject, 0.9 fmole antigen/g body weight of the subject, and dose levels within ranges defined by any pairs of these suitable dose levels (e.g., 0.09-0.9 fmole antigen/g body weight of the subject). In other embodiments, the compositions and formulations may be administered to the subject at a suitable dose level such as 0.002 pg antigen/g body weight of the subject, 0.02 pg antigen/g body weight of the subject, 0.2 pg antigen/g body weight of the subject, 2.0 pg antigen/g body weight of the subject and dose levels within ranges defined by any pairs of these suitable dose levels (e.g., 0.2-2.0 pg antigen/g body weight of the subject).

Suitable antigens for the compositions and formulations comprising the biodegradable particles may include peptide antigens. For example, suitable antigens may include peptide antigens having an amino acid length of less than about 100, 50, 40, 30, or 20 amino acids. Suitable antigens may include peptide antigens having a molecular weight of less than about 10, 5, 4, 3, or 2 kD.

The methods contemplated herein include methods that consist of administering compositions and formulations consisting essentially of the biodegradable particles. In some embodiments, the methods consist of administering compositions and formulations consisting essentially of a suspension of the biodegradable particles, such as a suspension of the biodegradable particles in a solution of a non-ionic surfactant. In other embodiments, the methods consist of administering compositions and formulations consisting essentially of a suspension of the biodegradable particles, such as a suspension of the biodegradable particles in a solution of a non-ionic surfactant and an adjuvant. In even further embodiments, the methods consist of administering compositions and formulations consisting essentially of a suspension of the biodegradable particles, such as a suspension of the biodegradable particles in a solution of a non-ionic surfactant, an adjuvant, and an apoptosis inhibitor. In even further embodiments, the methods consist of administering compositions and formulations consisting essentially of a suspension of the biodegradable particles, such as a suspension of the biodegradable particles in a solution of a non-ionic surfactant, an adjuvant, an apoptosis inhibitor, and an antigen (e.g., a peptide antigen or a mixture of peptide antigens).

In the disclosed methods, the disclosed compositions and formulations may be administered to a subject in order to stimulate T cell immunity. For example, the disclosed vaccine compositions may be administered to a subject in order to stimulate T cell immunity against infection by a pathogen. In some embodiments, the disclosed compositions and formulations may be administered to a subject in order to stimulate a Th1 cell immune response.

The present inventors have observed when the disclosed compositions and formulations comprising biodegradable particles are administered to a subject, the subject gains weight at higher relative rate than a subject that has not been administered the compositions and formulations. Therefore, the disclosed methods include methods of administering the disclosed compositions and formulations for inducing weight gain in a subject. The disclosed methods also include methods of administering the disclosed compositions and formulations to a subject for increasing feed conversion rate in the subject. The disclosed methods also include methods of administering the disclosed compositions and formulations to a subject for increasing survival rate. Suitable subjects for the methods for inducing weight gain and/or for increasing feed conversion rate may include, but are not limited to, fowl, such as chickens and turkeys, swine, and ruminants, such as cattle, sheep, and goats.

BRIEF DESCRIPTION OF THE DRAWINGS

FIG. 23. Process diagram of the Mini Spray Dryer B-190, B-191 and B-290 models with process parameters. (Reproduced from Cordin et al., 2010).

DETAILED DESCRIPTION

Figure 1:
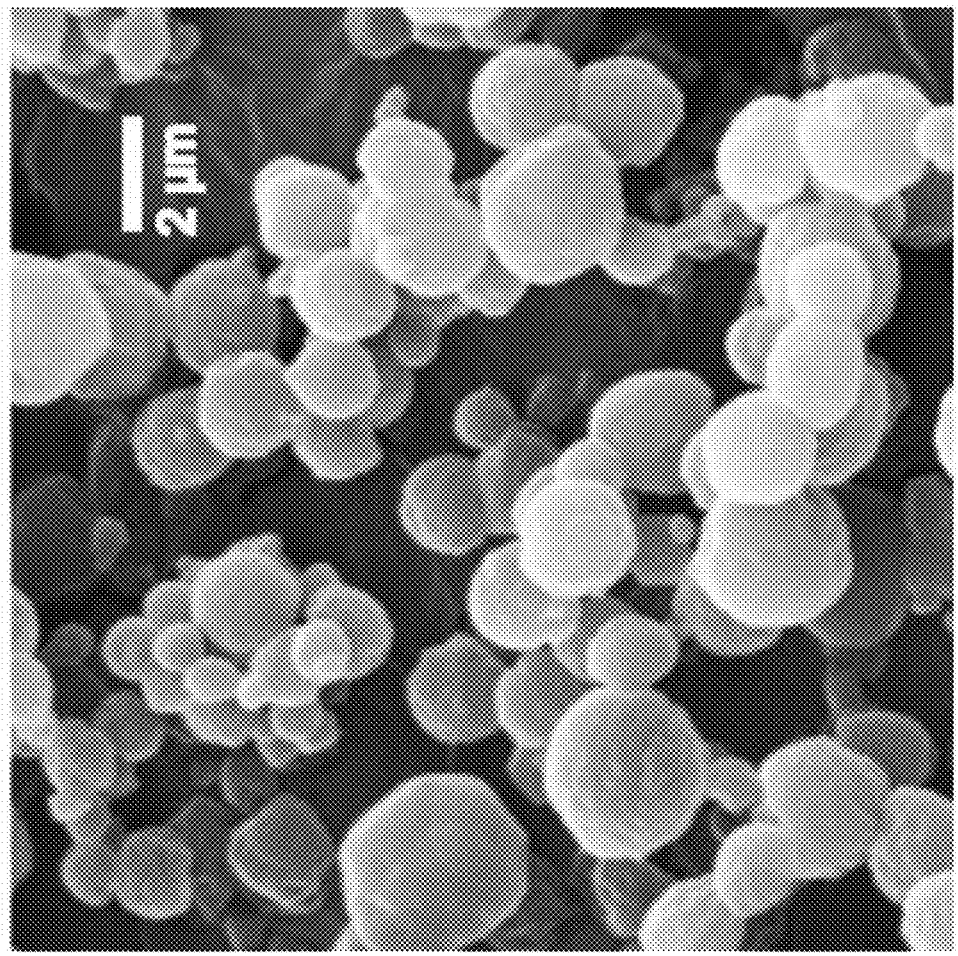
FIG. 1. A. Scanning electron micrograph of spray-dried microparticles composed of PLGA-PEG:Pluronic® L121 block copolymer=3:2. B. Percent survival when challenged day 21 post-administration of immune stimulator. C. Percent survival when challenged day 11 post-administration of immune stimulator. D. Percent survival when challenged day 1 post-administration of immune stimulator.
Figure 1:
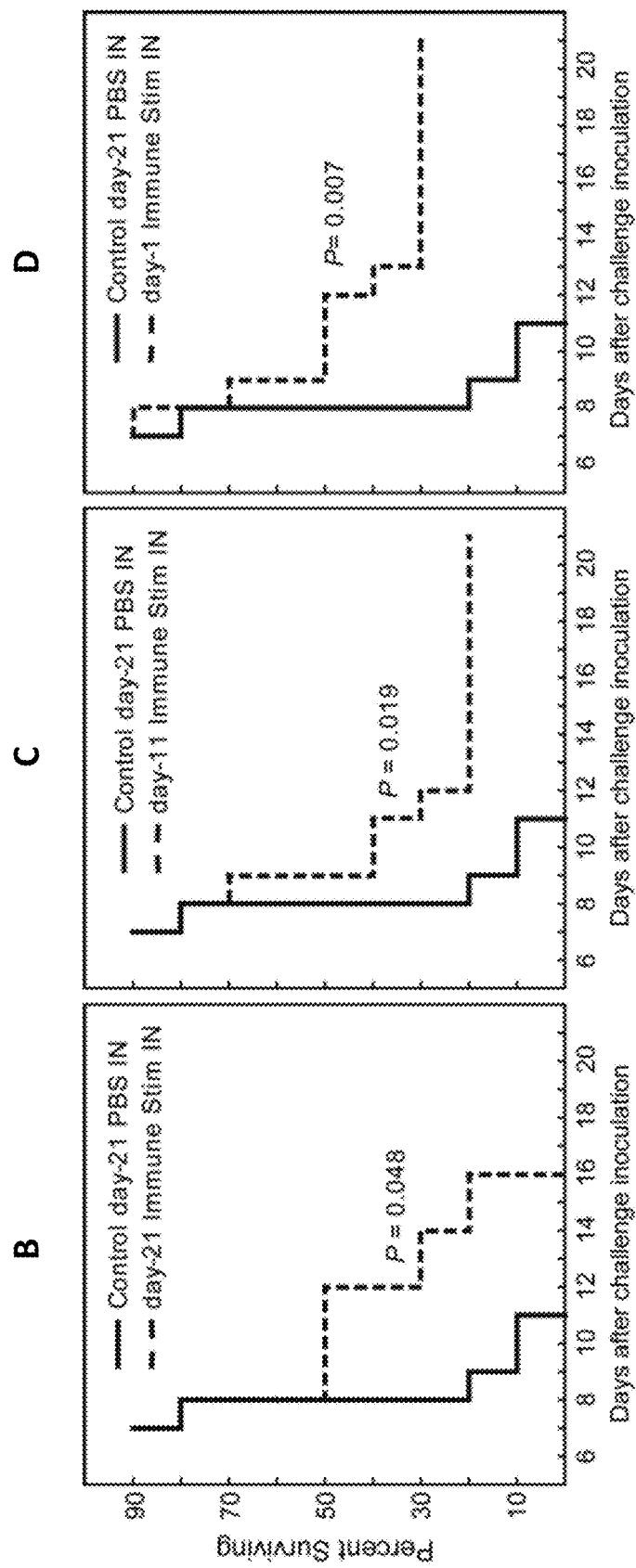

Disclosed herein are compositions, kits, and methods for inducing an immune response against disease which may be described using several definitions as discussed below.

Unless otherwise specified or indicated by context, the terms "a", "an", and "the" mean "one or more." In addition, singular nouns such as "adjuvant," "apoptosis inhibitor," and "antigen" should be interpreted to mean "one or more adjuvants," "one or more apoptosis inhibitors," and "one or more antigens," respectively, unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The terms "subject," "patient," or "host" may be used interchangeably herein and may refer to human or non-human animals. Non-human animals may include, but are not limited to fowl (e.g., chickens and turkeys), cows, pigs, horses, dogs, and cats.

The terms "subject," "patient," or "individual" may be used to a human or non-human animal having or at risk for acquiring infection by a pathogen (e.g. a bacterial, viral, or fungal pathogen) or a disease (e.g., cancer or an autoimmune disease) that is amenable to treatment or protection by a vaccine. For example, individuals who are treated with the compositions disclosed herein may be at risk for infection with a pathogen or may have already been infected with the pathogen. Individuals who are treated with the compositions disclosed herein may be at risk for cancer or may have already acquired cancer. Individuals who are treated with the compositions disclosed herein may be at risk for an autoimmune disease or may have already acquired an autoimmune disease.

Biodegradable Particles.

The disclosed compositions include compositions comprising biodegradable particles. The biodegradable particles typically have an effective average diameter of 0.1-5.0 μm, preferably 0.5-4.0 μm, and more preferably 0.5-3.0 μm. The biodegradable particles may be referred to herein as "microparticles" and/or "nanoparticles."

Preferably, the disclosed particles are phagocytosed by antigen presenting cells, such as macrophage and dendritic cells, when the disclosed particles are administered as an immunogenic composition or vaccine formulation to a subject in need thereof. Preferably, the disclosed particles have an effective average diameter to permit phagocytosis by antigen presenting cells. Particles larger than about 5 microns are unlikely to be phagocytosed by antigen presenting cells and preferably the particles have an effective average diameter of less than about 4 microns or more preferably the particles have an effective average diameter of less than about 3 microns.

The disclosed particles typically are biodegradable as would be understood in the art. The term "biodegradable" describes a material that is capable of being degraded in a physiological environment into smaller basic components.

Preferably, the smaller basic components are innocuous. For example, an biodegradable polymer may be degraded into basic components that include, but are not limited to, water, carbon dioxide, sugars, organic acids (e.g., tricarboxylic or amino acids), and alcohols (e.g., glycerol or polyethylene glycol). Biodegradable materials that may be utilized to prepare the particles contemplated herein may include materials disclosed in U.S. Pat. Nos. 7,470,283; 7,390,333; 7,128,755; 7,094,260; 6,830,747; 6,709,452; 6,699,272; 6,527,801; 5,980,551; 5,788,979; 5,766,710; 5,670,161; and 5,443,458; and U.S. Published Application Nos. 20090319041; 20090299465; 20090232863; 20090192588; 20090182415; 20090182404; 20090171455; 20090149568; 20090117039; 20090110713; 20090105352; 20090082853; 20090081270; 20090004243; 20080249633; 20080243240; 20080233169; 20080233168; 20080220048; 20080154351; 20080152690; 20080119927; 20080103583; 20080091262; 20080071357; 20080069858; 20080051880; 20080008735; 20070298066; 20070288088; 20070287987; 20070281117; 20070275033; 20070264307; 20070237803; 20070224247; 20070224244; 20070224234; 20070219626; 20070203564; 20070196423; 20070141100; 20070129793; 20070129790; 20070123973; 20070106371; 20070050018; 20070043434; 20070043433; 20070014831; 20070005130; 20060287710; 20060286138; 20060264531; 20060198868; 20060193892; 20060147491; 20060051394; 20060018948; 20060009839; 20060002979; 20050283224; 20050278015; 20050267565; 20050232971; 20050177246; 20050169968; 20050019404; 20050010280; 20040260386; 20040230316; 20030153972; 20030153971; 20030144730; 20030118692; 20030109647; 20030105518; 20030105245; 20030097173; 20030045924; 20030027940; 20020183830; 20020143388; 20020082610; and 0020019661; the contents of which are incorporated herein by reference in their entireties. Typically, the biodegradable particles disclosed herein are degraded in vivo at a degradation rate such that the particles lose greater than about 50%, 60%, 70%, 80%, 90%, 95%, or 99% of their initial mass after about 4, 5, 6, 7, or 8 weeks post-administration. The particles may comprise or may be formed from polymeric or non-polymeric biodegradable material. If the particles comprise polymeric material, typically the particles are degraded into biodegradable monomers. If the particles comprise non-polymeric material, typically the particles are degraded into biodegradable components.

Suitable polymers for preparing the biodegradable particles may include, but are not limited to, polymers such as polylactides (PLA), including polylactic acid, for example, polyglycolides (PGA), including polyglycolic acid, and co-polymers of PLA and PGA (i.e., PLGA). Other suitable polymers may include, but are not limited to, polycaprolactone (PCL), poly(dioxanone) (PDO), collagen, renatured collagen, gelatin, renatured gelatin, crosslinked gelatin, and their co-polymers. The polymer of the biodegradable particles is designed to degrade as a result of hydrolysis of polymer chains into biologically acceptable and progressively smaller components such as polylactides, polyglycolides, and their copolymers. These break down eventually into lactic and glycolic acid, enter the Kreb's cycle and are broken down into carbon dioxide and water and excreted.

Suitable non-polymers may include poorly soluble compounds such as compounds shown to function as immunomodulators. One suitable compound is nelfinavir, which has been shown to exhibit an immunopotentiating effect. As such, biodegradable particles that are contemplated herein may include biodegradable particles formed from immunomodulating compounds.

The disclosed biodegradable particles may be prepared by methods known in the art including, but not limited to, spray-drying, precipitation, and grinding. In some embodiments, the biodegradable particles may be formed from a solution or suspension of a biodegradable material optionally in the presence of one or more additional agents such as adjuvants, apoptosis inhibitors, and/or antigens (e.g., by spray-drying the solution or suspension). As such, the biodegradable particles may comprise biodegradable material and optionally may comprise one or more additional agents such as adjuvants, apoptosis inhibitors, and/or antigens.

The disclosed biodegradable particles may be administered in order to induce a response in a subject. In some embodiments, the disclosed methods comprise administering a composition comprising biodegradable particles to induce an immune response in the subject. In other embodiments, the disclosed methods consist of administering a composition consisting of biodegradable particles to induce an immune response in the subject. The induced immune response may include a Th1 cell response. The induced immune response in a subject administered the composition may cause the subject to exhibit higher weight gain or better feed conversion rate than a subject that is not administered the composition. In some embodiments, the disclosed methods comprise administering a composition comprising biodegradable particles to induce weight gain in a subject and/or to improve feed conversion rate in a subject.

The dose of biodegradable particles administered in the disclosed methods may vary based on the weight of a subject. For example, a mouse having a weight of about 20 g may be administered a dose of particles equivalent to about 1-100 µg (or 2-50 µg or 5-20 µg). This dose may be allometrically scaled based on the formula $(BW/20)3/4$=allometric scaling factor, where "BW" equals the body weight of the target animal in grams. Assuming that the target animal is a chicken weight 1600 g, the allometric scaling factor is $(1,600/20)^{3/4}$=26.7. Multiplying the 10 µg microparticle amount used for a 20 g mouse by the scaling factor of 26.7 for a 1600 g chicken results in a microparticle dose of ~270 µg. Similarly, for a human having a weight of 80,000 g, the allometric scaling factor is $(80000/20)^{3/4}$=~503. Multiplying the 10 µg microparticle amount used for a 20 g mouse by the scaling factor of 503 for a 80000 g human results in a microparticle dose of ~5030 µg.

Adjuvants.

The compositions disclosed herein optionally include an adjuvant. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants which may be utilized in the disclosed compositions include but are not limited to, co-polymer adjuvants (e.g., Pluronic® L121 block copolymer brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., $AlPO_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

Apoptosis Inhibitors.

The compositions disclosed herein optionally may include an apoptosis inhibitor. An "apoptosis inhibitor" refers to a small molecule that inhibits a cell's initiation of or progression through the apoptosis process. Apoptosis inhibitors may include small inhibitors of pan-caspase (e.g., Q-VD-OPH and emriscan) or inhibitors of other enzymes involved in the apoptotic pathways, as well as inhibitors of c-Myc, Bax, p53, tBid, and BCL which mediate apoptosis.

Antigens and Dose.

The compositions disclosed herein optionally may include an antigen, a panel of antigens, or a plurality of antigens. In embodiments of the disclosed compositions comprising biodegradable particles and antigens, the particles and antigens may be present in the compositions at a suitable ratio. For example, the particles and antigens may be present in a molar ratio of about 0.2, 0.5, 1.0, 2.0, or 5.0, and preferably at a ratio approaching 1.0.

The disclosed composition may comprise a "panel" or "plurality of antigens." A "panel" or "plurality" or antigens as used herein means "more than one" and may mean more than 1, 2, 3, 4, 5, 10, 25, 50, or 100 antigens. A panel or plurality of antigens may include a set of different, overlapping polypeptides (e.g., polypeptides of about 10-20 amino acids that overlap by about 5-10 amino acids) where the overlapping polypeptides correspond to a full-length polypeptide associated with a disease. A panel of polynucleotides may encode different or unique amino acid sequences of a selected polypeptide. The encoded different or unique amino acid sequences may overlap. For example, a panel of overlapping polypeptides may correspond to the full-length sequence of a protein where a first polypeptide of a panel includes amino acids 1-20 of the protein, the second polypeptide of the panel includes amino acids 11-30 of the protein, the third polypeptide of the panel includes amino acids 21-40 of the protein, the fourth polypeptide of the panel includes amino acids 31-50 of the protein, such the overlapping polypeptides of the panel encompass all of the amino acid sequence of the protein.

The composition, kits, and methods contain or utilize a protein, polypeptide, peptide, or panel thereof as an antigen. In some embodiments, the dosage of antigen contained or utilized in the presently disclosed compositions, kits, and methods is substantially lower than that dosage conventionally used in the field (e.g., by at least an order of magnitude (10×)). The compositions, kits, and methods may be utilized to induce a cell-mediated response (e.g., a T-helper cell response) and/or a humoral response against a disease. In some embodiments, the compositions, kits, and methods may be utilized to induce preferentially a Th1 response versus other types of immune responses (e.g., a Th2 response).

In some embodiments, the disclosed compositions, kits, and methods include or utilize a relatively low amount of antigen compared to vaccines and methods of the art. As contemplated herein, suitable doses administered to a subject in need thereof may be no more than about 2 pg antigen/g body weight (preferably no more than about 1 pg antigen/g body weight, more preferably no more than about 0.5 pg antigen/g body weight, more preferably no more than about 0.2 pg antigen/g body weight, more preferably no more than about 0.1 pg antigen/g body weight, more preferably no more than about 0.05 pg antigen/g body weight, even more preferably no more than about 0.01 pg antigen/g body weight). In some embodiments, a suitable dose administered to a subject in need thereof may be at least about 0.01 pg antigen/g body weight, at least about 0.05 pg antigen/g body weight, or at least about 0.1 pg antigen/g body weight. For example, suitable dose ranges may include 0.01-0.05 pg antigen/g body weight, 0.01-0.1 pg antigen/g body weight, or 0.01-0.2 pg antigen/g body weight, 0.01-1 pg antigen/g body weight, 0.01-2 pg antigen/g body weight, 0.05-0.1 pg antigen/g body weight, 0.05-0.2 pg antigen/g body weight, 0.05-1 pg antigen/g body weight, or 0.05-2 pg antigen/g body weight, 0.1-0.2 pg antigen/g body weight, 0.1-1 pg antigen/g body weight, or 0.1-2 pg antigen/g body weight.

The compositions, kits, and methods disclosed herein may involve administering a peptide or a panel of peptides as an antigen in order to induce an immune response against a disease. For example, the compositions, kits, and methods disclosed herein may involve administering a peptide or a panel of peptides comprising 5-100 amino acids (preferably 10-20 amino acids). Typically, the peptides have a molecular weight of no more than about 5 kDa (preferably no more than about 4 kDa, more preferably no more than about 3 kDa). Suitable doses of the peptide or the panel of peptides administered to a subject in need thereof as described by moles administered per gram body weight of subject may be no more than about 1 femtomole each peptide/g body weight (preferably no more than about 0.5 femtomoles each peptide/g body weight, more preferably no more than about 0.1 femtomoles each peptide/g body weight, more preferably no more than about 0.05 femtomoles each peptide/g body weight, even more preferably no more than about 0.01 femtomoles each peptide/g body weight). In some embodiments, a suitable dose administered to a subject in need thereof as described by moles each peptide per gram body weight of subject may be at least about 0.01 femtomoles each peptide/g body weight, or at least about 0.05 femtomoles antigen/g body weight. For example, suitable dose ranges may include 0.01-0.05 femtomoles antigen/g body weight, 0.01-0.1 femtomoles antigen/g body weight, 0.01-0.5 femtomoles antigen/g body weight, include 0.01-1 femtomoles antigen/g body weight, 0.05-0.1 femtomoles antigen/g body weight 0.05-0.5 femtomoles antigen/g body weight, and 0.05-1 femtomoles antigen/g body weight.

The compositions, kits, and methods may include or utilize a relatively low amount of antigen to induce an immune response (e.g., a Th-1 response) compared to convention vaccines and methods of the art. (See U.S. Published Application No. 2012/0009220, the contents of which are incorporated herein by reference in their entirety). Conventional vaccines and methods typically involve administering at least about 3 μg of an antigen per dose to a subject. (See, e.g., Scheifele et al. 2005, Hum. Vaccin. 1:180-186; Evans et al. 2001, Vaccine 19:2080-2091; and Kenney et al., N. Engl. J. Med. 351:2295-2301, the contents of which are incorporated herein by reference in their entireties). However, a dose as low as 1 μg of an antigen per dose to a subject also has been proposed. (See U.S. Pat. No. 6,372,223, the content of which is incorporated herein by reference in its entirety). Assuming that the subject is human and weighs approximately 75 kg, a dose of 1 μg antigen translates to a dose of 13.3 pg antigen/g body weight. In some embodiments of the presently disclosed compositions, kits, and methods, a dose rate that is an order of magnitude lower (e.g., no more than about 2 pg antigen/g body weight) can be administered in order to induce an immune response (e.g., a Th1-response). For peptide vaccines as contemplated herein, a dose rate of 1 femtomole each peptide/g body weight or lower can be administered in order to induce an immune response (e.g., a Th1-response). Vaccines that comprise an antigen solution typically have an antigen concentration of no more than about $1.5\times10^{-6}$ g antigen/ml (preferably no more than about $1.5\times10^{-7}$ g antigen/ml, more preferably no more than about $1.5\times10^{-8}$ g antigen/ml, even more preferably no more than about $1.5\times10^{-9}$ g antigen/ml, even more preferably no more than about $1.5\times10^{-10}$ g antigen/ml). In some embodiments, the vaccines comprise an antigen solution having an antigen concentration of at least about $1.5\times10^{-10}$ g antigen/ml. For example, suitable concentration ranges may include $1.5\times10^{-10}$-$3\times10^{-10}$ g antigen/ml, $1.5\times10^{-10}$-$6\times10^{-10}$ g antigen/ml, $1.5\times10^{10}$-$1.5\times10^{-9}$ g antigen/ml, $1.5\times10^{10}$-$3\times10^{-9}$ g antigen/ml, or $1.5\times10^{-10}$-$6\times10^{-9}$ g antigen/ml.

The vaccines disclosed herein may comprise a peptide or a panel of peptides as an antigen. For example, the vaccines may comprise a peptide or a panel of peptides comprising 5-100 amino acids (preferably 10-20 amino acids). Typically, the peptides have a molecular weight of no more than about 5 kDa (preferably no more than about 4 kDa, more preferably no more than about 3 kDa). Vaccines that comprise a peptide or a panel of peptides in solution typically have a solution concentration of each peptide of no more than about $7.5\times10^{-10}$ moles each peptide/ml (preferably no more than about $1.5\times10^{-11}$ moles each peptide/ml, more preferably no more than about $7.5\times10^{-12}$ moles each peptide/ml, more preferably no more than about $1.5\times10^{-12}$ moles each peptide/ml, more preferably no more than about $7.5\times10^{-13}$ moles each peptide/ml, even more preferably no more than about $1.5\times10^{-13}$ moles each peptide/ml). In some embodiments, the vaccines comprise a peptide solution having a concentration of at least about $1.5\times10^{-13}$ moles each peptide/ml, or at least about $1.5\times10^{-13}$ moles each peptide/ml. For example, suitable concentration ranges may include $1.5\times10^{-13}$-$3\times10^{-13}$ moles each peptide/ml, $1.5\times10^{-13}$-$6\times10^{-13}$ moles each peptide/ml, $1.5\times10^{-13}$-$1.5\times10^{-12}$ moles each peptide/ml, $1.5\times10^{-13}$-$3\times10^{-12}$ moles each peptide/ml, $3\times10^{-13}$-$6\times10^{-13}$ moles each peptide/ml, $3\times10^{-13}$-$1.5\times10^{-12}$ moles each peptide/ml, $3\times10^{-13}$-$3\times10^{-12}$ moles each peptide/ml.

Suitable antigens may include polypeptides, peptides, or panels thereof that comprise one or more epitopes of a protein associated with a disease. For example suitable polypeptides, peptides, or panels thereof may comprise one or more epitopes of a protein associated with a pathogen. Suitable polypeptides may comprise the full-length amino acid sequence of a corresponding protein of a pathogen or a fragment thereof. For example, suitable fragments may include 5-200 amino acids (or from 5-150, 5-100, 5-50, 5-25, 5-15, 10-200, 10-100, 10-50, 10-25, 10-25, or 10-15 amino acids) and include at least one epitope of the protein from which the fragment is derived. Suitable antigens for the compositions, kits, and methods may include panels of peptides derived from a protein of a pathogen. For example, a suitable antigen may comprise a panel of at least 2, 3, 4, 5, 10, 25, 50, 100, or more different peptides comprising at least about a 10-20 amino acid sequence from a protein of a pathogen. The different peptide antigens may overlap at the N-terminus, the C-terminus, or both termini with at least one other peptide antigen of the composition, for example, by at least about 1, 2, 3, 4, 5, 6, 7, 8, 9, or 10 amino acids.

Nature of Protein, Polypeptide, or Peptide Antigens.

The presently disclosed compositions, kits, and methods contain and/or utilize a protein, polypeptide, or peptide for inducing an immune response. However, the presently disclosed compositions, kits, and methods are distinguished from live vaccines or inactivated vaccines in that the protein, polypeptide, or peptide of the compositions, kits, and methods is isolated, purified, recombinant, or synthesized in vitro (e.g., chemically synthesized). For example, the compositions, kits, and methods contain and/or utilize a protein, polypeptide, or peptide that is recombinant, expressed in a host cell, and isolated or purified. In another example, the compositions, kits, and methods may contain a panel of polypeptides or peptides that are chemically synthesized (e.g., using liquid phase synthesis, or solid phase synthesis such as Fmoc solid phase synthesis or t-boc solid phase synthesis).

As utilized herein, a protein, polypeptide, and peptide refer to a molecule comprising a chain of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The terms "protein," "polypeptide," and "peptide" may be referred to interchangeably herein. However, the terms may be distinguished as follows. A "protein" typically refers to the end product of transcription, translation, and post-translation modifications in a cell. Accordingly, a protein typically exhibits a biological function. A polypeptide is typically an amino acid chain of length≥100 amino acids (Garrett & Grisham, Biochemistry, $2^{nd}$ edition, 1999, Brooks/Cole, 110, which is incorporated herein by reference in its entirety). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A peptide, in contrast to a polypeptide, typically is a short polymer of amino acids, of a length typically of 20 or less amino acids (Garrett & Grisham, Biochemistry, $2^{nd}$ edition, 1999, Brooks/Cole, 110, which is incorporated herein by reference in its entirety). In some embodiments, a peptide as contemplated herein may include no more than about 10, 11, 12, 13, 14, 15, 16, 17, 18, 19, or 20 amino acids.

Polypeptides and peptides as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

A "fragment" of a protein or a polypeptide as contemplated herein refers to a contiguous portion of the amino acid sequence of the protein or polypeptide. A fragment of a protein or polypeptide refers to less than a full-length amino acid sequence of the protein or polypeptide (e.g., where the full-length amino acid sequence is truncated at the N-terminus, the C-terminus, or both termini). For example, a fragment of a protein or polypeptide may comprise or consist of a 5-200, 5-150, 5-100, 5-50, 5-25, 5-15, 10-200, 10-150, 10-100, 10-50, 10-25, or 10-15 contiguous amino acid sequence of the full-length protein or polypeptide. An "immunogenic fragment" of a protein or polypeptide is a fragment of a protein or polypeptide typically at least 5 or 10 amino acids in length that includes one or more epitopes of the full-length protein or polypeptide (e.g., a peptide present in the full-length protein or polypeptide).

Immune Stimulators and Vaccines.

The compositions disclosed herein may include pharmaceutical compositions that are administered as immune stimulators or vaccines. Typically, the pharmaceutical composition comprises an effective amount or concentration of an immune stimulator and optionally an antigen for inducing a protective or therapeutic immune response against a disease, which may include, but is not limited to infection by a pathogen, cancer, or an autoimmune disease. Inducing a protective or therapeutic immune response may include inducing a Th1 response to one or more epitopes of a protein associated with the disease (e.g., a protein associated with a pathogen, cancer, or autoimmune disease).

Where the disease relates to infection by a pathogen, inducing a protective response may include inducing sterilizing immunity against the pathogen. Inducing a therapeutic response may include reducing the pathogenic load of a subject, for example, as determined by measuring the amount of circulating pathogen before and after administering the composition. Inducing a therapeutic response may include reducing the degree or severity of at least one symptom of infection by the pathogen.

The presently disclosed methods may be utilized for inducing a protective or therapeutic immune response against disease by administering the pharmaceutical compositions disclosed herein (e.g., as immunogenic compositions or vaccines) to a subject in need thereof, which may include a human or non-human having or at risk for acquiring the disease. The methods may include administering a first pharmaceutical composition and optionally may include administering a second pharmaceutical composition to augment or boost an immunogenic response induced by the first pharmaceutical composition. The first and second pharmaceutical compositions may be the same or different. The optionally administered second pharmaceutical composition may be administered prior to, concurrently with, or after administering the first pharmaceutical composition. In some embodiments, the first composition is administered and then the second composition is administered after waiting at least about 4, 5, or 6 weeks. The first composition (and the second composition) may be administered one or more times.

The presently disclosed compositions, kits, and methods may be utilized to protect against or treat infection by a pathogen. As used herein, a "pathogen" includes, but is not limited to a living microorganism such as bacteria, viruses, and fungi that cause disease in a host. Suitable pathogens for treatment of prevention by the compositions, kits, and methods disclosed herein may include pathogens that are susceptible to cell-mediated immune responses in the host (e.g., Th1-mediated immune response) such as *Chlamydia* and infectious bursal disease virus (IBDV).

The presently disclosed compositions, kits, and methods also may be utilized to protect against or treat cancers or hyperproliferative disorders that are susceptible to cell-mediated immune responses in the host (e.g., Th1-mediated immune response), which may include, but are not limited to adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

The presently disclosed compositions, kits, and methods also may be utilized to protect against or treat autoimmune diseases that are susceptible to cell-mediated immune responses in the host (e.g., Th1-mediated immune response), which may include, but are not limited to autoimmune haematological disorders (including e.g. hemolytic anaemia, aplastic anaemia, pure red cell anaemia and idiopathic thrombocytopenia), systemic lupus erythematosus, polychondritis, scleroderma, Wegener granulomatosis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis or glomerulonephritis (with and without nephrotic syndrome, e.g. including idiopathic nephrotic syndrome or minimal change nephropathy).

The presently disclosed composition may be administered to potentiate or enhance an immune response. As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth"). Preferably, a 5-fold, or more preferably a 10-fold or greater, enhancement in T-cell responses may be obtained by administering the pharmaceutical composition disclosed herein.

The presently disclosed compositions, kits, and methods may be utilized to induce an immune response, including, but not limited to a cellular immune response such as a "Th1-response." As utilized herein, a Th1-response may be characterized by cytokine production such as interferons (e.g., IFN-γ), tumor necrosis factor (e.g., TNF-β), and interleukins (e.g., IL-2). A Th1-response also may be characterized by increased killing efficiency of macrophages with respect to a pathogen and the proliferation of cytotoxic $CD8^+$ cells against the pathogen. A Th1 response also may be characterized by the presence of opsonizing antibodies against the antigen. Th1-responses may be assessed as described previously. (See Li et al., Vaccine 28 (2010) 1598-1605, the content of which is incorporated herein by reference in its entirety).

In some embodiments, the presently disclosed compositions, kits, and methods may be utilized to induce a Th1-response preferentially relative to other responses, for example, a Th2-response. As utilized herein, a Th2-response may be characterized by cytokine production such as interleukins (e.g., IL-4, IL-5, IL-6, IL-10, and IL-13). A Th2-response also may be characterized by B-cell stimulation and proliferation to induce B-cell antibody class switching and to increase neutralizing antibody production. Computer models have suggested that a Th1-response versus a Th2-response may be dependent on antigen dosage. (See Bergmann et al., Bulletin of Math. Biol. (2002) 64, 425-446; and Bergmann et al., Bulletin of Math. Biol. (2001) 63, 405-439, the contents of which are incorporated by reference in their entireties).

The presently disclosed composition, kits, and methods may be utilized to prevent or treat infections by pathogens that are susceptible to a T-cell mediated immune response (e.g., a Th1 immune response). In some embodiments, the presently disclosed composition, kits, and methods may be utilized to prevent or treat infections by *Chlamydia* spp. As is the case for many other intracellular pathogens, T-lymphocytes play a key role in a protective host response to *Chlamydia* infection (Morrison et al., 1995, Infect. Immun. 63:4661-4668; Rank, 2006, In *Chlamydia* Genomics and Pathogenesis. P. M. Bavoil and B. Wyrick (ed.). Horizon Bioscience Press, Norfolk, U. K.). IFN-γ producing Th1 helper lymphocytes are indispensible for efficient and complete elimination of chlamydial infection (Perry et al., 1997, J. Immunol. 158:3344-3352; Rottenberg et al., 2000, J. Immunol. 164:4812-4818; Vuola et al., 2000, Infect. Immun. 68:960-964.), and ablation of Th1 cells or effector functions results in increased chlamydial disease and failure to eliminate chlamydiae (Cotter et al., 1997, Infect. Immun. 65:2145-2152; Lu et al., 2000, Mol. Med. 6:604-612; Morrison et al., 1995, Infect. Immun. 63:4661-4668; Wang et al., 1999, Eur. J. Immunol. 29:3782-3792.) They restrict chlamydial replication via Th1-type effector cytokines, most prominently IFN-γ, contributing to a DTH response (Perry et al., 1997; Rottenberg et al., 2000). Such protective DTH responses are characterized by tissue infiltration of $CD4^+$ T cells and macrophages and release of proinflammatory Th1 cytokines such as IL-1, IL-2, IL-12, IFN-γ, or TNF-α.

Formulation of the Pharmaceutical Compositions

The pharmaceutical compositions disclosed herein may be formulated as vaccines for administration to a subject in need thereof. Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients (e.g., powder excipients such as lactose, sucrose, and mannitol), and surfactants (e.g., non-ionic surfactants such as Kolliphor® HS 15 non-ionic solubilizer and emulsifying agent, Kollidon® 12 PF soluble polyvinylpyrrolidone, and Tween®-20 non-ionic polyoxyethylene surfactant), as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered prophylactically or therapeutically. In prophylactic administration, the vaccines may be administered in an amount sufficient to induce a cellular immune response for protecting against infection or for treating infection. In therapeutic applications, the vaccines are administered to a patient in an amount sufficient to elicit a therapeutic effect (e.g., an immune response to the administered antigen, which cures or at least partially arrests or slows symptoms and/or complications of disease (i.e., a "therapeutically effective dose")).

The compositions disclosed herein may be delivered via a variety of routes. Typical delivery routes may include parenteral administration, intradermal, intramuscular, intraperitoneal, subcutaneous, and/or intracutaneous delivery). Other routes include intranasal and intrapulmonary routes. Further routes include oral administration, intravaginal, and intrarectal routes. Formulations of the pharmaceutical compositions may include liquids (e.g., solutions and emulsions), sprays, and aerosols. In particular, the compositions may be formulated as aerosols or sprays for intranasal or intrapulmonary delivery. Suitable devices for administering aerosols or sprays for intranasal or intrapulmonary delivery may include inhalers and nebulizers.

The compositions disclosed herein may be co-administered or sequentially administered with other immunological, antigenic or vaccine or therapeutic compositions, including an adjuvant, or a chemical or biological agent given in combination with an antigen to enhance immunogenicity of the antigen. Additional therapeutic agents may include, but are not limited to, cytokines such as interferons (e.g., IFN-γ) and interleukins (e.g., IL-2).

Prime-Boost Vaccination Regimen

As used herein, a "prime-boost vaccination regimen" refers to a regimen in which a subject is administered a first composition and then after a determined period of time (e.g., after about 2, 3, 4, 5, or 6 weeks), the subject is administered a second composition, which may be the same or different than the first composition. The first composition (and the second composition) may be administered one or more times. The disclosed methods may include priming a subject with a first composition by administering the first composition at least one time, allowing a predetermined length of time to pass (e.g., at least about 2, 3, 4, 5, or 6 weeks), and then boosting by administering the same composition or a second, different composition.

Characterization of the Immune Response in Vaccinated Individuals

The pharmaceutical compositions disclosed herein may be delivered to subjects at risk for a disease (e.g., infection with a pathogen) or to subjects who have acquired the disease (e.g., subject who are infected with a pathogen). In order to assess the efficacy of an administered immunogenic composition or vaccine, the immune response can be assessed by measuring the induction of cell-mediated responses and/or antibodies to particular epitopes. T-cell responses may be measured, for example, by using tetramer staining of fresh or cultured PBMC, ELISPOT assays or by using functional cytotoxicity assays, which are well-known to those of skill in the art. Antibody responses may be measured by assays known in the art such as ELISA. Titer or load of a pathogen may be measured using methods in the art including methods that detect nucleic acid of the pathogen. (See, e.g., U.S. Pat. No. 7,252,937, the content of which is incorporated by reference in its entirety). Immune responses also may be characterized by physiological responses. (See Li et al., Vaccine 28 (2010) 1598-1605; and Stemke-Hale et al., Vaccine 2005 Apr. 27; 23(23):3016-25, the content of which re incorporated herein by reference in their entireties.) Immune response also may be measured by pathological responses such as total weight loss or gain for the animal (e.g., weight loss associated with infection by a pathogen). Immune response also may be measured by pathological responses such as weight loss or gain for an organ of the animal (e.g., lung-weight gain in mice infected with *C. abortus*, or weight loss or gain for the Bursa of Fabricius in chicken infected with infectious bursa disease virus).

EXAMPLES

The following examples are illustrative and are not intended to limit the disclosed subject matter.

Glossary of Terms and Acronyms and Description of Experiments

PLGA RG502H: biodegradable poly (lactide-co-glycolide-poly (50%:50%) copolymer.

PLGA-PEG: biodegradable poly (lactide-co-glycolide-poly (50%:50%) copolymer, chemically modified by incorporation of 5% polyethylene glycol (PEGylation) with a molecular weight of 5,000.

PLA L206S: biodegradable poly(L-lactide) polymer.

Nelfinavir: nelfinavir mesylate, which is an inhibitor of the protease of human immunodeficiency virus and is used as an antiretroviral drug. Nelfanivir also has immunostimulatory and/or immunopotentiating activity and is poorly water soluble.

Pluronic® L121 polyoxyethylene-polyoxypropylene block copolymer, which is a surfactant and an adjuvant.

Resiquimod or R-848: selective ligand for the Toll-like receptor 7 (TLR7) in the mouse, which is an adjuvant.

Trehalose-di-behenate: synthetic analogue of trehalose dimycolate from the cord factor of the tubercle *bacillus*, which is an adjuvant.

Poly (I:C): double-stranded polyribonucleotide poly(I)•poly(C), which is an adjuvant and which induces interferon.

Q-VD-OPH: pan-caspase inhibitor that irreversibly binds to activated caspases to block apoptosis. Q-VD-OPH is composed of the amino acids valine and aspartate with N-terminal quinolyl and a C-terminal di-fluorophenoxy methylketone group. Q-VD-OPH is highly cell permeable and non-toxic in vitro and in vivo at high concentrations.

Emricasan or IDN-6556: broad-spectrum irreversible caspase inhibitor that blocks apoptosis.

Kolliphor® HS 15: polyethylene glycol-15-hydroxy stearate, USP: Polyoxyl-15-Hydroxystearate, Ph. Eur.: Macrogol 15 Hydroxystearate, which is a non-ionic solubilizer and emulsifying agent.

Kollidon® 12 PF: soluble polyvinylpyrrolidone with a molecular weight of 2,000-3,000, which is a solubilizing agent, dispersant, and crystallization inhibitor.

Tween®-20: non-ionic polyoxyethylene surfactant.

Benzalkonium Chloride: quaternary ammonium compound with antimicrobial efficacy over a wide pH range at a concentration of less than 0.02%.

PBS: phosphate-buffered saline.

IBDV: Infectious Bursal Disease Virus, which is double-stranded DNA virus of the Birnavirus family causes an infection of the Bursa of Fabricius in young chickens which destroys the B lymphocytes in this organ. The absence of B lymphocytes renders these chickens unable to produce antibodies and makes them therefore highly susceptible to many infectious diseases.

C3H/HeJ: inbred mouse strain that has a mutation in the Toll-like receptor 4 (TLR4) gene that results in a truncated (shortened) TLR4 protein. TLR-4 binds bacterial lipopolysaccharide (LPS) and triggers the inflammatory response after LPS exposure. Due to the virtually absent LPS response, C3H/HeJ mice mount very little innate inflammatory response and also exhibit an aberrant adaptive immune response. These mice are extremely sensitive to gram-negative bacteria including chlamydiae. After chlamydial intranasal challenge infection they remain without discernible clinical symptoms for about one week, but then a large fraction of challenged mice die over the next two weeks due to uninhibited overwhelming growth of chlamydiae. Treatment with immune stimulators can partially substitute for the absent TLR4 signaling and make these mice more resistant to chlamydial infection. Therefore, immune stimulator experiments in mice were conducted with this mouse strain.

A/J: inbred mouse strain that produces a weak innate immune response with low inflammation. After intranasal challenge with chlamydiae, naïve mice of this strain develop severe disease and high chlamydial lung loads due to poor control of chlamydial growth. In contrast, mice that are immune to chlamydiae due to previous exposure to a low level infection or due to successful vaccination are fully protected and do not develop disease. Therefore, vaccine experiments were in part conducted with this mouse strain.

129S6: inbred mouse strain that has a defect in the effector arm of the innate immune system with aberrant DAP12 signaling in natural killer (NK) T cells. Due to this defect, naïve 129S6 mount a weak innate immune response to chlamydiae and are highly susceptible to *C. abortus*. In contrast, 129S6 mice mount a fully protective adaptive immune response after exposure to a low level infection or due to successful vaccination, and are fully protected and do not develop disease after vaccination. Therefore, vaccine experiments were in part conducted with this mouse strain.

Mouse experiments: In the mouse challenge for infection experiments with *Chlamydia abortus*, only female mice are used because they can be maintained in cages without the severe fighting that is common for male mice. Typically, for immune stimulator experiments without prior vaccination, mice of 10 weeks of age are used. For vaccine experiments, younger mice of about 6 weeks of age are first vaccinated or receive an immunizing low-dose intranasal *C. abortus* infection, and are challenged with a high dose infection 4-6 weeks later at 10-12 weeks of age. For intranasal challenge, the mice receive a light isoflurane anesthesia, and 20 μl of a suspension of $10^8$ to $3\times10^8$ *C. abortus* viable bacteria in sucrose-phosphate-glutamate buffer are deposited on the nostrils, from where the mice inhale the bacteria. For immune stimulator experiments, the mice are observed until 3 weeks later and surviving mice are then euthanized. In vaccine experiments, mice are euthanized between 10-12 days after challenge.

In the vaccine experiments, mouse lungs were weighed and homogenized, DNA was extracted, and *C. abortus* genome lung loads are determined by a real-time PCR targeting the *Chlamydia* spp. 23S rRNA gene. All mouse experiments are approved by the Auburn University Institutional Animal Care and Use Committee (IACUC).

In all vaccine experiments, the antigens used were 20-mer peptides of the C. abortus vaccine candidate proteins Dnax2, GatA, GatC, Omp90A, Pbp3. These peptides overlapped by 10 amino acids and therfore comprised all possible 10-mer peptides of these proteins.

Chicken experiments: In the chicken experiments for evaluation of the immune stimulator treatment on resistance to naturally circulating infections and/or on body growth without experimental challenge infection, freshly hatched standard hybrid broiler chickens weighing 45-50 g were used on the day of hatching and subcutaneously injected with the microparticle immune stimulator. The body weight of these chickens was determined after 3 weeks.

For IBDV vaccine experiments, freshly hatched standard hybrid broiler chickens were immunized with microparticles containing 20-mer overlapping peptides of all proteins of the IBDV virus. After 3 weeks, the chickens received an intranasal challenge of the virus suspended in PBS. The chickens were weighed and euthanized after 7 days, and sex, and weight and appearance of the Bursa of Fabricius were determined.

Example 1. Immune Stimulator Experiment in Mice

The ability of a composition comprising a suspension of biodegradable particles to induce an innate immune response as an "immune stimulator" in mice was tested under the parameters of Table 1.

TABLE 1

| | |
|---|---|
| Model System | Immune Stimulator Experiment in Mice: day-21 post-challenge termination survival analysis |
| Mouse strain | C3H/HeJ, 10 weeks old at start of experiment |
| Challenge | $10^8$ C. abortus elementary bodies, 21, 11, or 1 days after immune stimulator |
| Administration | 1× intranasal (IN) 10 μg microparticle immune stimulator preparation & 30 μg lactose microfine powder in 20 μl PBS/0.1% Kolliphor ® HS 15 non-italic solubilizer and emulsifying agent 1× PBS control: 20 μl intranasal |
| Formulation | Microparticles (1-10 μm) spray-dried from PLGA-PEG & Pluronic ® L121 block copolymer (3:2) |
| Conclusion | Local (intranasal) administration of the microparticle immune stimulator at the site of the challenge inoculation was found to be effective given 1 day before challenge up to at least 3 weeks before the challenge inoculation. |

As indicated in Table 1, microparticles having an effective average diameter of 1-10 μm were prepared by spray-drying a solution of PLGA-PEG and Pluronic® L121 block copolymer (3:2). (See FIG. 1A). In order to prepare the immune stimulator, 10 μg of the microparticles were mixed with 30 μg lactose microfine powder and added to 20 μl PBS/0.1% Kolliphor® HS 15 non-ionic solubilizer and emulsifying agent to form a suspension. The immune stimulator (20 μl) was administered intranasally to 10 week old mice (C3H/HeJ strain). As a control, 1×PBS was administered. The mice were challenged at 1, 11, or 21 days post-administration by administering intranasally $10^8$ C. abortus elementary bodies. The results presented in FIGS. 1B, C, and D illustrate that mice administered the immune stimulator exhibited a higher survival rate than mice administered the control. These results demonstrate that an immune stimulator that did not contain an antigen against C. abortus may be administered in order to induce innate immunity.

Example 2. Immune Stimulator Experiment in Mice

The ability of a composition comprising a suspension of biodegradable particles and an adjuvant to induce an innate immune response as an "immune stimulator" in mice was tested under the parameters of Table 2.

TABLE 2

| | |
|---|---|
| Model System | Immune Stimulator Experiment in Mice: day-21 post-challenge termination survival analysis |
| Mouse strain | C3H/HeJ, 10 weeks old at start of experiment |
| Challenge | 3 × $10^8$ C. abortus elementary bodies, 1 day after immune stimulator |
| Administration | 1× intranasal, 10 μg of each microparticle immune stimulator preparation suspended in 20 μl suspension buffer (0.1% Kolliphor ® HS 15 non-ionic solubilizer and emulsifying agent, 0.001% Benzalkonium Chloride in PBS); prior to suspension, each immune stimulator preparation was mixed with the 3-fold amount of lactose microfine powder. |
| Formulation | Microparticles (0.5-10 μm) spray-dried from a biodegradable carrier & adjuvant: PLGA RG502H and adjuvants: 1) Pluronic ® L121 block copolymer: 3.5 μg Pluronic ® L121 block copolymer and 6.5 μg PLGA RG502H; 2) Resiquimod: 0.2 μg resiquimod and 9.8 μg PLGA RG502H; 3) No adjuvant: 10 μg PLGA RG502H. |
| Conclusions | 1) A PLGA RG502H plus adjuvant microparticle preparation administered intranasally at 10 μg per mouse was an effective immune stimulator. 2) Addition of adjuvants to the PLGA RG502H microparticles augmented the immune stimulatory effect. 3) Different adjuvants mediated a similar immune stimulatory effect. |

Figure 2:
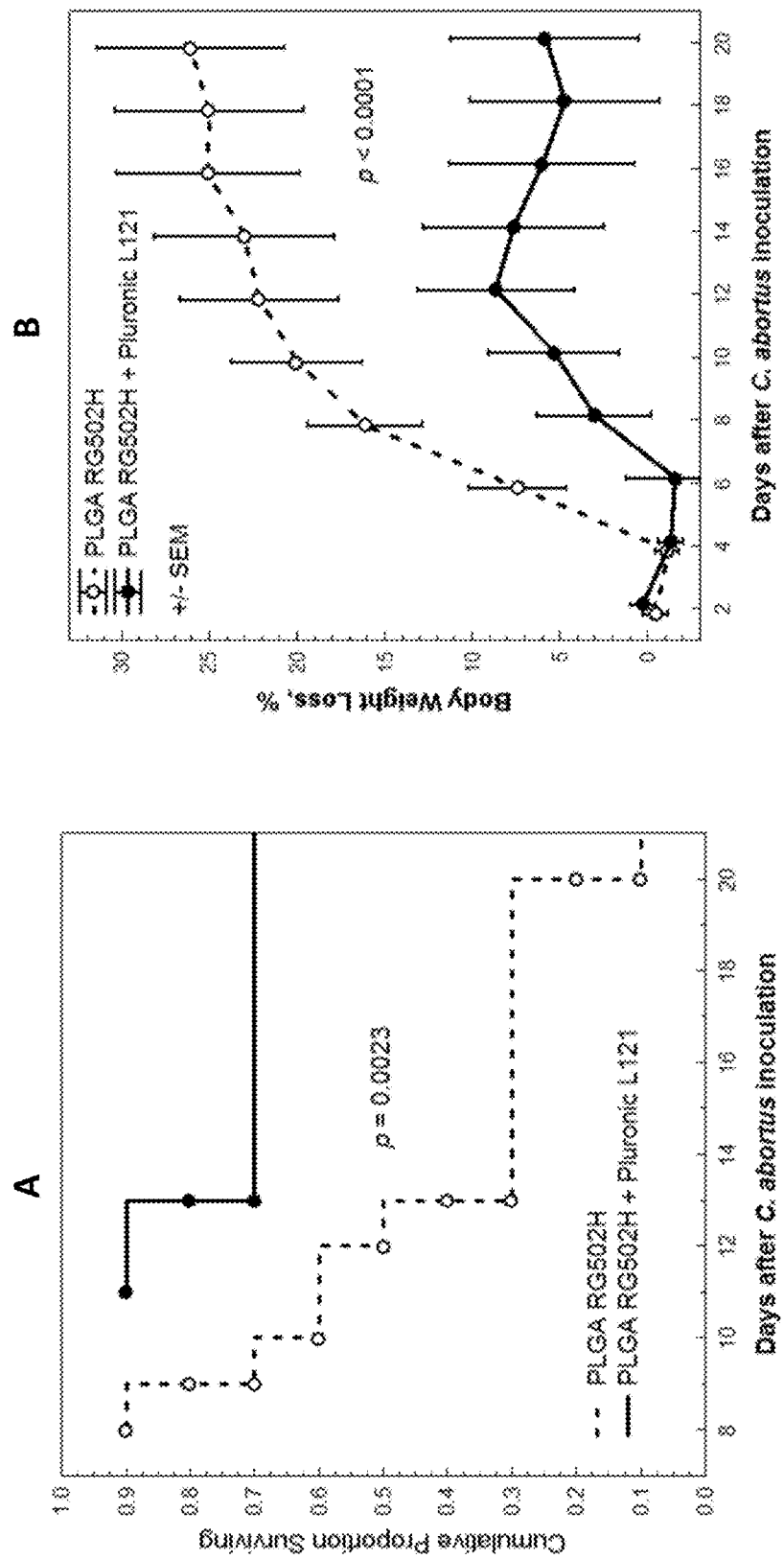
FIG. 2. A. Cumulative proportion surviving versus days after challenge with *C. abortus* for mice administered PLGA RG502H particle composition+Pluronic® L121 block copolymer versus PLGA RG502H composition without Pluronic® L121 block copolymer. B. Body weight loss versus days after challenge with *C. abortus* for mice administered PLGA RG502H particle composition+Pluronic® L121 block copolymer versus PLGA RG502H composition without Pluronic® L121 block copolymer. C. Cumulative proportion surviving versus days after challenge with *C. abortus* for mice administered PLGA RG502H composition+Resiquimod versus PLGA RG502H particle composition without Pluronic® L121 block copolymer. C. Body weight loss versus days after challenge with *C. abortus* for mice administered PLGA RG502H composition+Resiquimod versus PLGA RG502H particle composition without Pluronic® L121 block copolymer.
Figure 2:
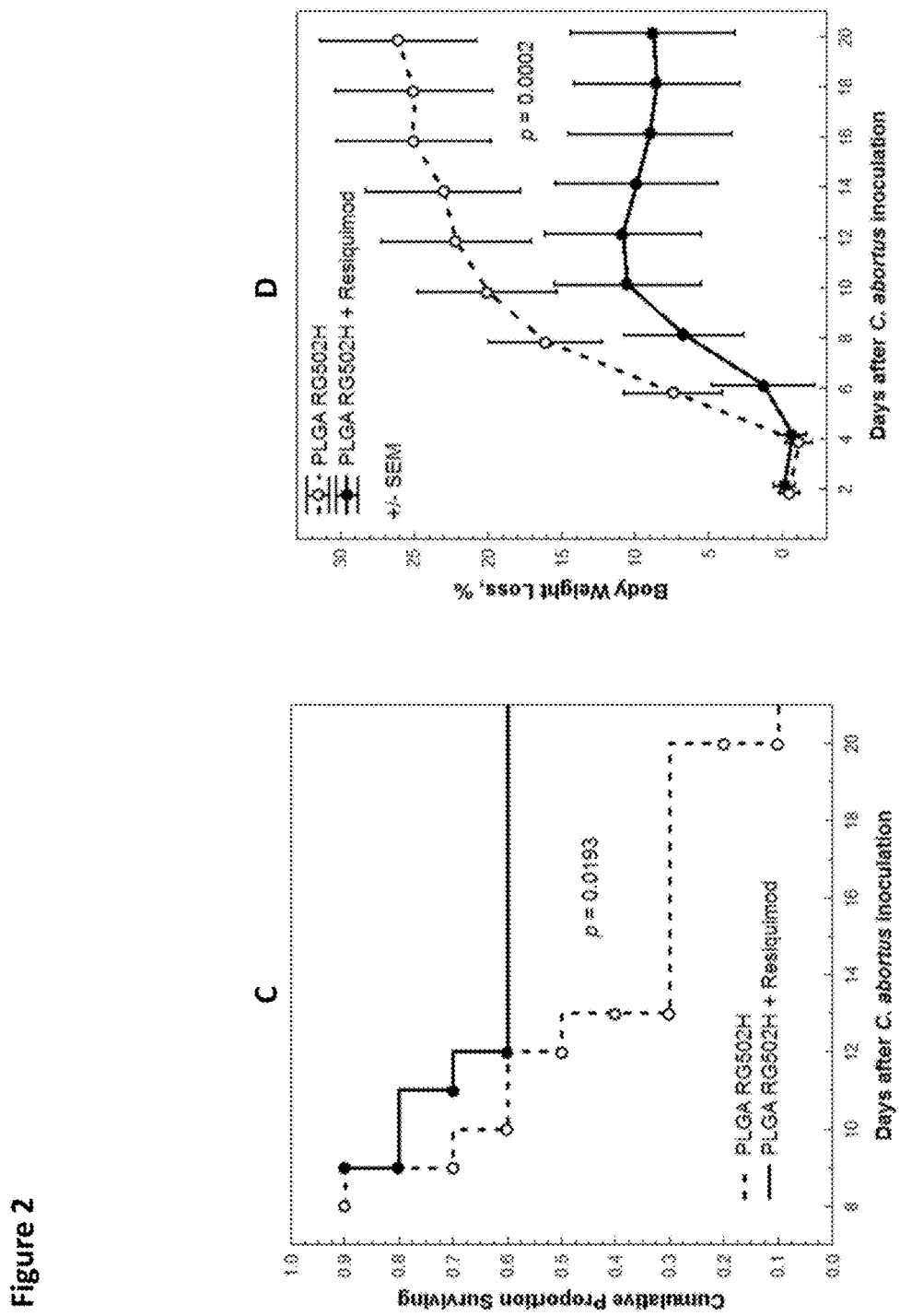

As indicated in Table 2, microparticles having an effective average diameter of 0.5-10 μm were prepared by spray-drying a solution of PLGA RG502H (poly (lactide-co-glycolide-poly (50%:50%) copolymer) and adjuvants. Microparticle formulation 1) included 6.5 μg PLGA RG502H and 3.5 μg Pluronic® L121 block copolymer; Microparticle formulation 2) included 9.8 μg PLGA RG502H and 0.2 μg resiquimod; and Microparticle formulation 3) included 10 μg PLGA RG502H (i.e. no adjuvant). The microparticle formulations were mixed a 3-fold amount of lactose microfine powder and added to 20 μl suspension buffer (0.1% Kolliphor® HS 15 non-ionic solubilizer and emulsifying agent, 0.001% Benzalkonium Chloride in PBS) to prepare an immune stimulator. The immune stimulator (20 μl) was administered intranasally to 10 week old mice (C3H/HeJ strain). The mice were challenged at 1 day post-administration by administering intranasally $10^8$ C. abortus elementary bodies. The results presented in FIGS. 2A and B illustrate that mice administered the immune stimulator comprising an adjuvant exhibited a higher survival rate and a lower body weight loss than mice administered the immune stimulator lacking an adjuvant. These results demonstrate that adjuvants may used to augment the effect of an immune stimulator comprising the microparticles to induce innate immunity.

Example 3. Immune Stimulator Trial in Chickens

The ability of a composition comprising a suspension of biodegradable particles to induce an innate immune response as an "immune stimulator" in chickens was tested under the parameters of Table 3.

TABLE 3

| | |
|---|---|
| Model System | Immune Stimulator Trial in Chickens: Two pooled growth experiments from hatching to day 28, with immune stimulator or control suspension buffer administration on the day of hatching; survival analysis of impact on losses of chickens |

TABLE 3-continued

| | |
|---|---|
| Chicken strain | Standard broiler chickens |
| Treatment | 1 × 200 μl subcutaneously |
| Challenge | NONE |
| Formulations | 1) 270 μg Microparticle Immune Stimulator (1-10 μm) spray-dried from PLGA-PEG & Pluronic ® L121 block copolymer (6.5:3.5) combined with & 810 μg lactose microfine powder<br>2) Suspension Buffer (200 μl: 0.1% Kolliphor ® HS 15 non-ionic solubilizer and emulsifying agent, 0.001% Benzalkonium Chloride in PBS) |
| Dosage | The microparticle immune stimulator dose was allometrically scaled 27-fold for 1,600 g target weight of chickens at 3 weeks as compared to 10 μg microparticle immune stimulator for 20 g mouse target weight: $(1,600/20)^{3/4} = 26.7$. |
| Antigen | NONE |
| Conclusion | Subcutaneous administration of microparticle immune stimulator delivered as spray-dried PLGA-PEG microparticles that contain co-polymer adjuvant was effective. The effect was observed using a single 270 microgram total dose of the immune stimulator. |

As indicated in Table 3, microparticles having an effective average diameter of 1-10 μm were prepared by spray-drying a solution of PLGA-PEG and Pluronic® L121 block copolymer (6.5:3.5). In order to prepare the immune stimulator composition, 270 μg of the microparticles were combined with 810 μg lactose microfine powder and added to 200 μl of suspension buffer (0.1% Kolliphor® HS 15 non-ionic solubilizer and emulsifying agent, 0.001% Benzalkonium Chloride in PBS). The 270 μg of the microparticles was arrived at by allometrically scaling the 10 μg microparticle amount used for a 20 g mouse based on the formula (BW/20)3/4=allometric scaling factor, where "BW" equals the body weight of the target animal in grams. Assuming that the target weight of a chicken is 1600 g, the allometric scaling factor is $(1,600/20)^{3/4}=26.7$. Multiplying the 10 μg microparticle amount used for a 20 g mouse by the scaling factor of 26.7 results in ~270 μg.

Figure 3:
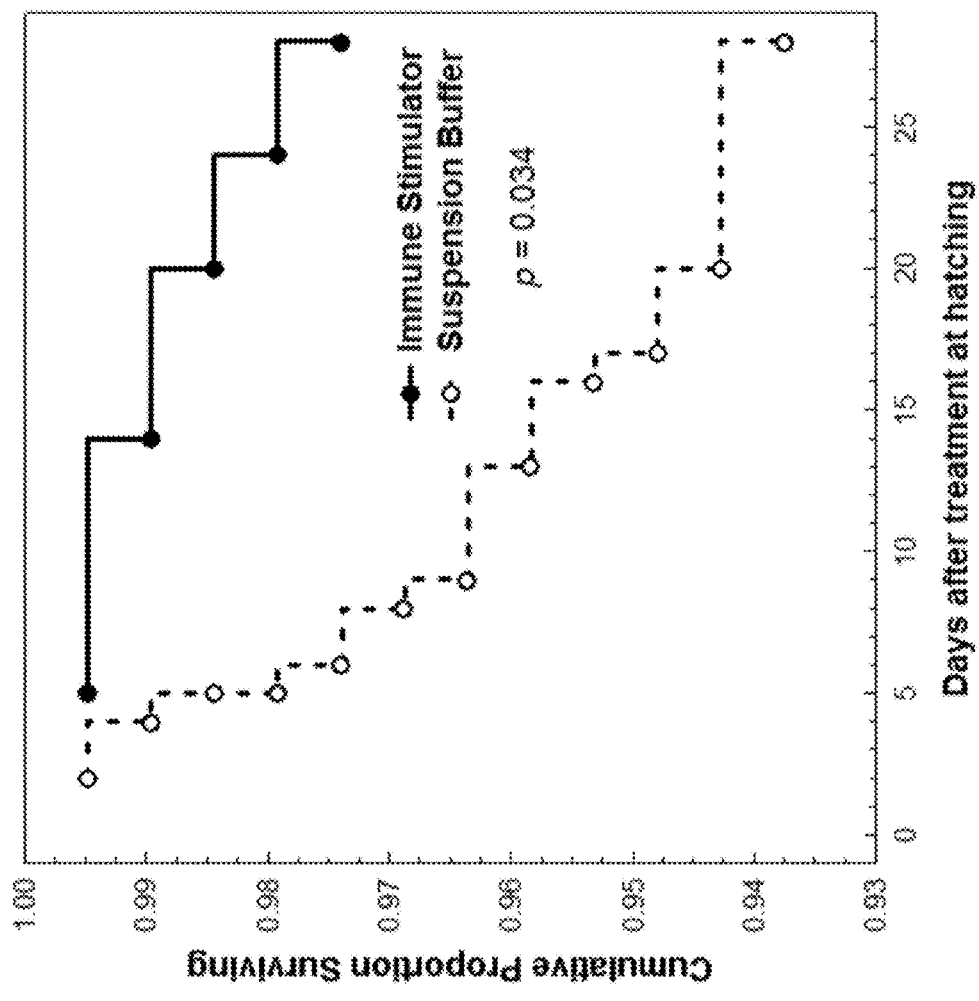
FIG. 3. Cumulative proportion surviving versus days after treatment at hatching for chickens administered immune stimulator versus buffer control.

The immune stimulator thus formulated (200 μl) was administered subcutaneously to standard broiler chickens on the day of hatching. Suspension buffer without microparticles was administered as a control. The chickens were not challenged and the cumulative survival rate was determined for chickens administered the immune stimulator versus control. The results presented in FIG. 3 illustrate that chickens administered the immune stimulator exhibited a higher cumulative survival rate than chickens administered the control. These results demonstrate that an immune stimulator that did not contain an antigen may be administered in order to increase survival rate in chickens.

Example 4. Immune Stimulator and Growth Enhancement Trial in Chickens

The ability of a composition comprising a suspension of biodegradable particles to induce an innate immune response as an "immune stimulator" and to enhance growth in chickens was tested under the parameters of Table 4.

TABLE 4

| | |
|---|---|
| Model System | Immune Stimulator & Growth Enhancement Trial in Chickens:<br>Evaluation of immune stimulator effect on body weight |
| Animal | chickens, hatched on starting day of experiment |
| Administration | 1× subcutaneous 270 μg microparticle immune stimulator preparation & 810 μg lactose microfine powder in 200 μl PBS/0.1% Kolliphor ® HS 15 non-ionic solubilizer and emulsifying agent<br>1x PBS control: 200 μl subcutaneous |
| Formulation | Microparticles (1-10 μm) spray-dried from PLGA-PEG & Pluronic ® L121 block copolymer (6.5:3.5) |
| Conclusions | Subcutaneous injection of allometrically scaled 270 μg of the microparticle immune stimulator on the day of hatching increases the body weight of 22-day old chickens by 116 g from 886 g to 1012 g (14.2%). |

As indicated in Table 4, microparticles having an effective average diameter of 1-10 μm were prepared by spray-drying a solution of PLGA-PEG and Pluronic® L121 block copolymer (6.5:3.5). In order to prepare the immune stimulator composition, 270 μg of the microparticles were combined with 810 μg lactose microfine powder and added to 200 μl of suspension buffer (0.1% Kolliphor® HS 15 non-ionic solubilizer and emulsifying agent, 0.001% Benzalkonium Chloride in PBS).

Figure 4:
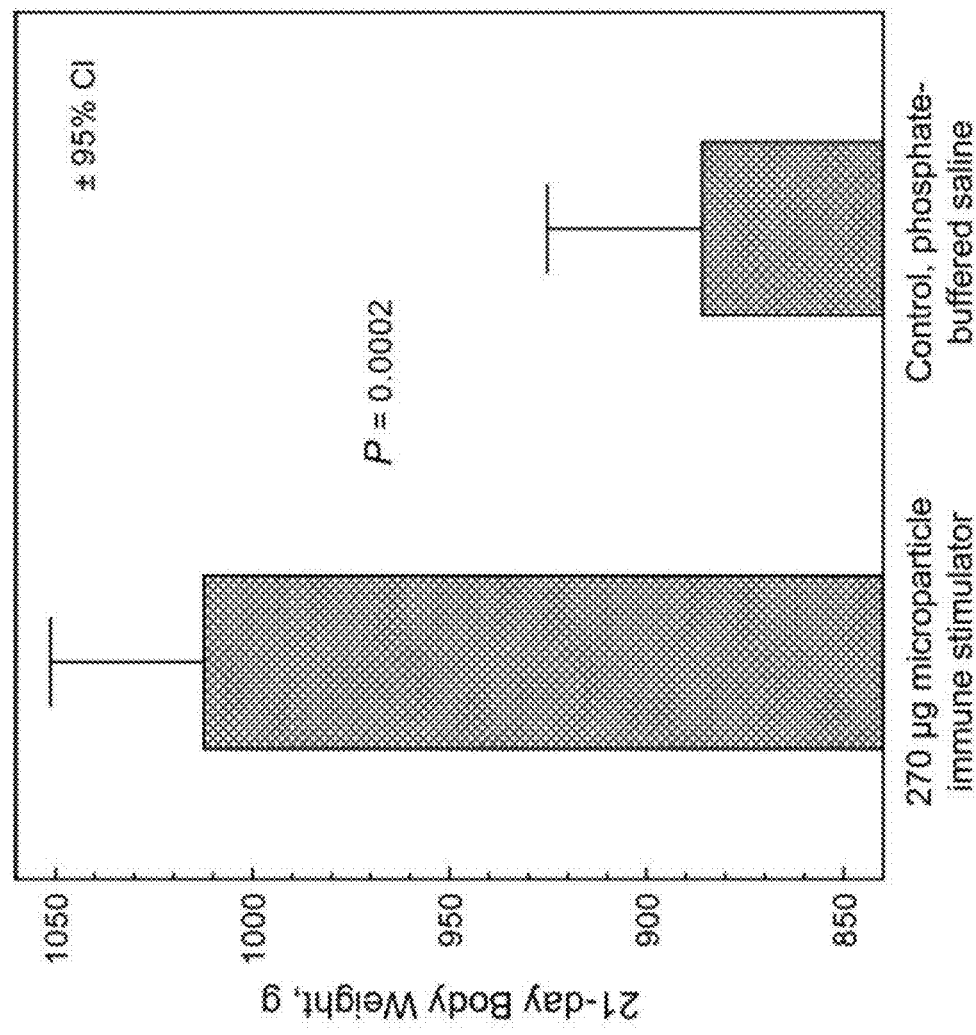
FIG. 4. Body weight after 21 days for chickens administered immune stimulator versus buffer control.

The immune stimulator thus formulated (200 μl) was administered subcutaneously to standard broiler chickens on the day of hatching. Suspension buffer without microparticles was administered as a control. The chickens were not challenged and weight gain was assessed 21 days post-administration. The results presented in FIG. 4 illustrate that chickens administered the immune stimulator exhibited a higher average body weight than chickens administered the control. These results demonstrate that an immune stimulator that did not contain an antigen may be administered in order to enhance growth in chickens.

Example 5

The ability of a composition comprising a suspension of biodegradable particles to induce an innate immune response as an "immune stimulator" and to improve feed conversion rate in chickens was tested under the parameters of Table 5.

TABLE 5

| | |
|---|---|
| Model System | Immune Stimulator & Growth Enhancement Trial in Chickens: Evaluation of immune stimulator effect on feed conversion |
| Chicken strain | Standard broiler chickens |
| Challenge | NONE |
| Treatment | 1× subcutaneous 270 μg microparticle immune stimulator preparation & 810 μg lactose microfine powder in 200 μl suspension buffer (PBS/0.1% Kolliphor ® HS 15 non-ionic solubilizer and emulsifying agent/0.001% Benzalkonium Chloride) at hatching 1x control: 200 μl suspension buffer subcutaneously at hatching |
| Formulation | Microparticles (1-10 μm) spray-dried from PLGA-PEG & Pluronic ® L121 block copolymer (6.5:3.5) |
| Antigen Dose | NONE |
| Conclusion | A single subcutaneous, allometrically scaled dose of the microparticle immune stimulator significantly reduced the feed conversion rate from 1.264 g feed per 1.0 g body weight gain in control chickens to 1.243 g feed per 1.0 g body weight gain in immune stimulator-treated chickens. |

As indicated in Table 5, microparticles having an effective average diameter of 1-10 μm were prepared by spray-drying a solution of PLGA-PEG and Pluronic® L121 block copolymer (6.5:3.5). In order to prepare the immune stimulator composition, 270 μg of the microparticles were combined with 810 μg lactose microfine powder and added to 200 μl of suspension buffer (0.1% Kolliphor® HS 15 non-ionic solubilizer and emulsifying agent, 0.001% Benzalkonium Chloride in PBS).

Figure 5:
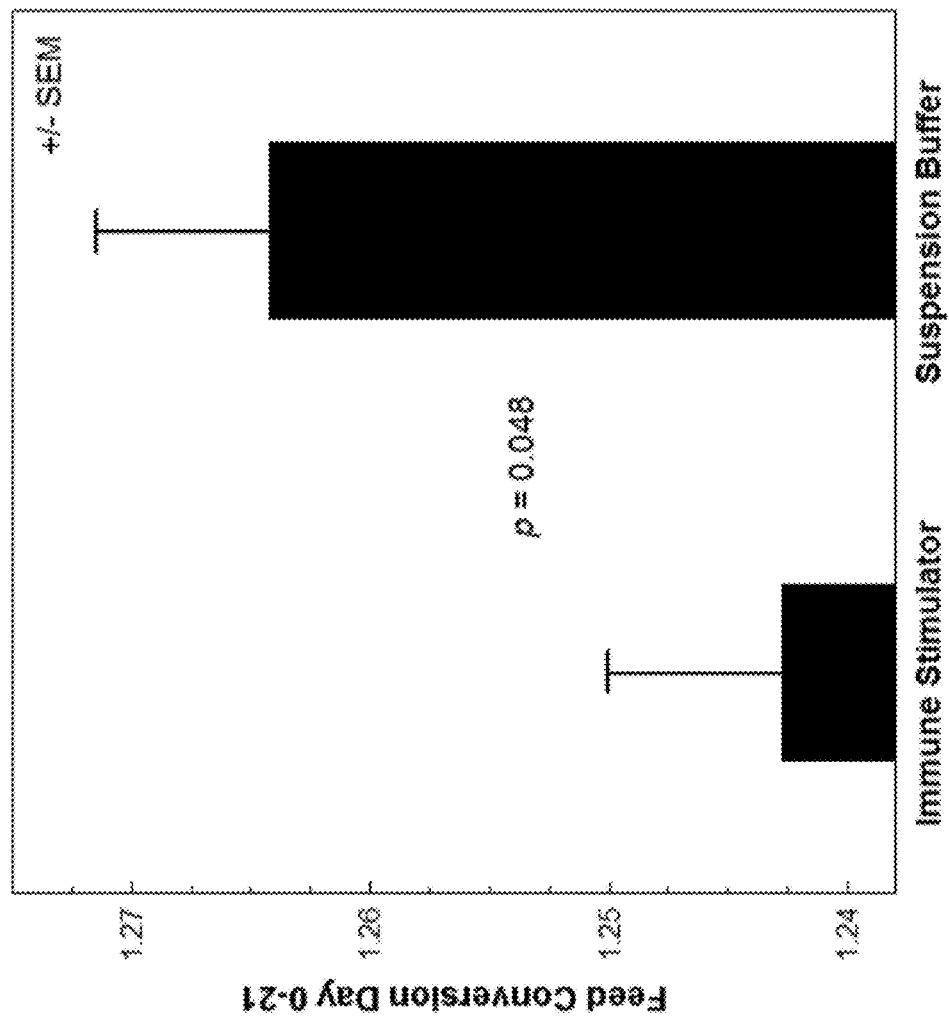
FIG. 5. Feed conversion rate from day 0 to day 21 for chickens administered immune stimulator versus buffer control.

The immune stimulator thus formulated (200 µl) was administered subcutaneously to standard broiler chickens on the day of hatching. Suspension buffer without microparticles was administered as a control. The sample size was 96 female broiler chickens each in 12 battery pens of 8 chickens fed for 3 weeks. The chickens were not challenged and feed conversion rate was assessed by measuring feed consumption per body weight (i.e., g feed required per body weight gain). The results presented in FIG. 5 illustrate that chickens administered the immune stimulator exhibited a better feed conversion rate than chickens administered the control. These results demonstrate that an immune stimulator that did not contain an antigen may be administered in order to improve feed conversion rate.

Example 6. Immune Stimulator Trial in Mice with Apoptosis Inhibitor

The ability of a composition comprising a suspension of biodegradable particles and an apoptosis inhibitor to induce an innate immune response as an "immune stimulator" and to enhance survival rate in mice was tested under the parameters of Table 6.

TABLE 6

| | |
|---|---|
| Model System | Immune Stimulator Trial in Mice: day-21 post-challenge termination survival analysis |
| Mouse strain | C3H/HeJ, 10 weeks old at start of experiment |
| Challenge | $10^8$ C. abortus elementary bodies 3 days after treatment |
| Treatment | 1× intraperitoneally (in 200 µl HBSS) & 1/10 dose intranasal (in 20 µl HBSS) |
| Carriers | 1) 8 µg nelfinavir & 3.6 µg Pluronic® L121 block copolymer |
| | 2) 8 µg nelfinavir & 3.6 µg Pluronic® L121 block copolymer + 0.16 µg Q-VD-OPH (apoptosis-inhibitor) |
| Immune Stimulator Dose | Immune stimulator delivered as a total of 12 µg composed of ~5 µm spray-dried microparticles |
| Conclusion | Inhibition of apoptosis modulates the innate immune response from non-protective to protective if a small-molecule inhibitor of apoptosis is included in an immune stimulator delivered as spray-dried nelfinavir microparticles that contain co-polymer adjuvant. This effect occurs at a single ~12 microgram total dose of the immune stimulator. |

Figure 6:
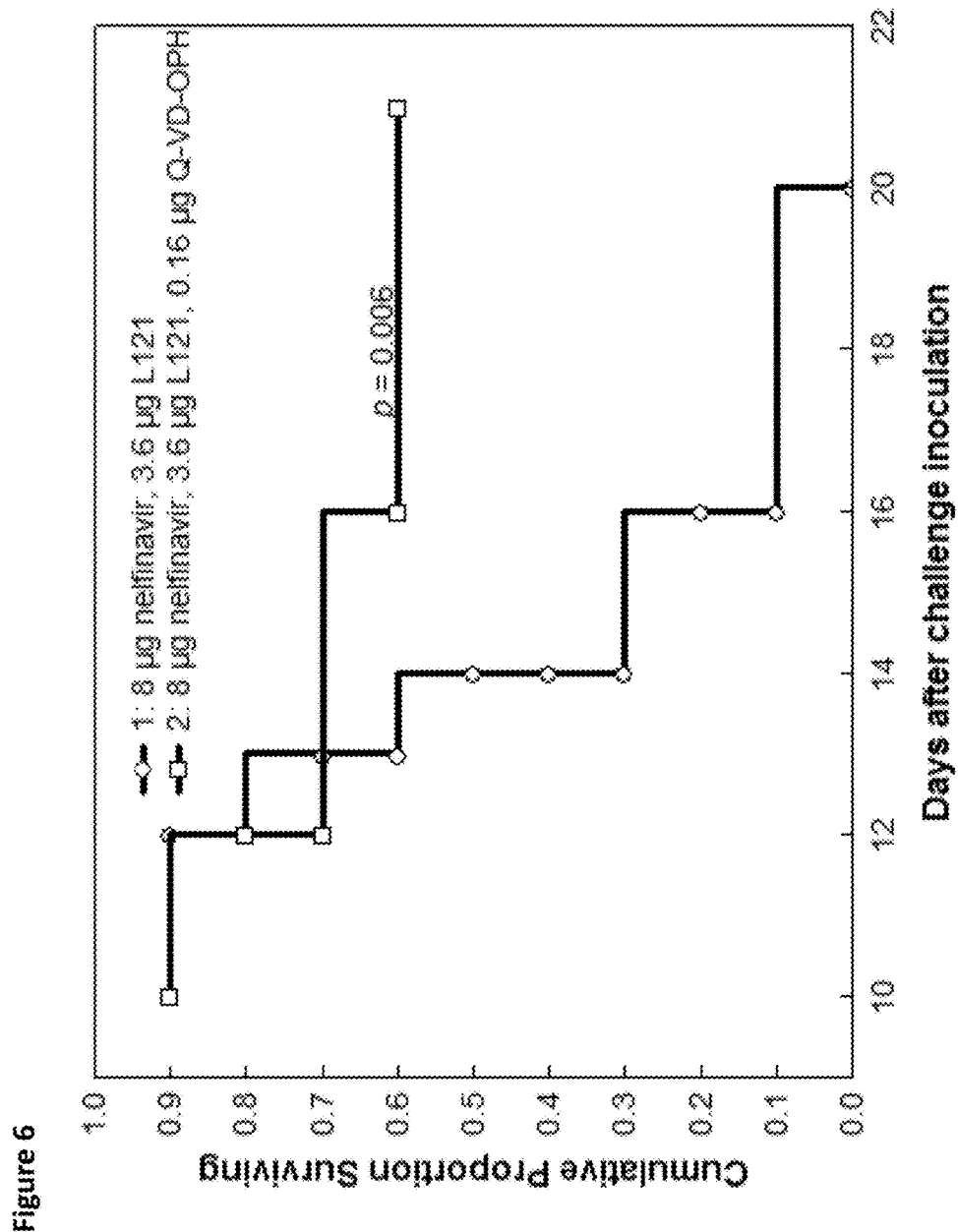
FIG. 6. Cumulative proportion surviving versus days after challenge with *C. abortus* for mice administered nelfinavir particle composition and Pluronic® L121 block copolymer, with or without apoptosis inhibitor Q-VD-OPH.

As indicated in Table 6, microparticles were prepared from nelfanivir (8 µg) combined with Pluronic® L121 block copolymer (3.6 µg) and added to HBSS (200 µl) to prepare an immune stimulator. The apoptosis inhibitor Q-VD-OPH was added (0.16 µg) to test its effect on immune stimulation. The immune stimulator was administered intraperitoneally (200 µl) and intranasally (20 µl) to C3H/HeJ which were 10 weeks old at the start of the experiment. The mice then were challenged at 3 days post-administration by administering intranasally $10^8$ C. abortus elementary bodies. The results presented in FIG. 6 illustrate that mice administered the immune stimulator comprising an apoptosis inhibitor exhibited a higher cumulative survival rate than mice administered the immune stimulator lacking an apoptosis inhibitor. These results demonstrate that apoptosis inhibitors may used to augment the effect of an immune stimulator comprising the microparticles to induce innate immunity.

Example 7. Vaccine Trial in Mice with Apoptosis Inhibitor and Antigen

The ability of a composition comprising a suspension of biodegradable particles, an apoptosis inhibitor (Q-VD-OPH or emricasan), and an antigen to induce a protective T cell response versus a non-protective/pathogenic response in mice was tested under the parameters of Table 7.

TABLE 7

| | |
|---|---|
| Model System | Vaccine Trial in Mice |
| | C. abortus respiratory challenge model, termination day-11 post-challenge. Body weight change and lung weight were analyzed on day-11 post-challenge. |
| Mouse strain | 129S6, 6 weeks old at treatment |
| Challenge | $3 \times 10^8$ C. abortus elementary bodies 6 week after treatment |
| Treatment | 1× intranasal in 20 µl suspension buffer |
| Carriers/ Controls | 1. Vaccine: 6.5 µg PLGA-PEG & 3.6 µg Pluronic® L121 block copolymer + C. abortus peptides |
| | 2. Vaccine + Apoptosis Inhibitor: 6.5 µg PLGA-PEG & 3.6 µg Pluronic® L121 block copolymer + C. abortus peptides + 0.2 µg Q-VD-OPH |
| | 3. Vaccine + Apoptosis Inhibitor: 6.5 µg PLGA-PEG & 3.6 µg Pluronic® L121 block copolymer + C. abortus peptides + 0.2 µg emricasan |
| | 4. Vaccine Carrier: 6.5 µg PLGA-PEG & 3.6 µg Pluronic® L121 block copolymer |
| | 5. Live Vaccine: low-dose C. abortus intranasal inoculation (mediates maximum protection) |
| Antigen/ Vaccine Dose | 0.2 femtoMoles of each overlapping 20-mer peptide from the 5 best protective C. abortus proteins in a total of 10 µg vaccine |
| Conclusion | Inhibition of apoptosis modulates the vaccine T cell immune response of mice from non-protective/pathogenic to protective if a small-molecule inhibitor of apoptosis is included in a vaccine delivered as spray-dried PLGA-PEG microparticles that contain co-polymer adjuvant. This effect occurs at a single ~10 microgram total dose of the vaccine. |

Figure 7:
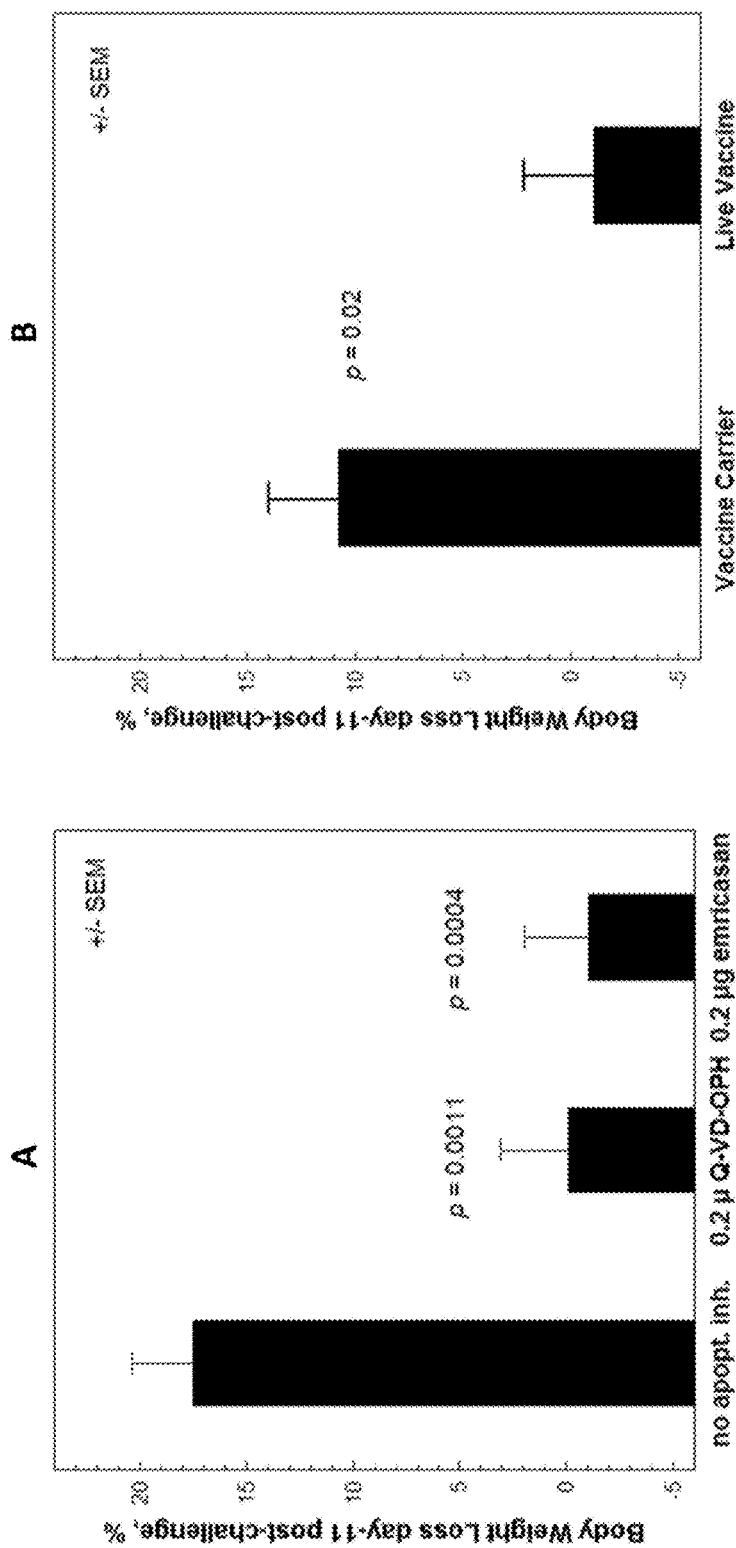
FIG. 7. A. Percent body weight loss at day 11 post-challenge for mice administered vaccine with apoptosis inhibitor Q-VD-OPH versus vaccine without apoptosis inhibitor. B. Percent body weight loss at day 11 post-challenge for mice administered vaccine carrier versus live vaccine. C. Lung weight at day 11 post-challenge for mice administered vaccine with apoptosis inhibitor Q-VD-OPH versus vaccine without apoptosis inhibitor. D. Lung weight at day 11 post-challenge for mice administered vaccine carrier versus live vaccine. E. *C. abortus*/100 mg lung, $\log_{10}$ for no apoptosis inhibition, 0.2 μg Q-VD-OPH, or 0.2 μg emricasan. F. *C. abortus*/100 mg lung, $\log_{10}$ for vaccine carrier or live vaccine.
Figure 7:
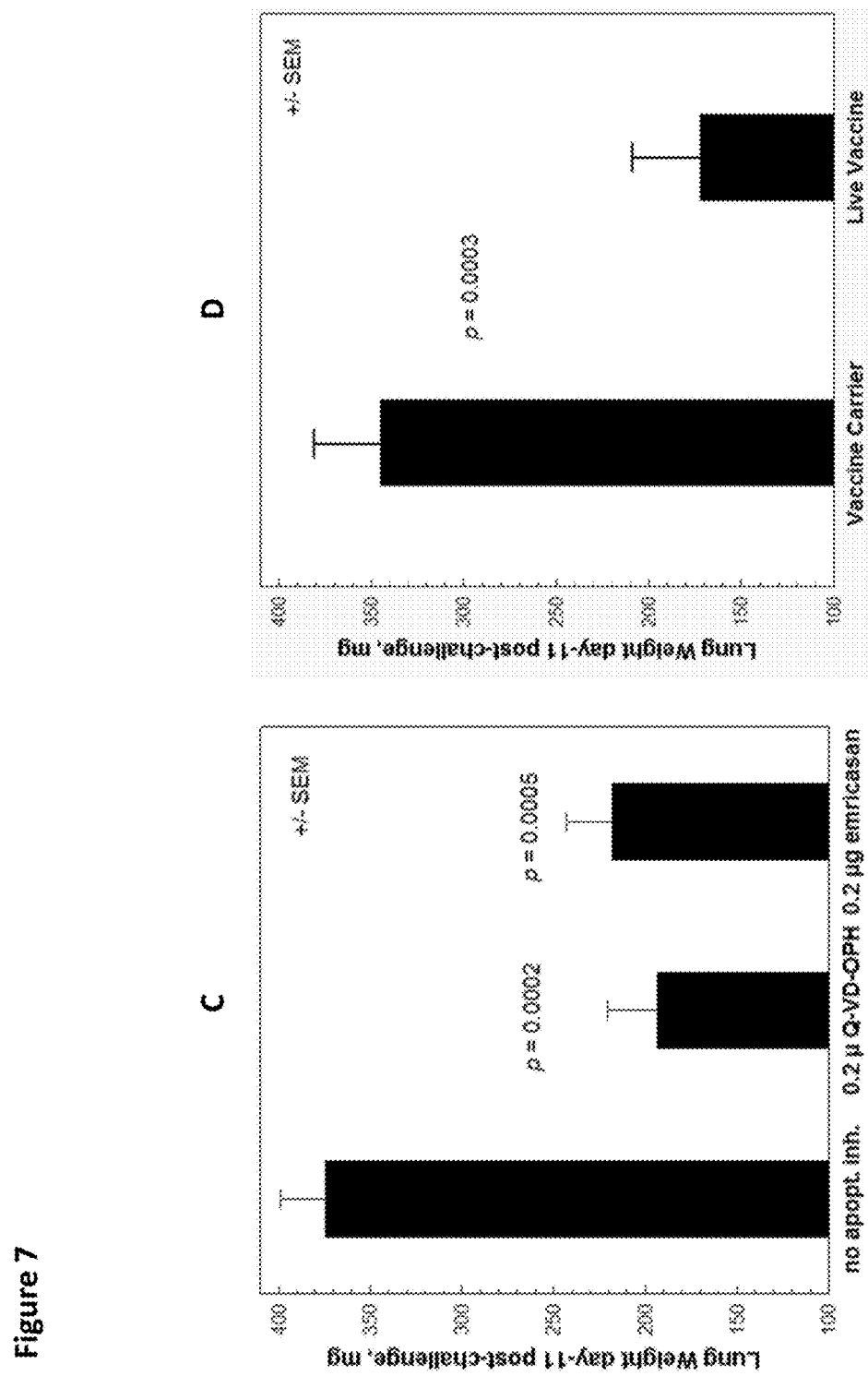
Figure 7:
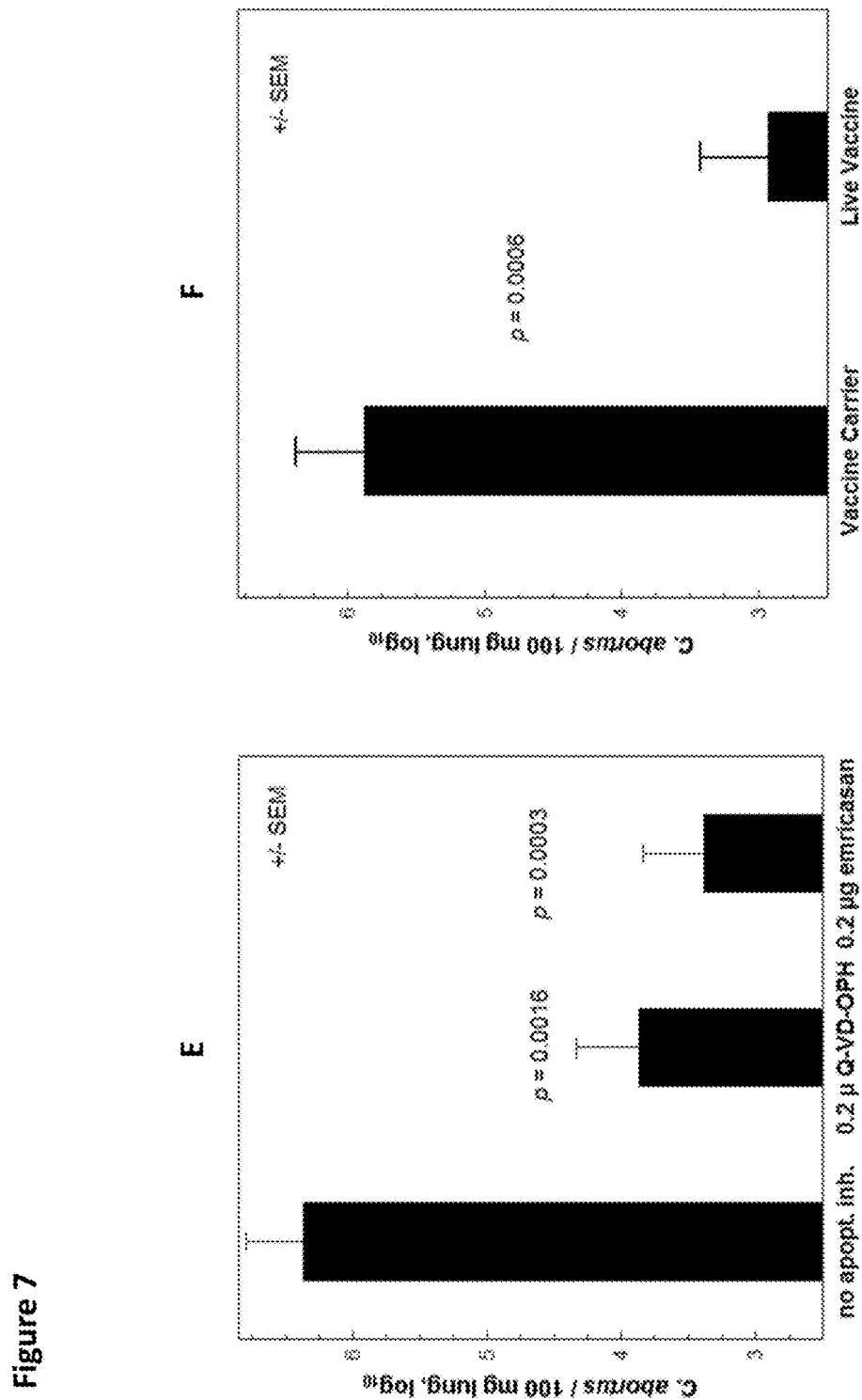

As indicated in Table 7, microparticles were prepared from PLGA-PEG (6.5 µg) and added to Pluronic® L121 block copolymer (3.6 µg) to form a microparticle composition for use as a carrier and control. (See Vaccine Carrier 4. in Table 7). A vaccine was prepared by adding C. abortus peptides to the carrier in the form of 0.2 femtoMoles of each overlapping 20-mer peptide from 5 protective C. abortus proteins (see U.S. Published Application No. 2012/0009220, the contents of which are incorporated herein by reference in their entirety) in a total of 10 µg vaccine. (See Vaccine 1. in Table 7). A vaccine composition comprising an apoptosis inhibitor also was prepared by adding 0.2 µg Q-VD-OPH (see Vaccine+Apoptosis Inhibitor 2. in Table 7) or 0.2 µg emricasan (see Vaccine+Apoptosis Inhibitor 3, Table 7). A live vaccine was utilized as a control. (See Live Vaccine 5. in Table 7). The vaccine compositions and controls were administered intranasally (20 µl) to 6 week old mice (strain 129S6). The mice were challenged at 6 weeks post-administration by administering intranasally $10^8$ C. abortus elementary bodies. The results presented in FIGS. 7A, B, C, and D illustrate that mice administered the vaccine containing the apoptosis inhibitor exhibited the lowest body weight loss and lowest lung weight gain similar to the live vaccine, suggesting that the apoptosis inhibitor modulated the T cell response from non-protective/pathogenic to protective.

Example 8. Vaccine Trial in Chickens with Apoptosis Inhibitor and Antigen

The ability of a composition comprising a suspension of biodegradable particles, an apoptosis inhibitor, and an antigen to induce a protective T cell response versus a non-protective/pathogenic response in chickens was tested under the parameters of Table 8.

TABLE 8

| | |
|---|---|
| Model | Vaccine Trial in Chickens |
| System | Infectious bursal disease virus (IBDV) respiratory challenge model, termination day-7 post-challenge. |
| Chickens | Standard broiler chickens, treatment on day of hatching |
| Challenge | IBDV suspension intranasal on 3 weeks after treatment |
| Treatment | 1× subcutaneous in 200 μl suspension buffer |
| Carriers/ Controls | 1. Vaccine: 175.5 μg PLGA-PEG & 94.5 μg Pluronic® L121 block copolymer + IBDV peptides<br>2. Vaccine + Apoptosis Inhibitor: 175.5 μg PLGA-PEG & 94.5 μg Pluronic® L121 block copolymer + IBDV peptides + 2.7, 5.4, or 10.8 μg Q-VD-OPH<br>3. Suspension buffer-treated chickens and IBDV challenge<br>4. Suspension buffer-treated chickens and no IBDV challenge (no disease) |
| Antigen/ Vaccine Dose | 0.54 femtoMoles of each overlapping 20-mer peptide from all IBDV virus proteins in a total of 270 μg microparticle vaccine, allometrically scaled 27-fold for 1,600 g target weight of chickens at 3 weeks as compared to 10 μg microparticle vaccine for 20 g mouse target weight: $(1,600/20)^{3/4} = 26.7$. |
| Conclusion | Inhibition of apoptosis modulates the vaccine T cell immune response of chickens from non-protective/pathogenic to protective if a small-molecule inhibitor of apoptosis is enclosed in a vaccine delivered as spray-dried PLGA-PEG microparticles that contain co-polymer adjuvant. This effect occurs at a single ~270 microgram total dose of the vaccine. |

As indicated in Table 8, microparticles prepared from a solution of PLGA-PEG and Pluronic® L121 block copolymer (175.5 μg: 94.5 μg) and IBDV peptides consisting of 0.54 femtoMoles of overlapping 20-mer peptides from all IBDV virus proteins. Apoptosis inhibitor Q-VD-OPH was included in amounts of 2.7, 5.4, or 10.8 μg. In order to prepare the vaccine compositions, the microparticles were added to 200 μl of suspension buffer.

Figure 8:
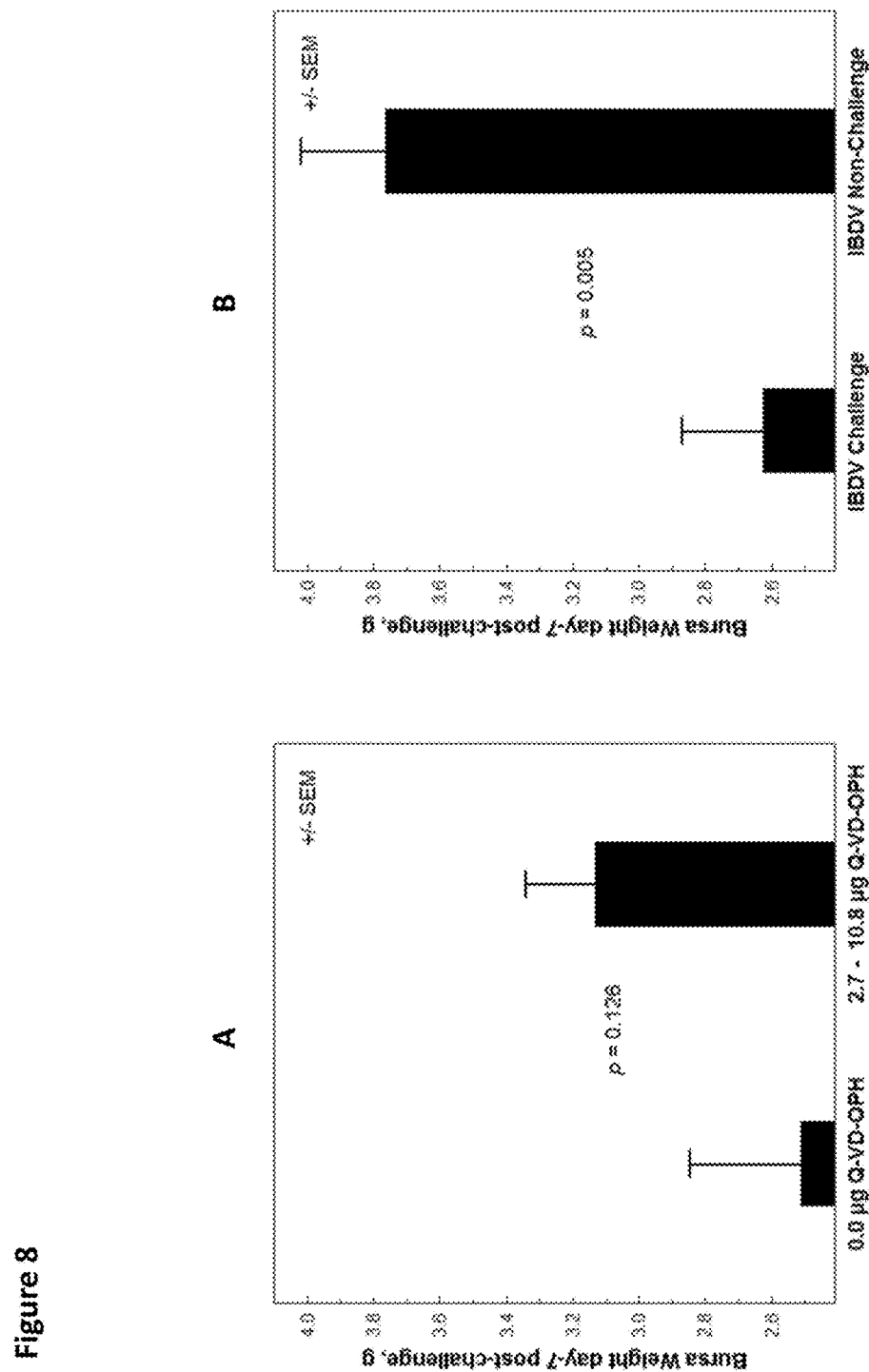
FIG. 8. A. Bursa of Fabricius weight at day 7 post-challenge with IBDV for chickens administered vaccine with apoptosis inhibitor Q-VD-OPH versus vaccine without apoptosis inhibitor. B. Bursa weight at day 7 post-challenge with IBDV for chickens administered suspension buffer control versus non-challenged chickens. C. Bursa inflammation score for challenged chickens administered vaccine with apoptosis inhibitor Q-VD-OPH versus vaccine without apoptosis inhibitor. D. Bursa inflammation score for challenged chickens administered suspension buffer control versus non-challenged chickens. E. Bursa weight at day 7 post-challenge with IBDV corrected for inflammation score for chickens administered vaccine with apoptosis inhibitor Q-VD-OPH versus vaccine without apoptosis inhibitor. F. Bursa weight at day 7 post-challenge with IBDV corrected for inflammation score for chickens administered suspension buffer control versus non-challenged chickens. G. Percent disease protection for chickens administered vaccine with apoptosis inhibitor Q-VD-OPH versus vaccine without apoptosis inhibitor. H. Percent disease protection for chickens administered suspension buffer control versus non-challenged chickens.
Figure 8:
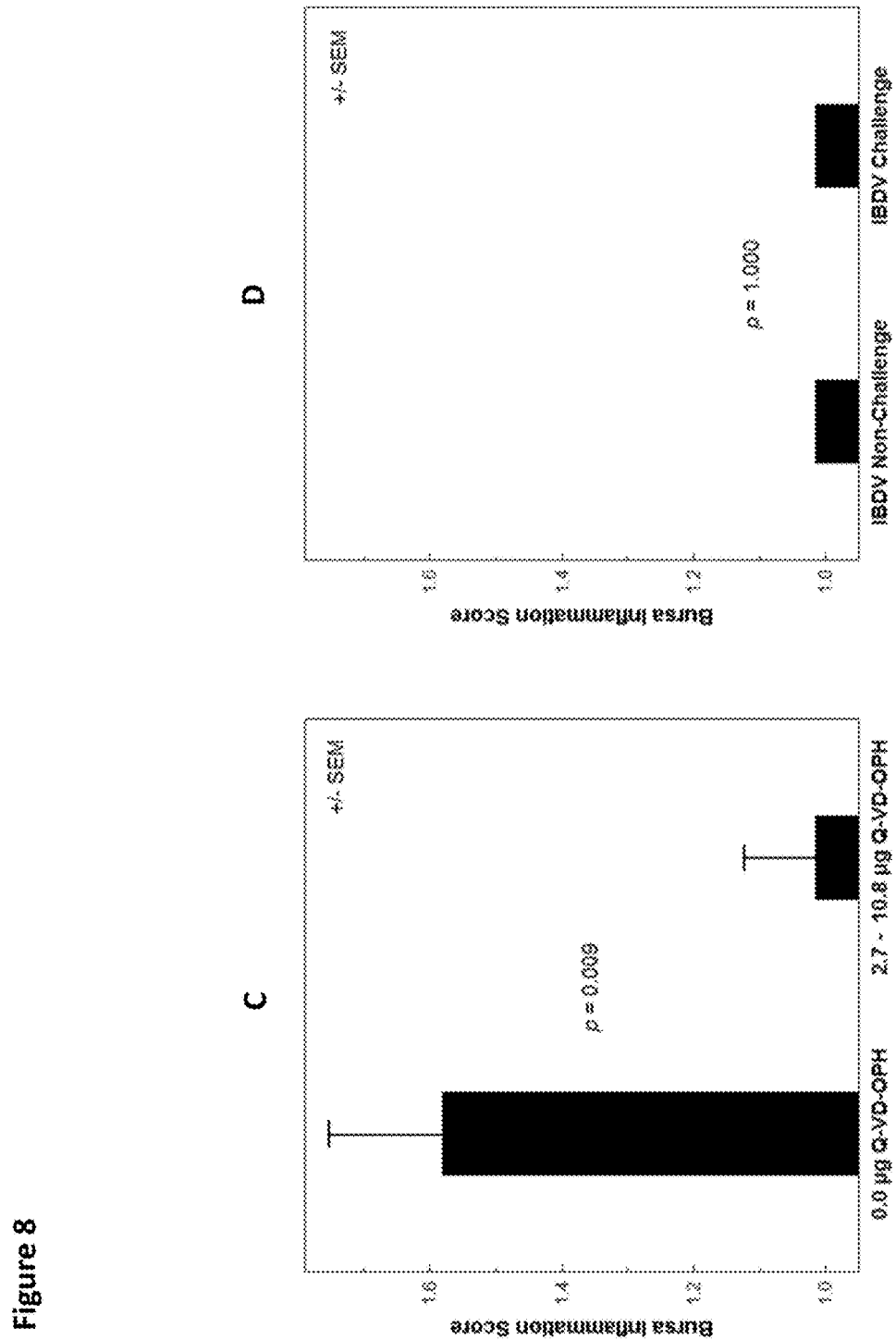
Figure 8:
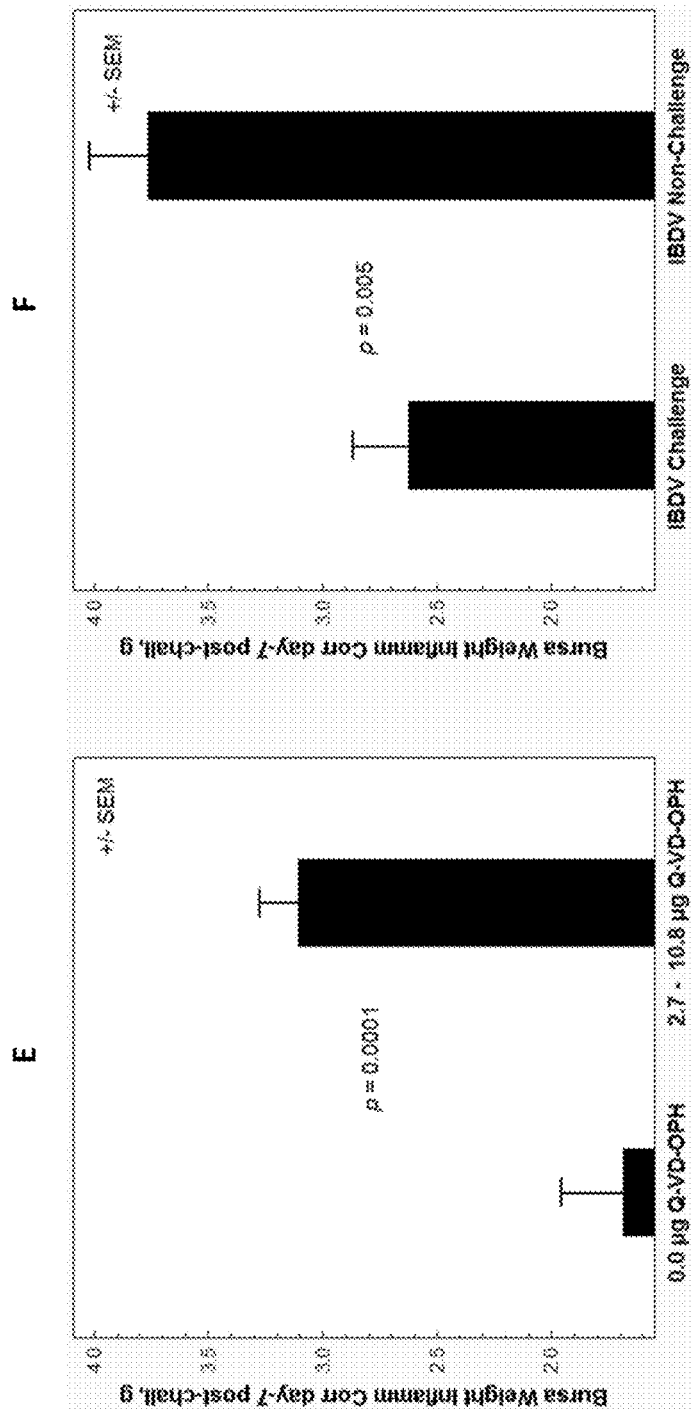

The vaccine compositions and control were administered subcutaneously to standard broiler chickens on the day of hatching. Suspension buffer alone was administered as a control. The chickens were challenged three weeks post-administration by administering IBDV. The weight and inflammation of Bursa of Fabricius were analyzed on day-7 post-challenge, where IBDV selectively targets B cells in the Bursa of Fabricius of chickens, leading to inflammation followed by atrophy. This reduces the weight of the Bursa after the inflammation has subsided. Inflammation was scored on a scale of 1-4, and the increase of bursa weight caused by inflammation was corrected by dividing bursa weight with the inflammation score. The results presented in FIGS. 8A, B, C, D, E, F, G, and H suggest that the apoptosis inhibitor modulated the T cell response from non-protective/pathogenic to protective in immunized chickens challenged with IBDV.

Example 9. Vaccine Experiment in Mice

The ability of a composition comprising a suspension of biodegradable particles comprising nelfinavir and an antigen to induce a protective T cell response in mice was tested under the parameters of Table 9.

TABLE 9

| | |
|---|---|
| Vaccine Experiment in Mice | |
| Model System | Vaccine Experiment in Mice: day-21 post-challenge termination survival analysis |
| Mouse strain | C3H/HeJ, 6 weeks old at start of experiment |
| Challenge | $10^8$ C. abortus elementary bodies 4 weeks after 3rd vaccination |

TABLE 9-continued

| | |
|---|---|
| Vaccine Experiment in Mice | |
| Vaccination | 3× in 4-week interval subcutaneously between shoulders |
| Antigen Dose | 0.1 femtoMole each peptide (0.22 pg each peptide) per mouse |
| Vaccine Carrier | 2 mg nelfinavir & 50 μg Poly (I:C) in 200 μl HBSS = antigen delivery as 1-20 μm microparticles of precipitated and grinded nelfinavir with co-precipitated Poly (I:C) adjuvant and peptide antigens |
| Conclusion | Effective low-antigen dose vaccination can utilize different adjuvants and different microparticle delivery modalities. |

Figure 9:
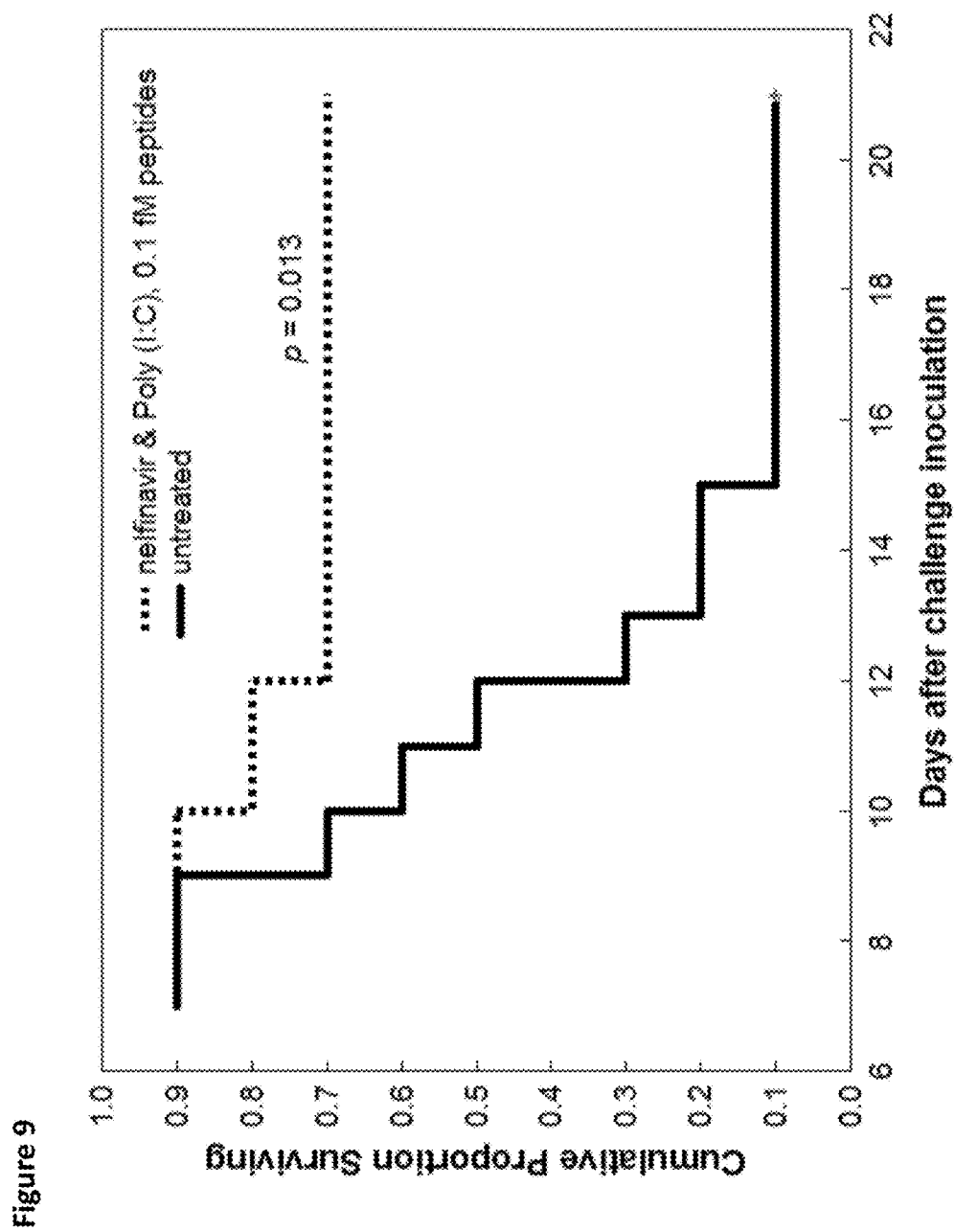
FIG. 9. Cumulative proportion surviving versus days after challenge with *C. abortus* for mice administered nelfinavir particle composition, Poly (I:C), and 1 fmole *C. abortus* peptides versus untreated.

As indicated in Table 9, microparticles having an effective diameter of (1-20 μm) were prepared by grinding nelfinavir, which is a very poorly water soluble HIV protease inhibitor with that has an immunopotentiating effect. The ground nelfinavir particles were co-precipitated with 50 μg Poly (I:C) and peptide antigens in the form of 0.1 femtoMoles of each overlapping 20-mer peptide from 5 C. abortus proteins shown to be protective against infection (see U.S. Published Application No. 2012/0009220, the contents of which are incorporated herein by reference in their entirety). The co-precipitated particles were added to 200 μl HBSS to form a vaccine composition. The vaccine compositions and control (200 μl HBSS) were administered subcutaneously between the shoulders of 6 week old mice (strain C3H/HeJ) for three times in four week intervals post-vaccination. The mice were challenged at 4 weeks after the third vaccination by administering intranasally $10^8$ C. abortus elementary bodies and the cumulative proportion of surviving mice was assessed. As indicated in FIG. 9, vaccinated mice exhibited ~70% cumulative survival while control mice exhibited ~10% cumulative survival.

Example 10. Vaccine Experiment in Mice

The ability of a composition comprising a suspension of biodegradable particles comprising nelfinavir and an antigen to induce a protective T cell response in mice was tested under the parameters of Table 10.

| | |
|---|---|
| Model System | Vaccine Experiment: day-21 post-challenge termination survival analysis |
| Mouse strain | C3H/HeJ, 6 weeks old at start of experiment |
| Challenge | $10^8$ C. abortus elementary bodies 6 weeks after vaccine |
| Vaccination | 1× subcutaneously between shoulders |
| Antigen Dose | 1 femtoMole each peptide (2.2 pg each peptide) per mouse |
| Vaccine Carrier | 5 mg nelfinavir & 0.25 mg Pluronic® L121 block copolymer in 200 μlHBSS = antigen delivery as 1-10 μm spray-dried microparticles |
| Conclusion | Effective low-antigen dose vaccination by microparticle delivery can utilize single vaccination of spray-dried preparations using nelfinavir as carrier and co-polymer as adjuvant. |

Figure 10:
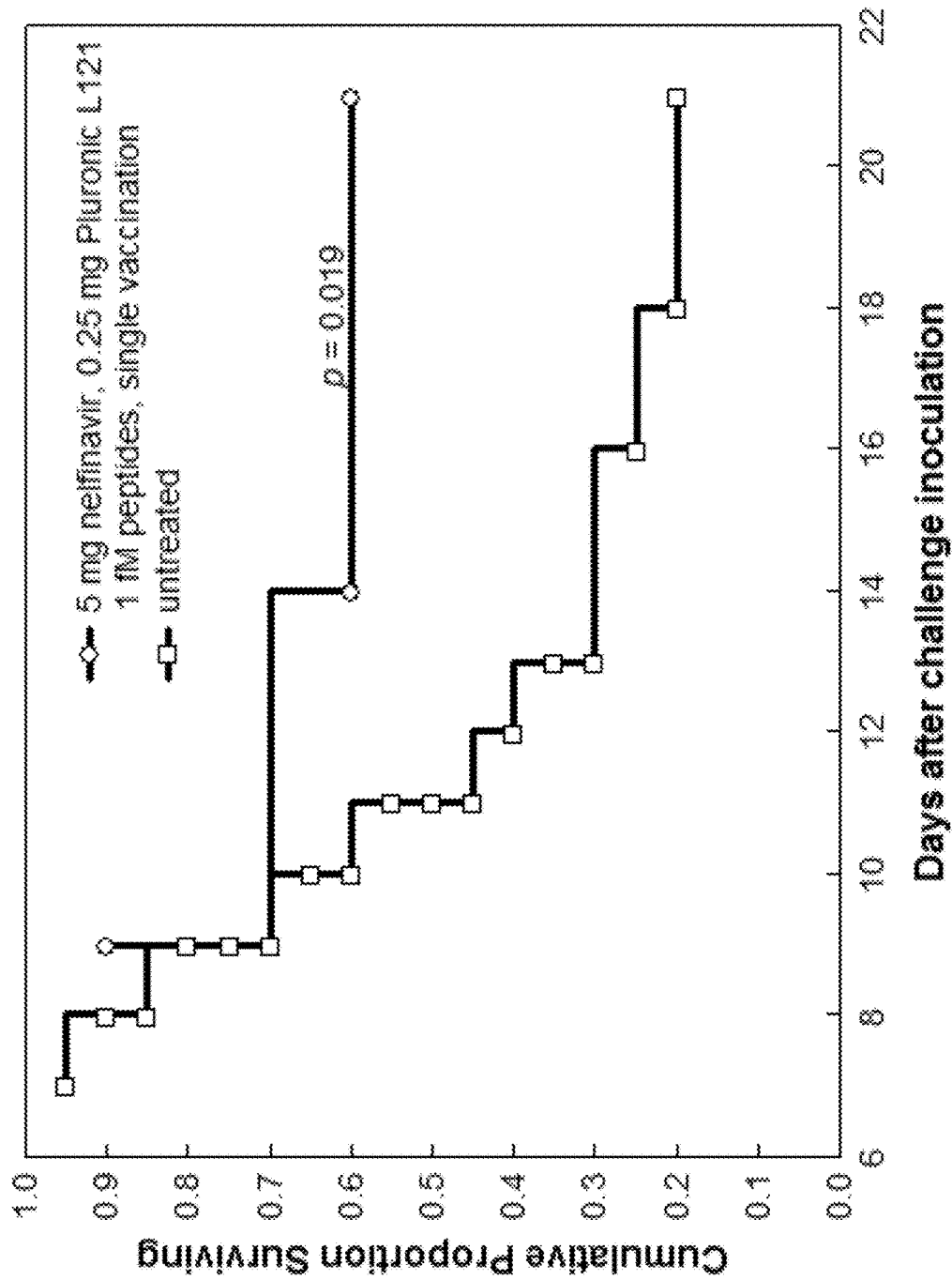
FIG. 10. Cumulative proportion surviving versus days after challenge with *C. abortus* for mice administered nelfinavir particle composition, Pluronic® L121 block copolymer, and 1 fmole *C. abortus* peptides versus untreated.

As indicated in Table 10, microparticles having an effective diameter of (1-10 μm) were prepared by spray-drying nelfinavir (5 mg) and Pluronic® L121 block copolymer (0.25 mg). The microparticles were administered with peptide antigens in the form of 1.0 femtoMoles of each overlapping 20-mer peptide from 5 C. abortus proteins shown to be protective against infection (see U.S. Published Application No. 2012/0009220, the contents of which are incorporated herein by reference in their entirety) in 200 μl HBSS. The vaccine compositions and control (200 μl HBSS) were administered subcutaneously between the shoulders of 6 week old mice (strain C3H/HeJ). The mice were challenged at 6 weeks post-vaccination by administering intranasally $10^8$ *C. abortus* elementary bodies and the cumulative proportion of surviving mice was assessed. As indicated in FIG. 10, vaccinated mice exhibited ~60% cumulative survival while un-treated mice exhibited ~20% cumulative survival.

Example 11. Vaccine Trial in Mice

The ability of a composition comprising a suspension of biodegradable particles, a co-polymer adjuvant, and an antigen to induce a protective T cell response in mice was tested under the parameters of Table 11.

TABLE 11

| | |
|---|---|
| Model System | Vaccine Trial in Mice<br>*C. abortus* respiratory challenge model, termination day-11 post-challenge.<br>Analyze body weight change and lung weight on day-11 post-challenge, body weight change (loss) from day 2- day-11 post-challenge. |
| Mouse strain | 129S6, 6 weeks old at treatment |
| Challenge | $3 \times 10^8$ *C. abortus* elementary bodies 6 week after treatment |
| Treatment | 1× subcutaneous in 200 µl suspension buffer |
| Carriers/ Controls | 1. Low peptide vaccines: 6.5 µg PLGA-PEG & 3.6 µg Pluronic ® L121 block copolymer + 0.02 or 0.2 fM *C. abortus* peptides<br>2. High peptide vaccine: 6.5 µg PLGA-PEG & 3.6 µg Pluronic ® L121 block copolymer + 2.0 fM *C. abortus* peptides<br>3. Vaccine carrier: 6.5 µg PLGA-PEG & 3.6 µg Pluronic ® L121 block copolymer<br>4. Live vaccine: low-dose *C. abortus* intranasal inoculation (mediates maximum protection) |
| Antigen/ Vaccine e Dos | 0.0, 0.02, 0.2, or 2.0 femtoMoles of each overlapping 20-mer peptide from the 5 best protective *C. abortus* proteins in a total of 10 µg vaccine composed of microparticles having an average effective diameter of ~2 µm |
| Conclusion | Effective low-antigen dose vaccination is possible with a single 10 µg spray-dried microparticle vaccination using PLGA-PEG as a carrier and a co-polymer as adjuvant. Increasing the peptide antigen dose from 0.02 or 0.2 fM to 2.0 fM modulates the vaccine T cell immune response of mice from non-protective/pathogenic to protective. |

Vaccine compositions were prepared by combining microparticles of PLGA-PEG (6.5 µg), Pluronic® L121 block copolymer (3.5 µg) as a co-polymer adjuvant, peptides 0.0, 0.02, 0.2, or 2.0 femtoMoles of each overlapping 20-mer peptide from 5 *C. abortus* proteins shown to be protective against infection (see U.S. Published Application No. 2012/0009220, the contents of which are incorporated herein by reference in their entirety), in 200 µl suspension buffer.

Figure 11:
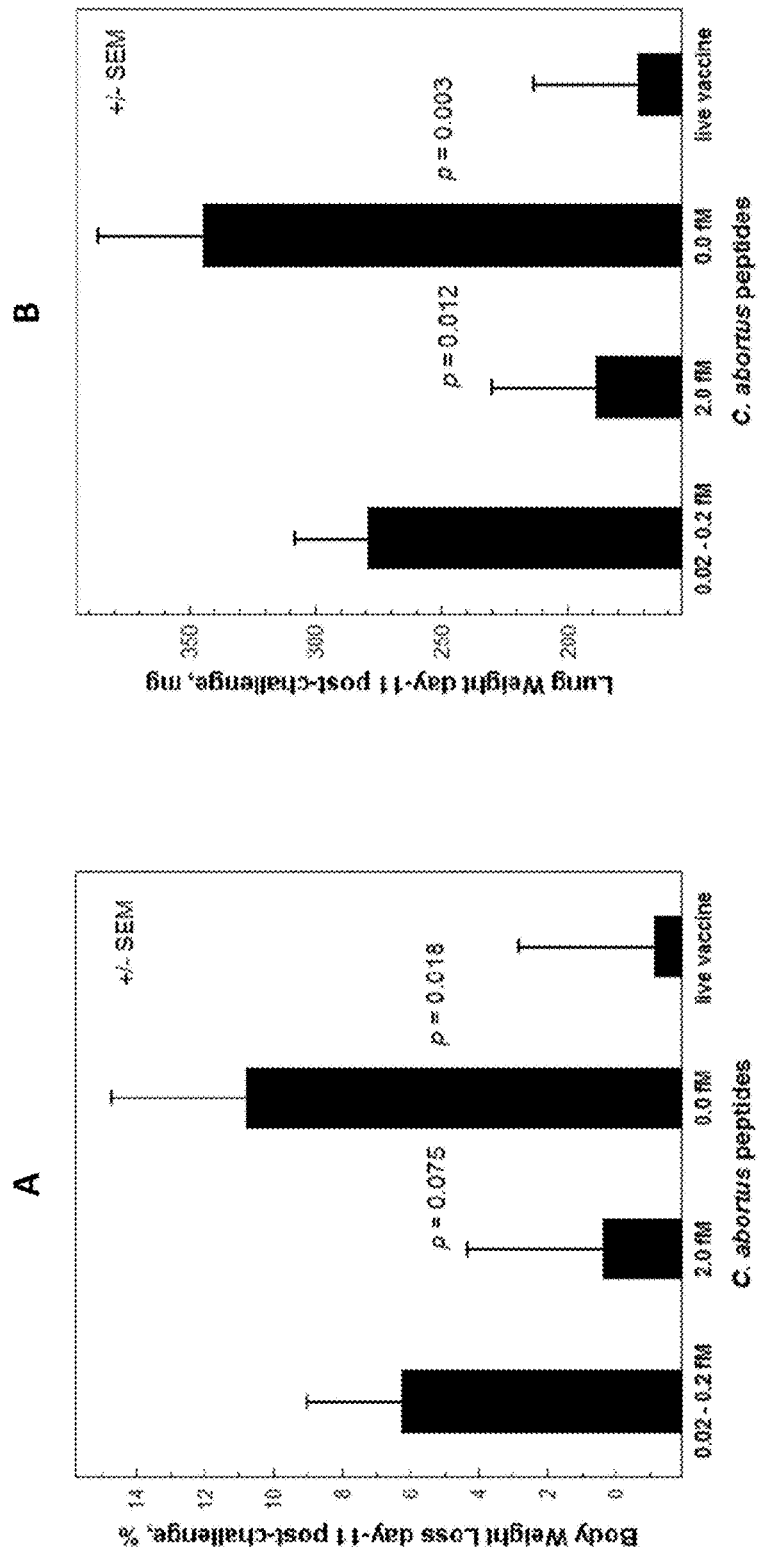
FIG. 11. A. Percent body weight loss at day 11 post-challenge for mice administered vaccine comprising 0.0, 0.02-0.2, or 2.0 femtomoles overlapping peptides from 5 protective proteins of *C. abortus* and live vaccine. B. Lung weight at day 11 post-challenged for mice administered vaccine comprising 0.0, 0.02-0.2, or 2.0 femtomoles overlapping peptides from 5 protective proteins of *C. abortus* and live vaccine. C. *C abortus* loads for mice administered vaccine comprising 0.0, 0.02-0.2, or 2.0 femtomoles overlapping peptides from 5 protective proteins of *C. abortus* and live vaccine. D. Percent body weight loss versus days post-challenge for mice administered vaccine comprising 0.02-0.2 or 2.0 femtomoles overlapping peptides from 5 protective proteins of *C. abortus*. E. Percent body weight loss versus days post-challenge for mice administered vaccine comprising 0.0 or 0.02-0.2 femtomoles overlapping peptides from 5 protective proteins of *C. abortus*. F. Percent body weight loss versus days post-challenge for mice administered vaccine comprising 0.0 or 2.0 femtomoles overlapping peptides from 5 protective proteins of *C. abortus*. G. Percent body weight loss versus days post-challenge for mice administered vaccine comprising 0.0 femtomoles overlapping peptides from 5 protective proteins of *C. abortus* and live vaccine.
Figure 11:
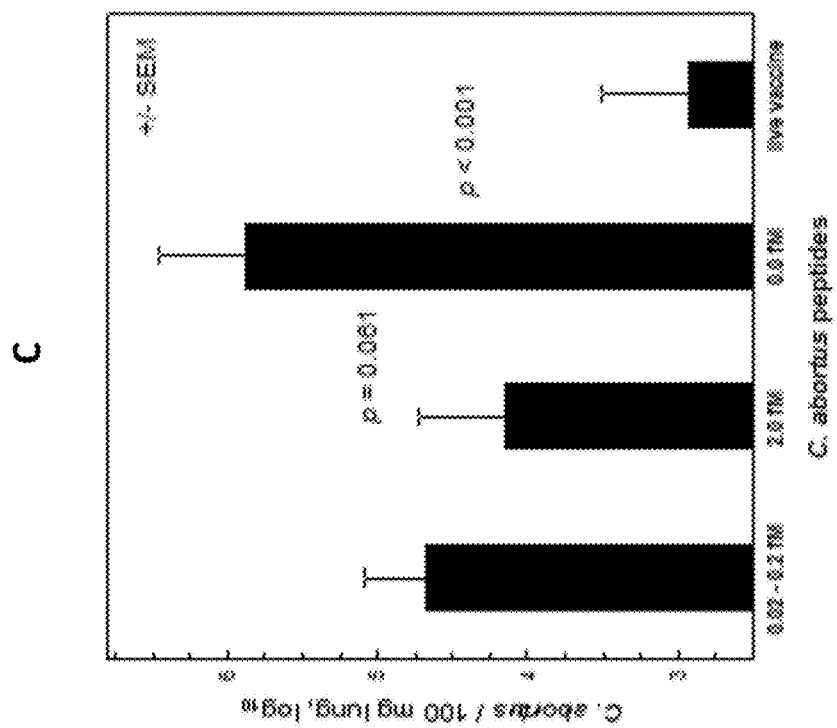
Figure 11:
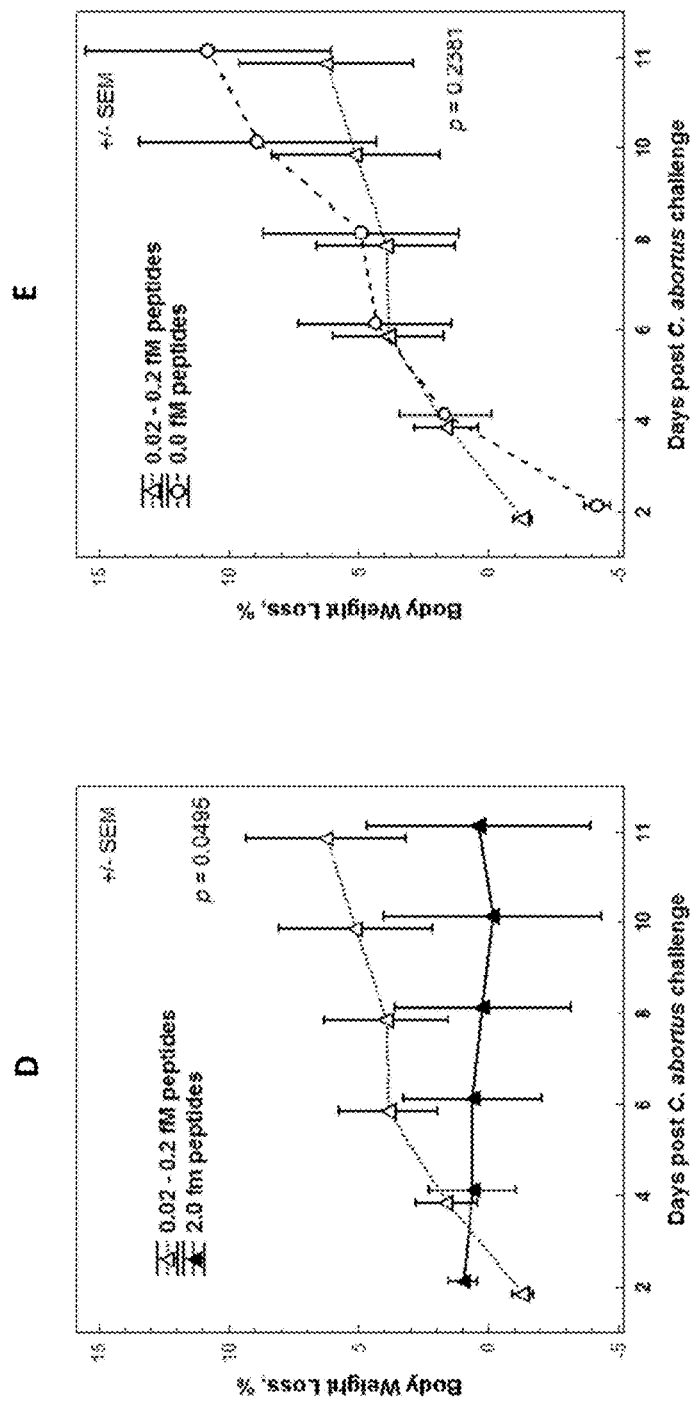
Figure 11:
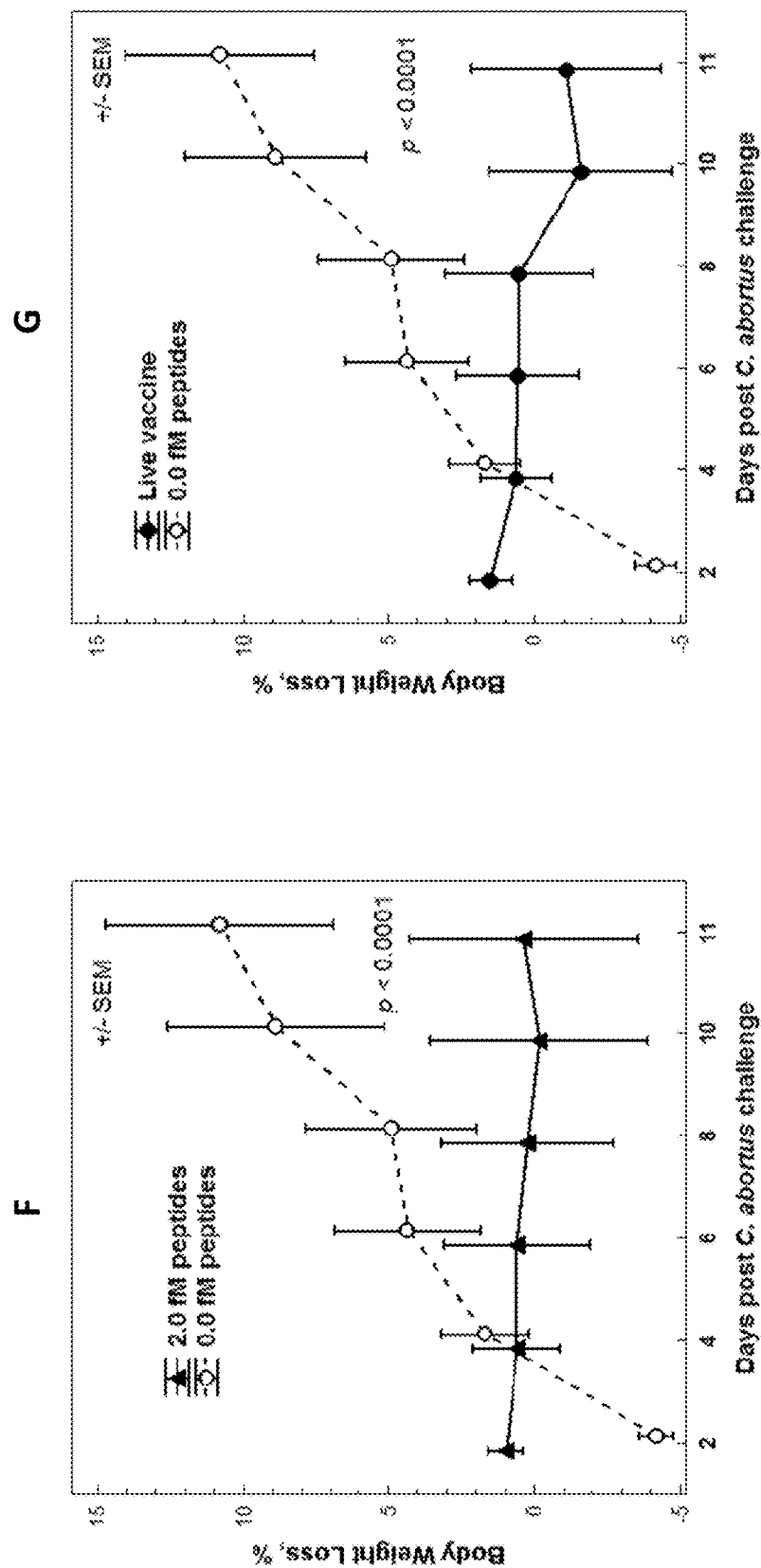

The vaccine compositions and controls (0.0 femtoMoles peptides and live vaccine) were administered subcutaneously between the shoulders of 6 week old mice (strain 129S6). The mice were challenged at 6 weeks post-vaccination by administering intranasally $10^8$ *C. abortus* elementary bodies and the body weight loss an lung weight gain were assessed. The results presented in FIGS. 11A, B, C, D, E, F, and G illustrate that mice administered the vaccine containing 2.0 femtoMoles peptides exhibited the lowest body weight loss, lowest *Chlamydia* loads, and lowest lung weight gain similar to the live vaccine, suggesting that a dose of 2.0 femtoMoles peptides modulated the T cell response from non-protective/pathogenic to protective.

Example 12. Vaccine Trial in Chickens

The ability of a composition comprising a suspension of biodegradable particles, a co-polymer adjuvant, and an antigen to induce a protective T cell response in chickens was tested under the parameters of Table 12.

TABLE 12

| | |
|---|---|
| Model System | Vaccine Trial in Chickens<br>Infectious bursal disease virus (IBDV) respiratory challenge model, termination day-7 post-challenge.<br>Analyze weight and inflammation of Bursa of Fabricius on day-7 post-challenge. |
| Chickens | Standard broiler chickens, treatment on day of hatching |
| Challenge | IBDV suspension intranasal on 3 weeks after treatment |
| Treatment | 1× subcutaneous in 200 µl suspension buffer |
| Vaccines/ Controls | 1. Low Peptide Vaccine: 175.5 µg PLGA-PEG & 94.5 µg Pluronic ® L121 block copolymer + 0.54 fmoles each IBDV peptide<br>2. High Peptide Vaccines: 175.5 µg PLGA-PEG & 94.5 µg Pluronic ® L121 block copolymer + 3.82 or 27.0 or 191.2 fmoles each IBDV peptide<br>3. Suspension buffer-treated chickens and IBDV challenge<br>4. Suspension buffer-treated chickens and no IBDV challenge (no disease) |
| Vaccine Dose | Overlapping 20-mer peptides from all IBDV virus proteins in a total of 270 µg microparticle vaccine, allometrically scaled 27-fold for 1,600 g target weight of chickens at 3 weeks as compared to 10 µg microparticle vaccine for 20 g mouse target weight: $(1,600/20)^{3/4} = 26.7$. |
| Conclusion | Increase of peptide antigen dose at a single ~270 microgram total vaccine dose modulates the vaccine T cell immune response of chickens from non-protective/pathogenic to protective in a vaccine delivered as spray-dried PLGA-PEG microparticles that contain co-polymer adjuvant. |

As indicated in Table 12, microparticles prepared from a solution of PLGA-PEG and Pluronic® L121 block copolymer (175.5 µg: 94.5 µg) and IBDV peptides consisting of 0.54, 3.82, 27.0, or 191.2 femtoMoles of overlapping 20-mer peptides from all IBDV virus proteins. In order to prepare the vaccine compositions, the microparticles were added to 200 µl of suspension buffer.

Figure 12:
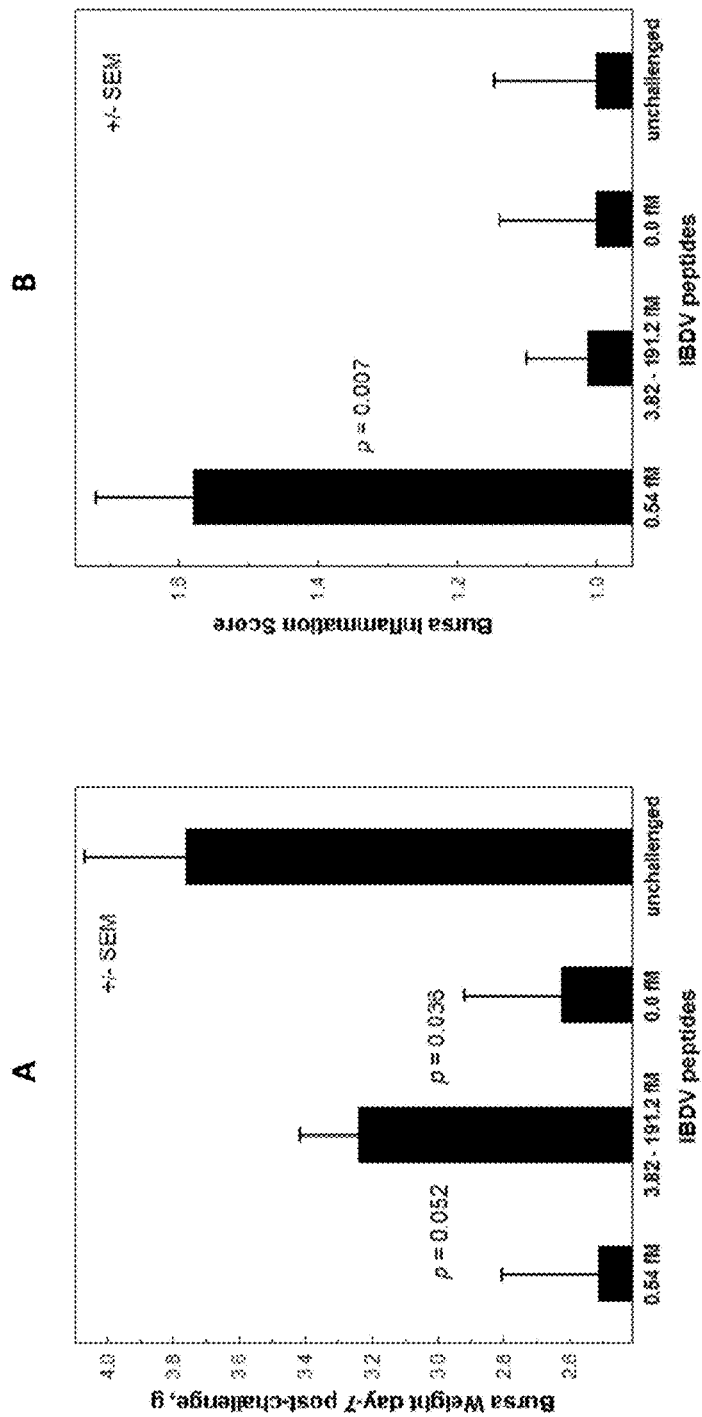
FIG. 12. A. Bursa of Fabricius weight at day 7 post-challenge for chickens administered vaccine comprising 0.0, 0.54, or 3.82-191.2 fmoles IBDV peptides versus unchallenged chickens. B. Bursa inflammation score at day 7 post-challenge for chickens administered vaccine comprising 0.0, 0.54, or 3.82-191.2 fmoles IBDV peptides versus unchallenged chickens. C. Bursa weight at day 7 post-challenge with IBDV corrected for inflammation score for chickens administered vaccine comprising 0.0, 0.54, or 3.82-191.2 fmoles IBDV peptides versus unchallenged chickens. D. Percent disease protection for chickens administered vaccine comprising 0.0, 0.54, or 3.82-191.2 fmoles IBDV peptides versus unchallenged chickens.
Figure 12:
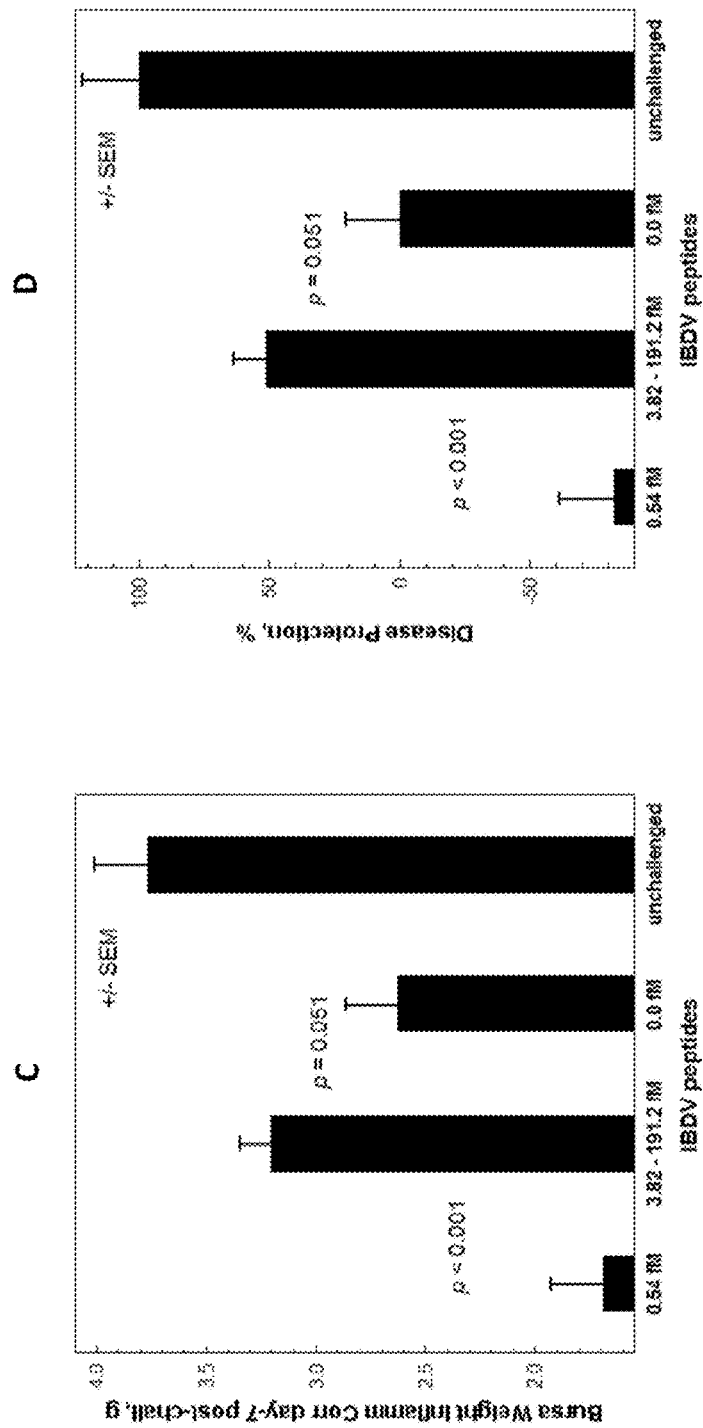

The vaccine compositions and control were administered subcutaneously to standard broiler chickens on the day of hatching. The chickens were challenged three weeks post-administration by administering IBDV. The weight and inflammation of Bursa of Fabricius were analyzed on day-7 post-challenge Inflammation was scored on a scale of 1-4, and the increase of bursa weight caused by inflammation was corrected by dividing bursa weight with the inflammation score. The results presented in FIGS. 12A, B, C, and D suggest that a doses of 3.82-191.2 femtomoles (versus a dose of 0.54 femtomoles) modulated the T cell response from non-protective/pathogenic to protective in immunized chickens challenged with IBDV.

Example 13. Vaccine Trial in Mice

The ability of a composition comprising a suspension of biodegradable particles, a co-polymer adjuvant, and an antigen to induce a protective T cell response in mice was tested under the parameters of Table 13.

TABLE 13

| | |
|---|---|
| Model | Vaccine Trial in Mice |
| System | C. abortus respiratory challenge model, termination day-11 post-challenge. Analyze body weight change and lung weight on day-11 post-challenge. |
| Mouse strain | 129S6, 6 weeks old at treatment |
| Challenge | $3 \times 10^8$ C. abortus elementary bodies 6 week after treatment |
| Treatment | 1× subcutaneous in 200 μl suspension buffer |
| Carriers/ Controls | 1. Vaccine: 6.5 μg PLA L206S & 3.6 μg Pluronic® L121 block copolymer + C. abortus peptides<br>2. Vaccine Carrier: 6.5 μg PLA L206S & 3.6 μg Pluronic® L121 block copolymer<br>3. Live Vaccine: low-dose C. abortus intranasal inoculation (mediates maximum protection) |
| Antigen/ Vaccine Dose | 2.0 femtoMoles of each overlapping 20-mer peptide from the 5 best protective C. abortus proteins in a total of 10 μg vaccine composed of ~2 μm microparticles |
| Conclusion | Different polymers are affective as carriers for a vaccine delivered as spray-dried polymer microparticles that contain co-polymer adjuvant. This effect occurs at a single ~10 microgram total dose of the vaccine. |

Figure 13:
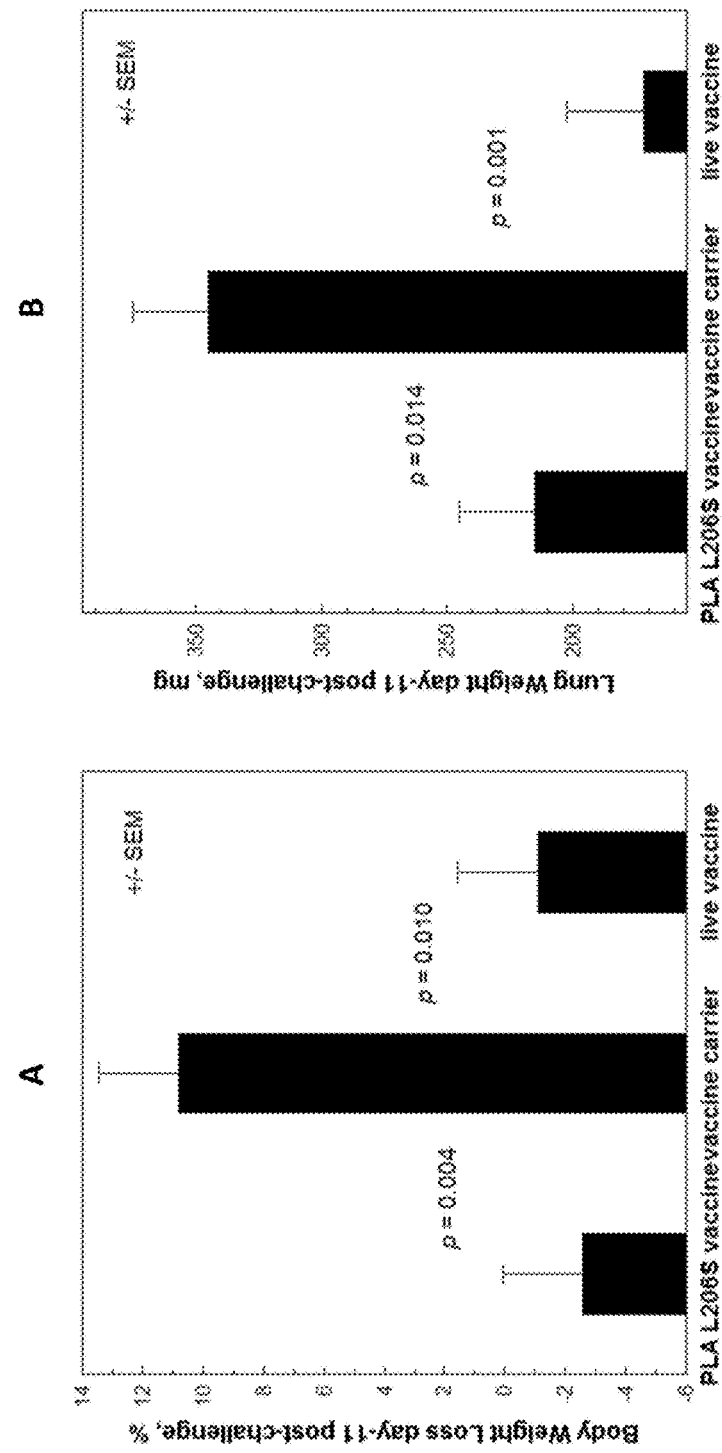
FIG. 13. A. Percent body weight loss at day 11 post-challenge for mice administered vaccine comprising 2.0 femtomoles overlapping peptides from 5 protective proteins of *C. abortus* and live vaccine. B. Lung weight at day 11 post-challenged for mice administered vaccine comprising 2.0 femtomoles overlapping peptides from 5 protective proteins of *C. abortus* and live vaccine. C. *C abortus* loads for mice administered vaccine comprising 2.0 femtomoles overlapping peptides from 5 protective proteins of *C. abortus* and live vaccine. D. Percent body weight loss versus days post-challenge for mice administered vaccine comprising 2.0 femtomoles overlapping peptides from 5 protective proteins of *C. abortus* and live vaccine.
Figure 13:
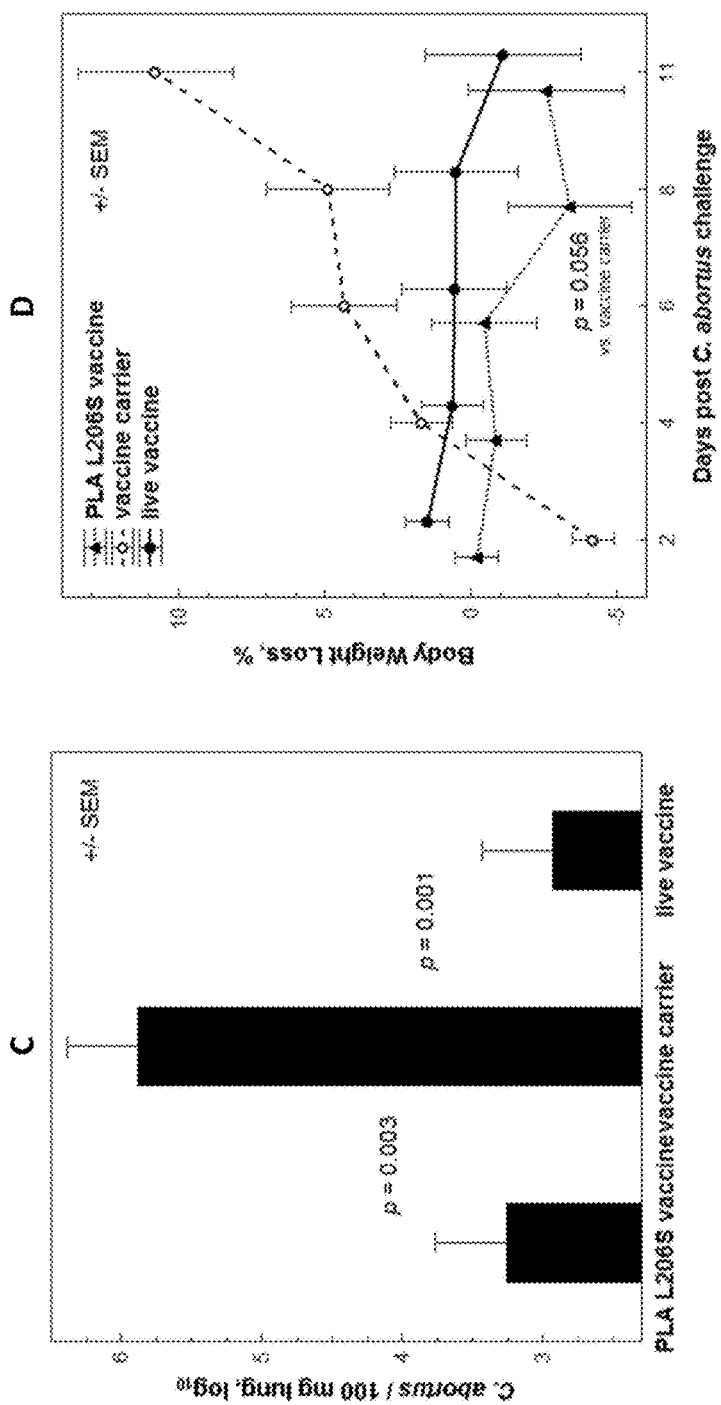

As indicated in Table 13, microparticles were prepared from PLGA L206S (6.5 μg) and added to Pluronic® L121 block copolymer (3.6 μg) together with 2.0 femtomoles of each overlapping 20-mer peptide from 5 protective C. abortus proteins (see U.S. Published Application No. 2012/0009220, the contents of which are incorporated herein by reference in their entirety) in a total of 10 μg to form a vaccine. (See Vaccine 1. In Table 13). Microparticles also were prepared from PLGA-PEG (6.5 μg) and added to Pluronic® L121 block copolymer (3.6 μg) to form a carrier as a control. (See Vaccine Carrier 2. In Table 13). A live vaccine was utilized as a control. (See Live Vaccine 3, Table 13). The vaccine compositions and controls were administered intranasally (20 μl) to 6 week old mice (strain 129S6). The mice were challenged at 6 weeks post-administration by administering intranasally $10^8$ C. abortus elementary bodies. The results presented in FIGS. 13A, B, C, and D illustrate that mice administered the vaccine containing the 2.0 femtomoles exhibited a low body weight loss, a low lung weight gain, a low C. abortus load, and a low percent body weight loss versus day after challenge, similar to the live vaccine.

Example 14. Size of the Polymeric Particles

Optimal Size of Microparticles for Vaccine Delivery.

Size is considered to be one of the crucial parameter affecting the immunogenicity of microparticles, since smaller particles (<10 μm) has been found significantly more immunogenic than larger ones (Eldridge et al., 1991; O'Hagan et al., 1993). When PLG particles of 1-10 μm diameter (mean of 3.5 μm) were compared to 10-110 μm particles (mean of 54.5 μm) with encapsulated staphylococcal enterotoxin B, the generation of serum IgG antitoxin response was more rapid and substantially more vigorous with the smaller particles (Eldridge et al., 1991). Similarly, with ovalbumin (OVA) entrapped in PLA particles, an increased serum anti-OVA antibody titer was observed with particles<5 μm compared to particles with mean sizes larger than 5 μm (Nakaoka et al., 1996). The effect of particle size on immunogenicity is likely to be a consequence of enhanced uptake of smaller-sized particles into lymphatics and greater uptake into APC. An earlier study demonstrated that only microspheres<5 μm were transported to the spleen after oral administration in mice (Tabata et al., 1996). Recently, it has been demonstrated that macrophages effectively engulf microparticles, especially in the 2-3 μm range, the curvature of which corresponds with that of the macrophage's membrane ruffles (Champion et al., 2008; Pacheco et al., 2013). Thus, microparticles with a mean size of less than 5 microns is essential for an optimal immune response.

Microparticle Size and Distribution.

The size of the microparticles is an important criterion since it directly influences the rate of phagocytosis of the particles by APCs, and an optimal diameter in the range of 1-3 μm is essential. We measured the size of the spray dried particles by analyzing the SEM image of the particles by the ImageJ software version 1.51 (http://imagej.nih.gov/ij/; provided in the public domain by the National Institutes of Health, Bethesda, Md., USA). ImageJ is widely used to determine the micro- and nano-particle's size (Larson, et al., 2013; Liu et al., 2010; Xie and Smith, 2010; McCall and Sirianni, 2013; Baldelli et. al., 2016; Carver and Yang, 2016; Sameni et al., 2008).

Figure 14:
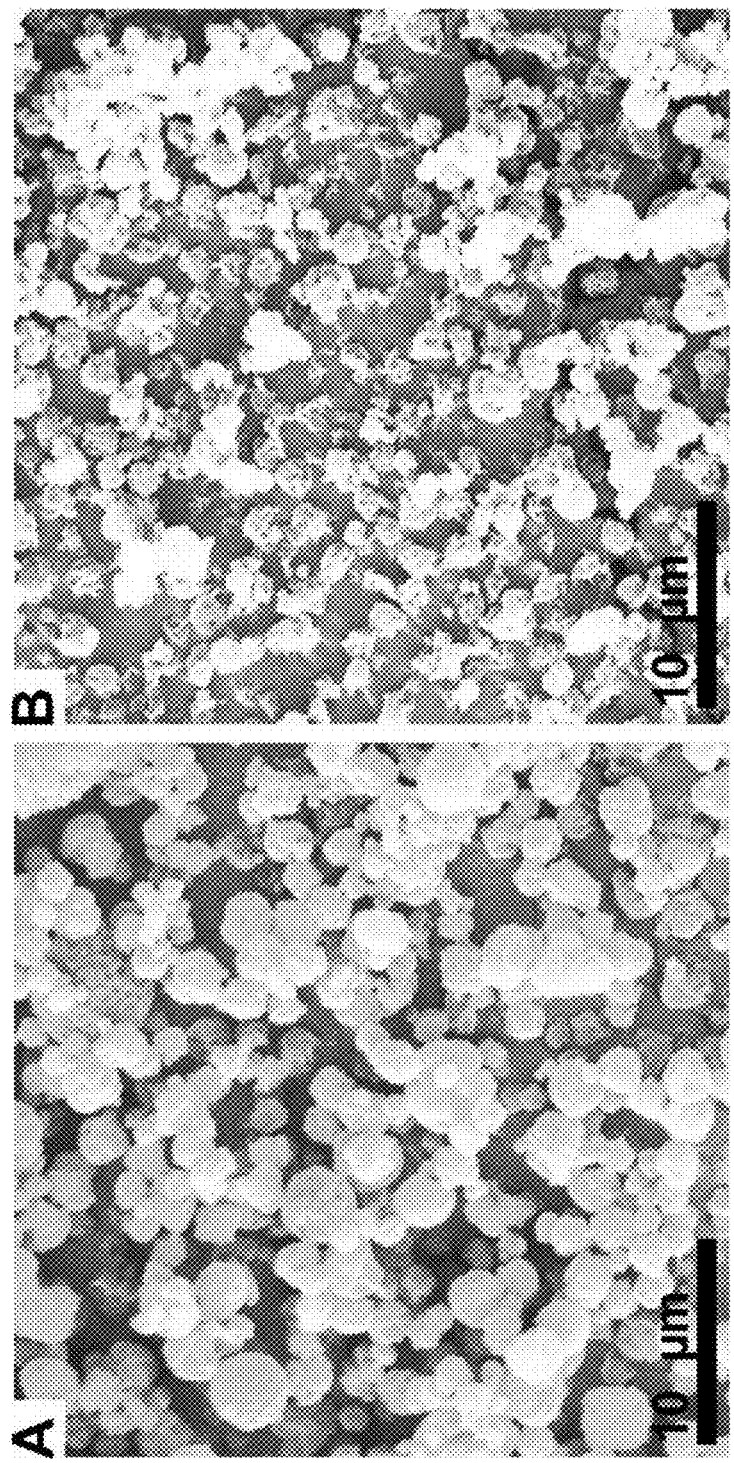
FIG. 14. Scanning electron micrographs of spray-dried microparticles synthesized at different spray-rates. PLGA-PEG (Table 15) microparticles produced from 1% feed solution sprayed at (A) 3.2 ml/min, (B) at 8 ml/min.
Figure 15:
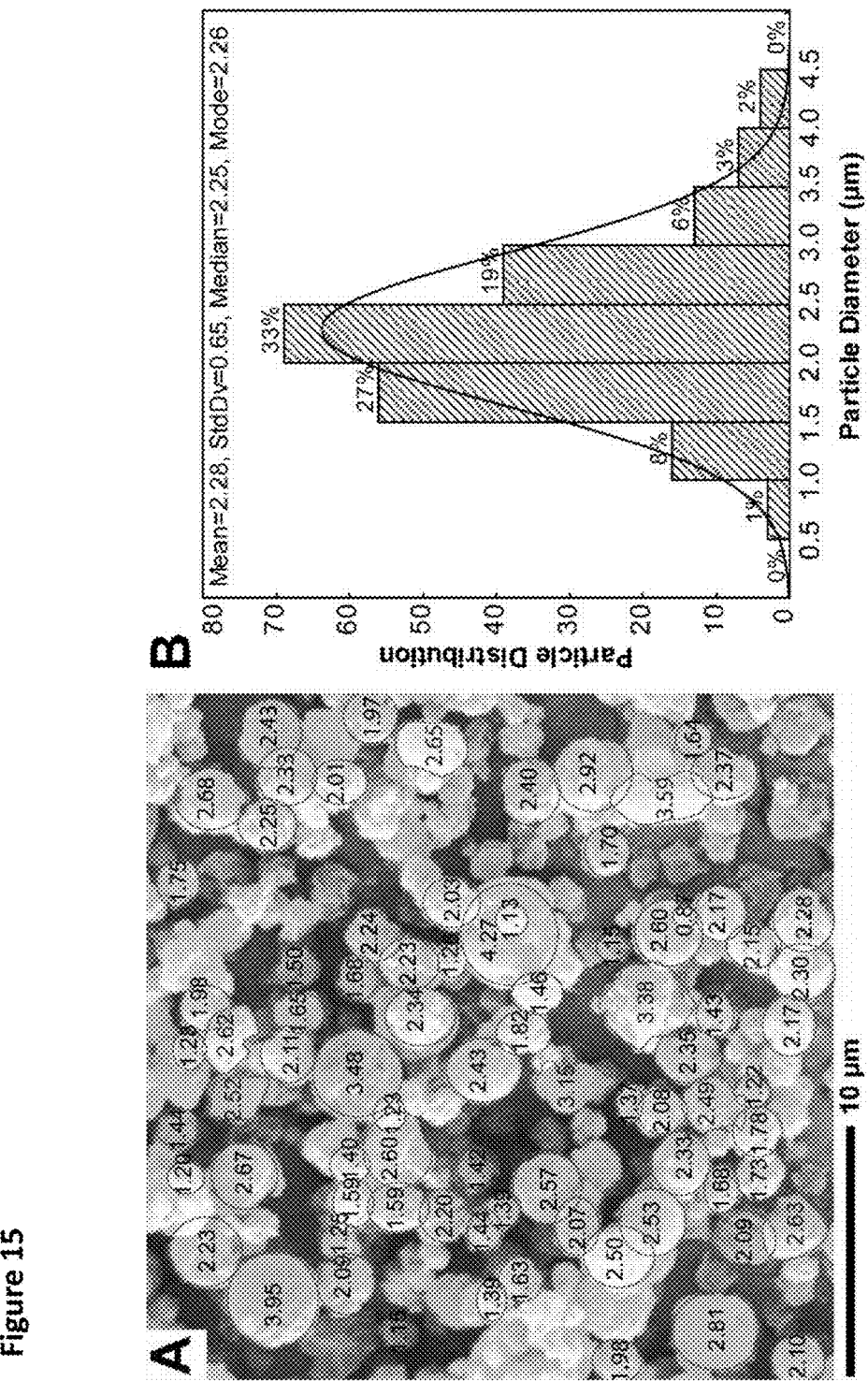
FIG. 15. Size determination of spray dried microparticles. (A) Randomly distributed PLGA-PEG particles in the SEM micrograph were manually marked, and the ImageJ software then automatically determined the particle diameter. (B) Statistical analysis of the diameter of randomly marked particles (N=207).

In case of non-aggregrating individually isolated particles, one can analyze the particle size using automated tools of the ImageJ software. However, the SEM images of our spray dried microparticles demonstrated extensive aggregation of the particles (FIG. 14A). Therefore, we manually marked individual particles in the SEM image, and the ImageJ software then automatically determined the diameter, and aggregated and analyzed these data. As shown in FIG. 15A, the size of the spray dried PLGA-PEG microparticles, synthesized with a 1% feed solution containing only the polymer, was measured with ImageJ. The statistical analysis of the data derived from ImageJ, revealed that the mean diameter of these PLGA-PEG microparticles is 2.28 μm, ranging from 0.5 to 4 μm (FIG. 15B). It is also evident that 80% of the particles are between 1.5 to 3 μm, the optimal range as we expected. It also important to note that the mean (2.28), median (2.25), and mode (2.26) of the data are essentially equal, indicating a symmetrical distribution of the particle size (FIG. 15B).

Effect of the Concentration of Feed Solution on Size and Shape of Microparticles.

In our previous experiments we found that the feed solution containing 1% of total solid resulted in the synthesis of 2.28 μm spherical microparticles by spray drying. However, the surface of these microspheres was rough and irregular (FIG. 14A), which is undesirable for ideal BRM/vaccine microparticles. A low surface roughness is essential for extended release of API. Irregularities will result in an increase in surface area, creating an accelerated diffusive release of API (Dawes et al., 2009). Previously, we had observed that the concentration of feed solution had the greatest influence on size and shape of the microparticles. Therefore, we performed a concentration titration experiment with a two-fold logarithmic dilution series from 1.2% to 4.8% of total solids comprising PLGA-PEG and Pluronic® L121 block copolymer at 6.5:3.5 ratio in the feed solution.

Figure 16:
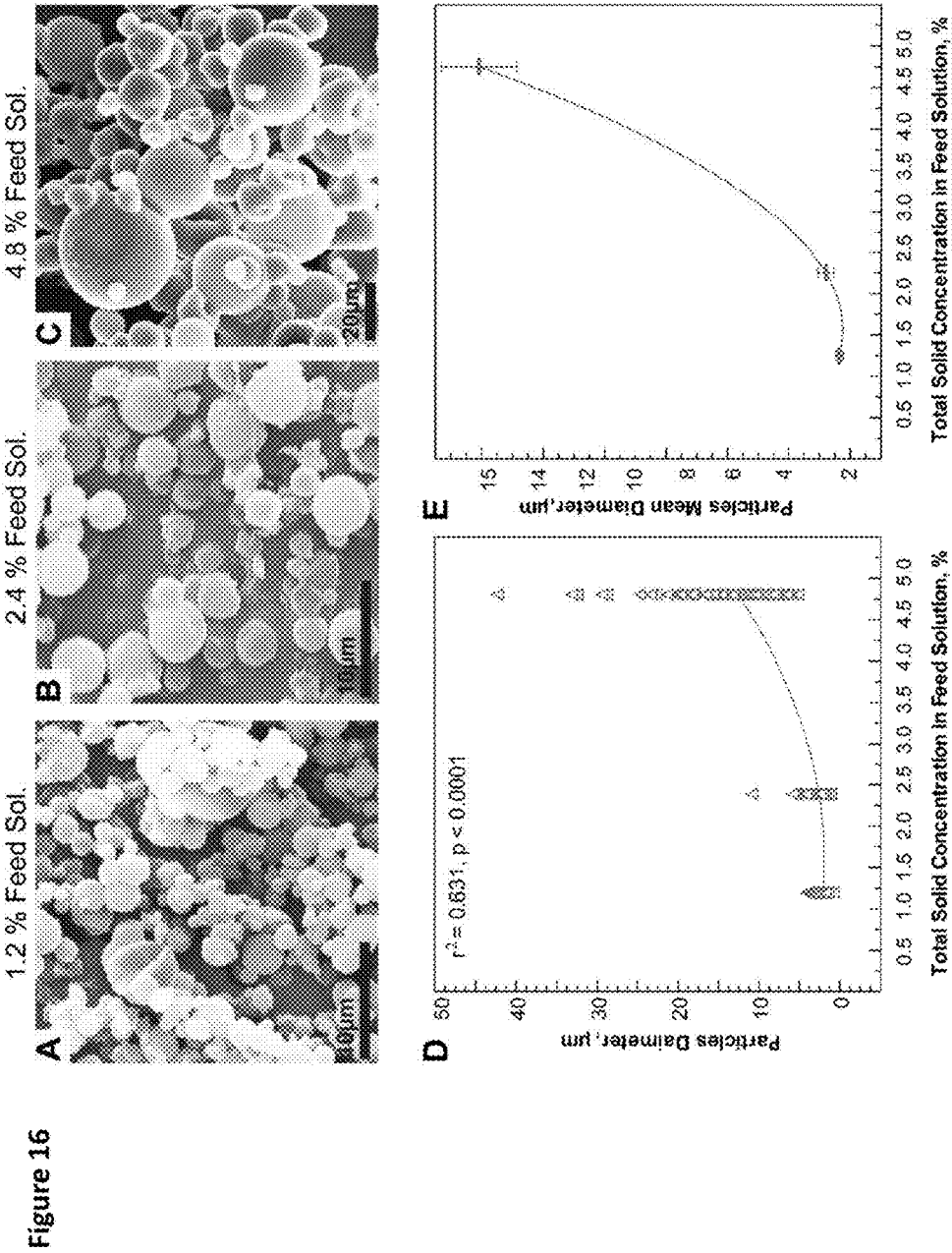
FIG. 16. SEM images and size analysis of spray-dried PLGA-PEG-Pluronic® L121 block copolymer microparticles. PLGA-PEG and Pluronic® L121 block copolymer were dissolved in DCM at a 6.5:3.5 ratio at a final w/v solid concentration of 1.2% (A), 2.4% (B), or 4.8% (C). (D) Polynomial quadratic regression between the diameter of the particles, as determined by ImageJ software from SEM images, and the percentage of total solids used in the feed solution. Each triangle represents one particle (n=100 of randomly marked microparticles in the SEM micrograph of each of 1.2, 2.4, and 4.8% concentration) (E) Linear regression analysis with polynomial fit of the mean diameter of the microparticles at 1.2, 2.4, and 4.8% feed solution concentration as shown in D.
Figure 17:
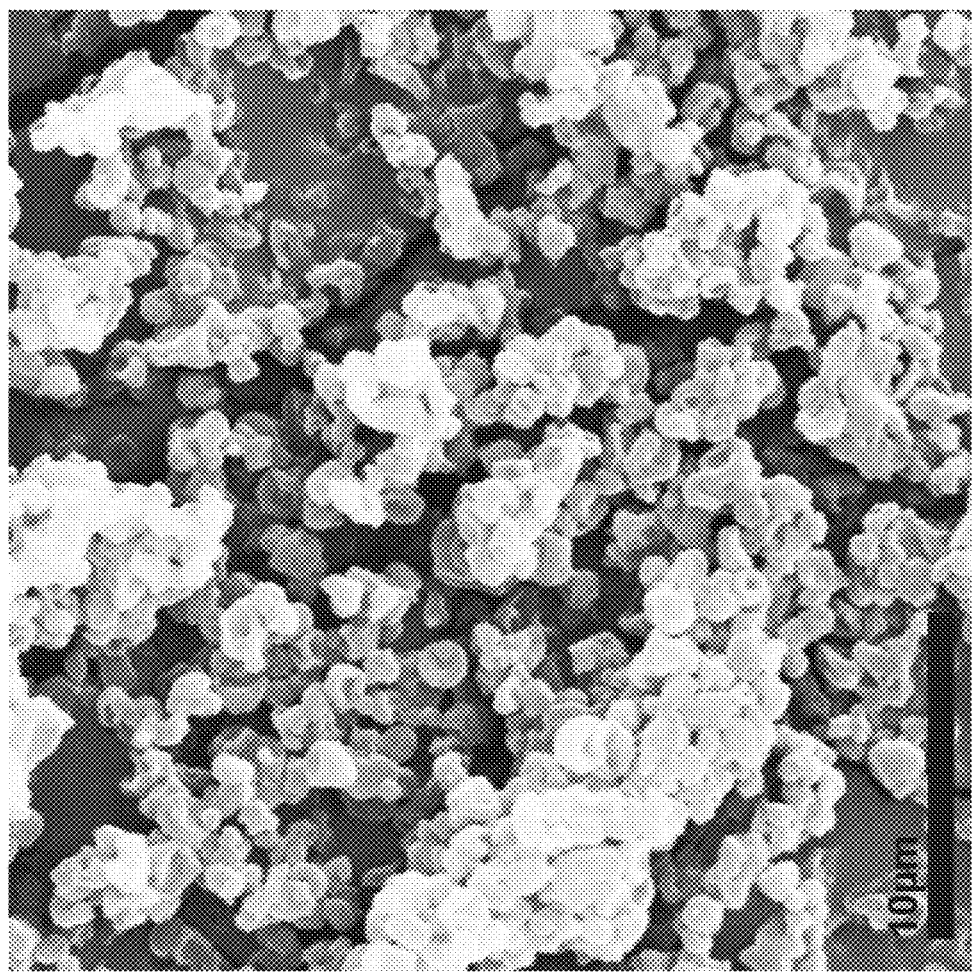
FIG. 17. SEM micrograph of the spray-dried DL-PL (R202S) and Pluronic® L121 block copolymer microparticles synthesized by use of a 1.2% DCM feed solution. DL-poly-lactide of 16.74 MW and Pluronic® L121 block copolymer at 6.5:3.5 weight ratio were spray dried under standard conditions. The mean diameter of the microparticles is 1.21 μm, and the shape and surface are irregular.
Figure 18:
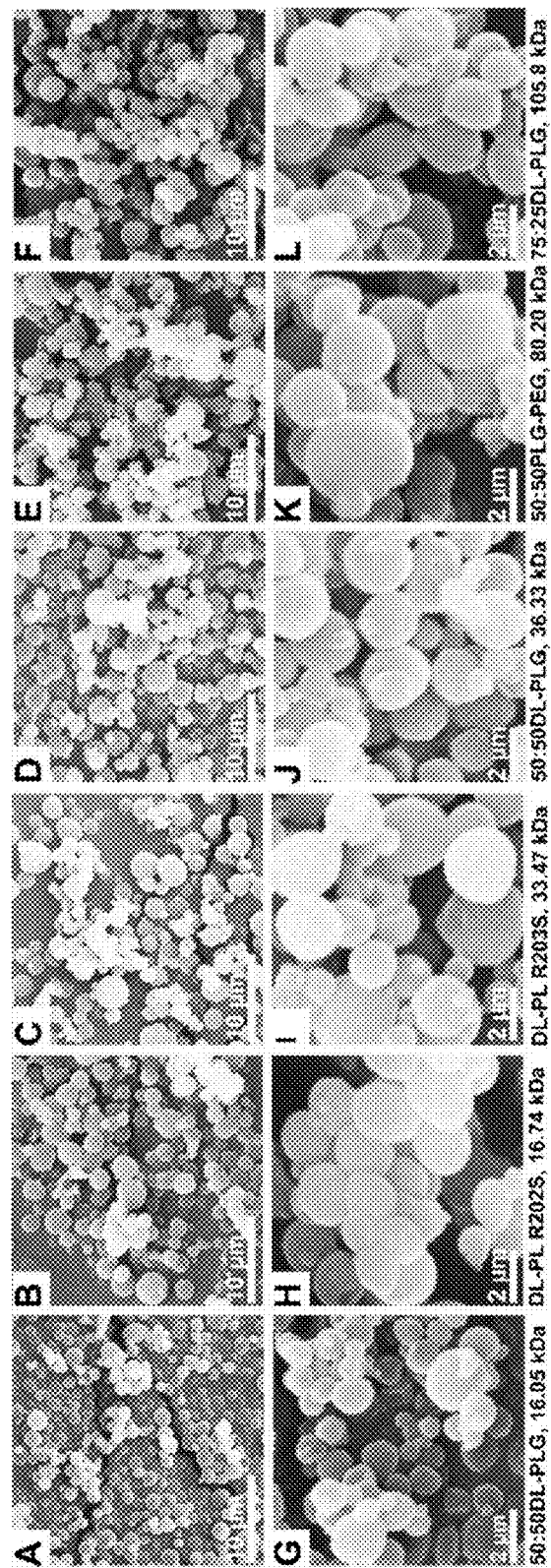
FIG. 18. Scanning electron micrographs of spray-dried microparticles synthesized from 2% (w/v) feed solutions using different polymers. The microparticles were composed of either one of six different polymers and Pluronic® L121 block copolymer. Polymer and Pluronic® L121 block copolymer (6.5:3.5 ratio) were dissolved in DCM at 2% final solid concentration. Each produced particle is shown at low (upper row) (A)-(F) and high (lower row) (G)-(L) magnification.
Figure 19:
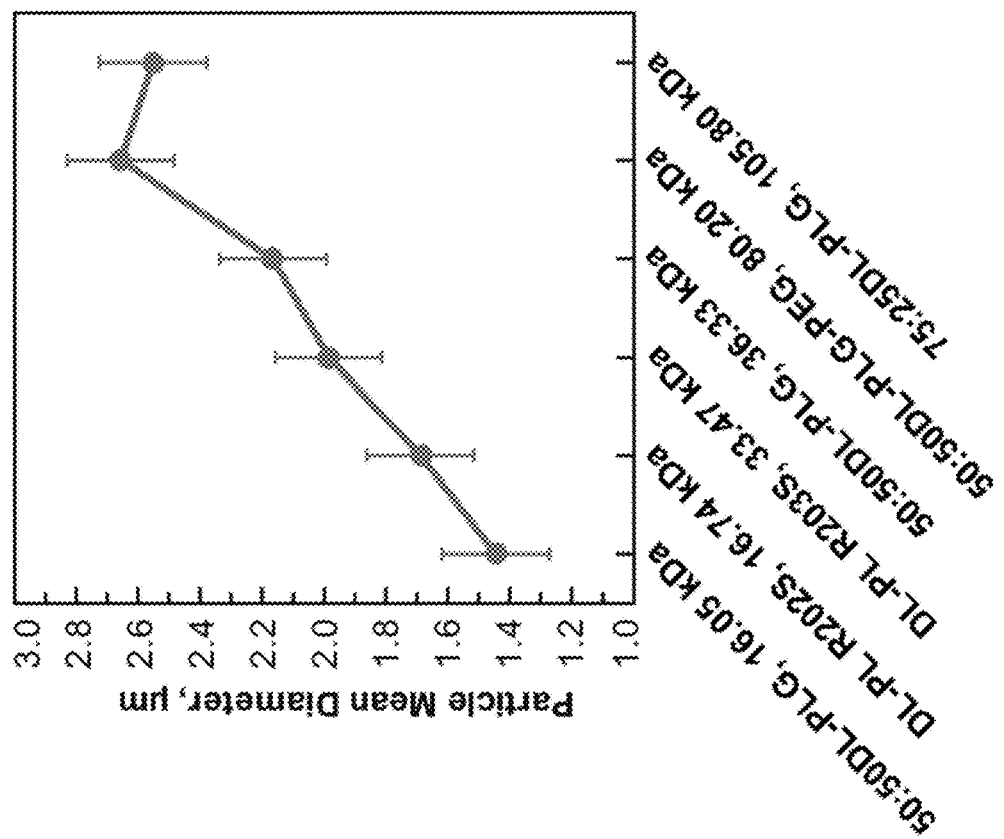
FIG. 19. Mean diameter of spray-dried microparticles synthesized from 2% (w/v) feed solutions. The diameter of random particles (n=100) of each type as shown in FIG. 18 was determined by ImageJ analysis. Error bars indicate 95% CI.
Figure 20:
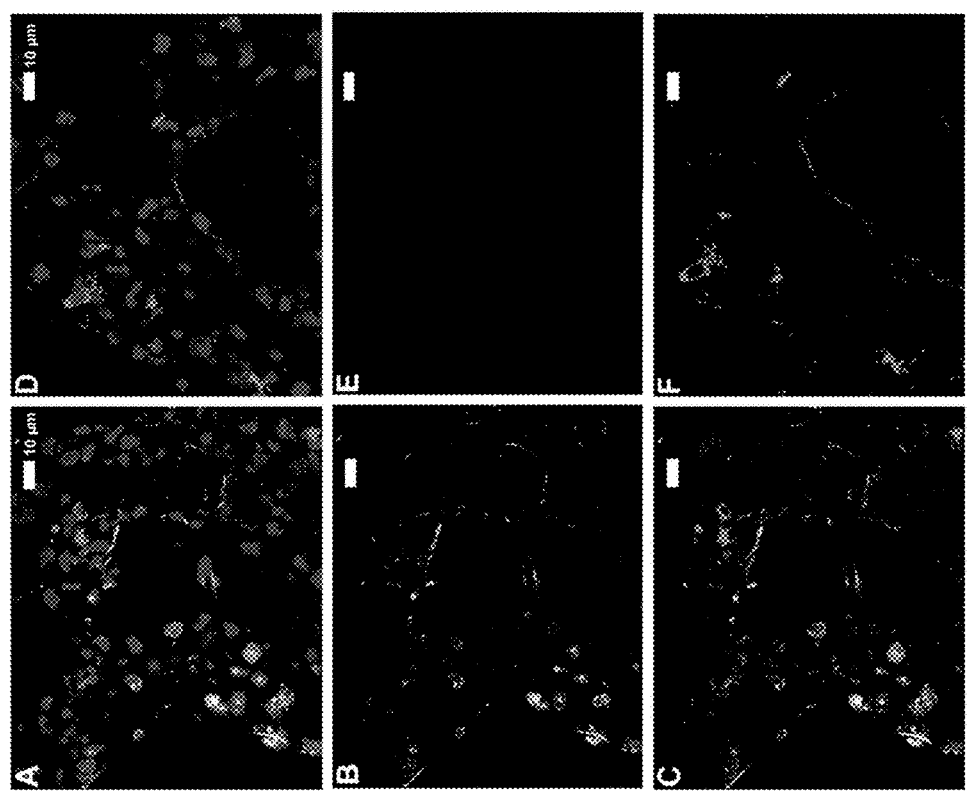
FIG. 20. Confocal microscopic image showing in vivo macrophage uptake of spray dried PLGA-PEG-Pluronic® L121 block copolymer microparticles incorporating a peptide labeled with Alexa-Fluor™ 488. (A) Merged triple-color image of mouse lung after intranasal instillation of microbeads containing a peptide labeled with Alexa Fluor™ 488. The blue color is derived from DAPI fluorescence from DNA staining of cellular nuclei, the green color corresponds to microparticles labeled with green-fluorescent peptide, and the red color indicates fluorescence associated with binding of Alexa Fluor 594-labeled antibodies against F4/80, a macrophage cell membrane marker protein. The empty spaces between aggregated cells indicate lung alveolar cavities. (B) Isolated green fluorescence indicating the location of microbeads and cytosolic peptide that diffused out of microbeads. (C) Merged green and red fluorescence indicating the co-localization of the majority of microbeads with macrophages. This demonstrates that the majority of microbeads are phagocytosed by macrophages within 24 hours. (D-F) Corresponding photomicrographs of a control specimen from a mouse that received unlabeled microbeads.
Figure 21:
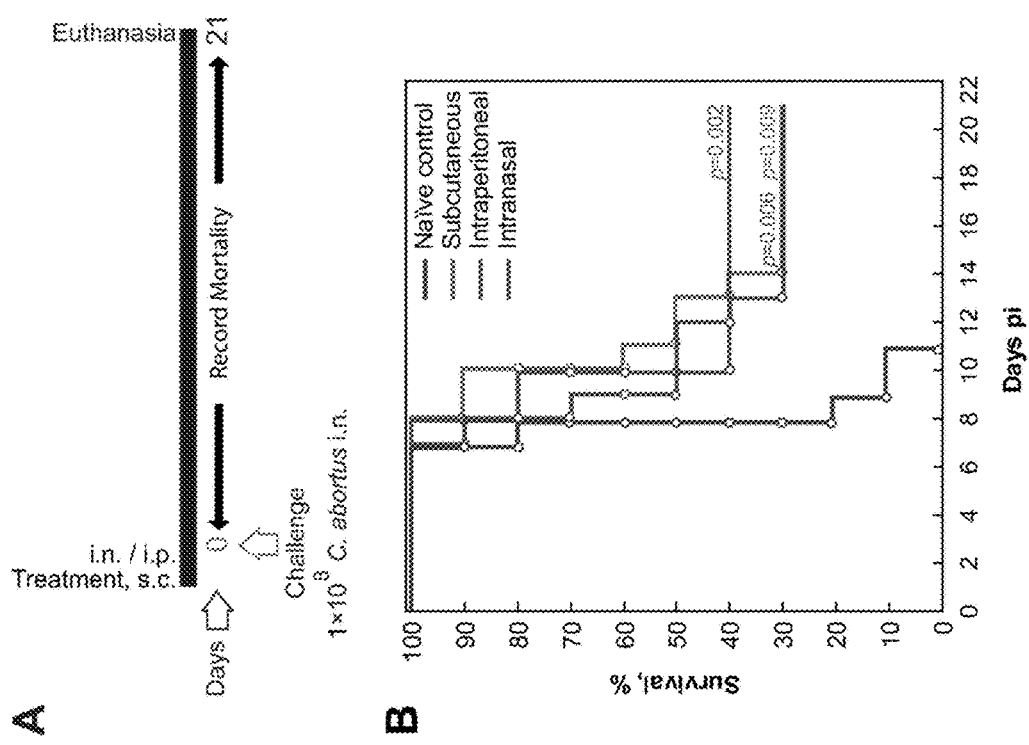
FIG. 21. BRM effect of PLGA-PEG microparticles via different routes of administration. (A) Schematic representation of the BRM experimental protocol. C3H/HeJ mice received 10 μg of PLGA-PEG-Pluronic® L121 block copolymer BRM microparticles suspended in PBS/0.1% Kolliphor® HS 15 non-ionic solubilizer and emulsifying agent via i.n., s.c., or i.p. administration. Two days (s.c.) or one day (i.n. and i.p.) after treatment all mice were i.n. challenged with $1 \times 10^8$ C. abortus organisms. The naïve control group received i.n. only PBS/0.1% Kolliphor® HS 15 non-ionic solubilizer and emulsifying agent one day before challenge. (B) Survival analysis (Kaplan-Meier survival estimate; Cox's F test; n=10 mice/group).

Spray drying of all feed solutions containing either 1.2%, 2.4%, or 4.8% of PLGA-PEG and Pluronic® L121 block copolymer resulted in spherical microparticles with smooth surfaces as observed in their SEM micrographs (FIG. 16A-C). The SEM micrographs also demonstrated that microparticles became sequentially larger as the feed concentration of solids increased (FIG. 16A-C). Quadratic polynomial regression analysis revealed a positive correlation for the diameter of the particles with the concentration of solids in the feed solution (r=0794; p<0.0001; FIG. 16D), with the mean diameter of 2.36, 2.79, and 14.07 μm for the 1.2, 2.4, and 4.8% feed solutions, respectively (FIG. 16E). It is apparent from the data that a 1.2% feed solution is the lowest concentration that should be used to synthesize spray-dried PLGA-PEG-Pluronic® L121 block copolymer microparticles with optimal size and shape. Although, 2.4% feed solution produced PLGA-PEG microparticles with 2.79 μm in diameter—which is at the upper limit for an optimal size (1 to 3 μm), and hence risks the production of substantial numbers of particle with more than 3 μm. Analysis of the particle mean diameter provides a theoretical mean diameter of 2.5 μm for a 2% feed solution (FIG. 16E). Therefore, a feed solution with the concentration in between 1.2 to 2% would be the best choice to synthesize microparticles with optimal size and shape while using PLGA-PEG as polymer and with Buchi 190 mini spray dryer.

Effects of Polymers Type and Molecular Weight on Microparticles Size and Shape.

As mentioned earlier, the type of polymer and its molecular weight significantly affect the degradation kinetics of the spray dried microparticles (Kamaly et al., 2016) and therefore the release of vaccine antigen and subsequent immune response. For this reason, we tested spray drying to optimal particle size of six different PLGA polymers that later would be analyzed for kinetics of degradation and antigen release, and mechanisms of antigen release.

In our previous experiment we used PLGA-PEG of 80.2 kDa molecular weight as polymer which is comprised of 50:50 DLG and contains 5 wt % poly-ethylene-glycol (PEG) of 5 kDa MW. In our next experiment we examined whether different DL-Poly-lactide (DL-PL) or DL-Poly-lactide-co-glycolide (DL-PLG) polymers of different molecular weight and composition could produce equally sized microparticles. In an initial attempt we used DL-PL (R202S) with 16.74 kDa molecular weight and synthesized microparticles with 1.2% feed solution. As shown in FIG. 17, at the 1.2% feed solution, R202S with five-fold lower molecular weight than PLG-PEG produced small microparticles (1.21.μm mean diameter) that were not fully spherical (FIG. 17). We anticipated that a higher concentrated 2% feed solution would produce larger and optimally shaped microparticles. Therefore, as next step we determined the shape and size of microparticles produced from six different PLG and PL polymers (Table 14) by use of a 2% feed solution.

As shown in FIG. 18, the 2% feed concentration yielded spherical microparticles with smooth surfaces for all polymers (FIG. 18 A-L). Particles size analysis revealed that the microparticle diameter was within the optimal range (1.5 to 2.6) for all polymers. The results also clearly demonstrated that the molecular weight of the polymers is significantly positively correlated to the diameter of the particles (FIG. 19; Table 14). Importantly, only molecular weight, but not composition of the polymers (PL versus PLG), influenced the microparticle diameter (Table 14).

TABLE 14

Differences in mean diameters of the spray-dried microparticles synthesized from 2% feed solutions analyzed by one-way ANOVA.

| Polymer | Mw (kDa) | Mean Diameter (μm) | P value (Tukey HSD test) | | | | | |
|---|---|---|---|---|---|---|---|---|
| 50:50 DL-PLG, IV 0.39 | 16.05 | 1.45 | | 0.368 | <0.001 | <0.001 | <0.001 | <0.001 |
| 100:0 DL-PL (R202S), IV 0.20 | 16.74 | 1.69 | 0.368 | | 0.159 | 0.002 | <0.001 | <0.001 |
| 100:0 DL-PL (R203S), IV 0.32 | 33.47 | 1.98 | <0.001 | 0.159 | | 0.692 | <0.001 | <0.001 |
| 50:50 DL-PLG, IV 0.59 | 36.33 | 2.16 | <0.001 | 0.002 | 0.692 | | 0.001 | 0.0229 |
| 50:50 DL-PLG-PEG, IV 0.79 | 80.20 | 2.66 | <0.001 | <0.001 | <0.001 | 0.001 | | 0.960 |
| 75:25 DL-PLG, IV 0.69 | 105.80 | 2.55 | <0.001 | <0.001 | <0.001 | 0.023 | 0.960 | |

In sum, this particle size optimization experiment clearly demonstrates that the concentration of total solids in feed solution and the molecular weight of the polymers have a significant impact on the size of 6.5:3.5 polymer:Pluronic® L121 block copolymer microparticles, but not the type of the polymer. However, a feed solution with 2% total solids containing any DL-PL or DL-PLG at different co-polymer ratios with a molecular weight range of 10 to 100 kDa will produce microparticles within the optimal size range (1 to 3 μm) and shape (spherical and smooth) for phagocytosis, if the microparticles are synthesized in a Büchi B-190 spray-dryer with standard setting for the remaining parameters.

In Vivo Uptake of Microparticles by Macrophages.

After characterization of the DL-PL and DL-PG spray-dried microparticles, we investigated the uptake of these particles by macrophages in an in vivo mouse model. The spray dried PLGA-PEG:Pluronic® L121 block copolymer microparticles incorporating fluorescently labeled peptide were intranasally inoculated into mice. Twenty four hours later, the lungs were collected, zink-formalin fixed, sucrose-dehydrated, cryosectioned, immunostained, and observed under a confocal fluorescence microscope. As shown in FIG. 20, lung macrophages efficiently engulfed the majority microparticles as evident by the presence of green fluorescence (Alexa-Fluor 488-conjugated peptide) inside macrophages with high surface expression of the F4/80 macrophage marker (FIG. 20 D-F).

Immunopotentiating Effect of Optimal PLGA-PEG: Pluronic® L121 Block Copolymer Microparticles when Used in Different Routes of Administration.

After the extensive optimization of spray drying procedures and subsequent analyses of in vitro degradation kinetics and in vivo phagocytosis of the 1 to 3 μm microparticles, we evaluated the immunostimulating effect of such BRM microparticles when administered by different routes. C3H/HeJ mice received 10 μg of PLGA-PEG-Pluronic® L121 block copolymer microparticles either via subcutaneous (s.c.), intraperitoneal (i.p.), or intranasal route (i.n.). Two days (s.c.) or one day (i.p. and i.n.) after treatment, the mice were i.n. challenged with a lethal dose of $1 \times 10^8$ C. abortus EBs and monitored for three weeks (FIG. 21A). The naïve control received i.n. PBS one day before challenge.

The mortality kinetics and survival rate were highly significantly different between naïve control mice and the mice in all three different treatment groups (Coxs' F test p=0.006, 0.009, and 0.002 for the difference between naïve and mice with i.n., s.c., or i.p., BRM administration, respectively; FIG. 21B). The naïve control showed rapid mortality—starting from seven days after challenge inoculation. Eighty percent of the mice were dead on day 8 post challenge, and the remaining mice died by day 11 after challenge inoculation (FIG. 21B). In contrast, mice of all treatment groups tended to die later. In the intranasal group, mice died between days 7 and 13, and the remaining 30% mice survived (FIG. 21B). Similarly, 30% of the mice in the subcutaneous group survived, the dead mice, however, succumbed to the challenge infection later than in the intranasal group. The best protected group were the mice that received the BRM microparticles intraperitoneally, although not statistically significant different from the other administration routes, with mortality only between days 8-11, and 40% surviving. The findings clearly demonstrated that the PLGA-PEG-Pluronic® L121 block copolymer microparticles had an immunostimulating effect irrespective of the route of administration.

Immunopotentiating Effect of BRM Microparticles Containing Different Th1 Adjuvants.

AS a final step, we evaluated different Th1 adjuvants in an intranasal immunopotentiator experiment with PLGA BRM microparticles. C3H/HeJ mice were i.n. inoculated with 10 μg of either only RG502H microparticles (carrier control), or RG502H microparticles containing one of three Th1 adjuvants—Pluronic® L121 block copolymer, Trehalose-di-behenate (TDB), and Resiquimod (Table 2.1). Three days after treatment, the mice were i.n. challenged with a lethal dose of $3 \times 10^8$ C. abortus EBs and monitored for three weeks (FIG. 22A).

Figure 22:
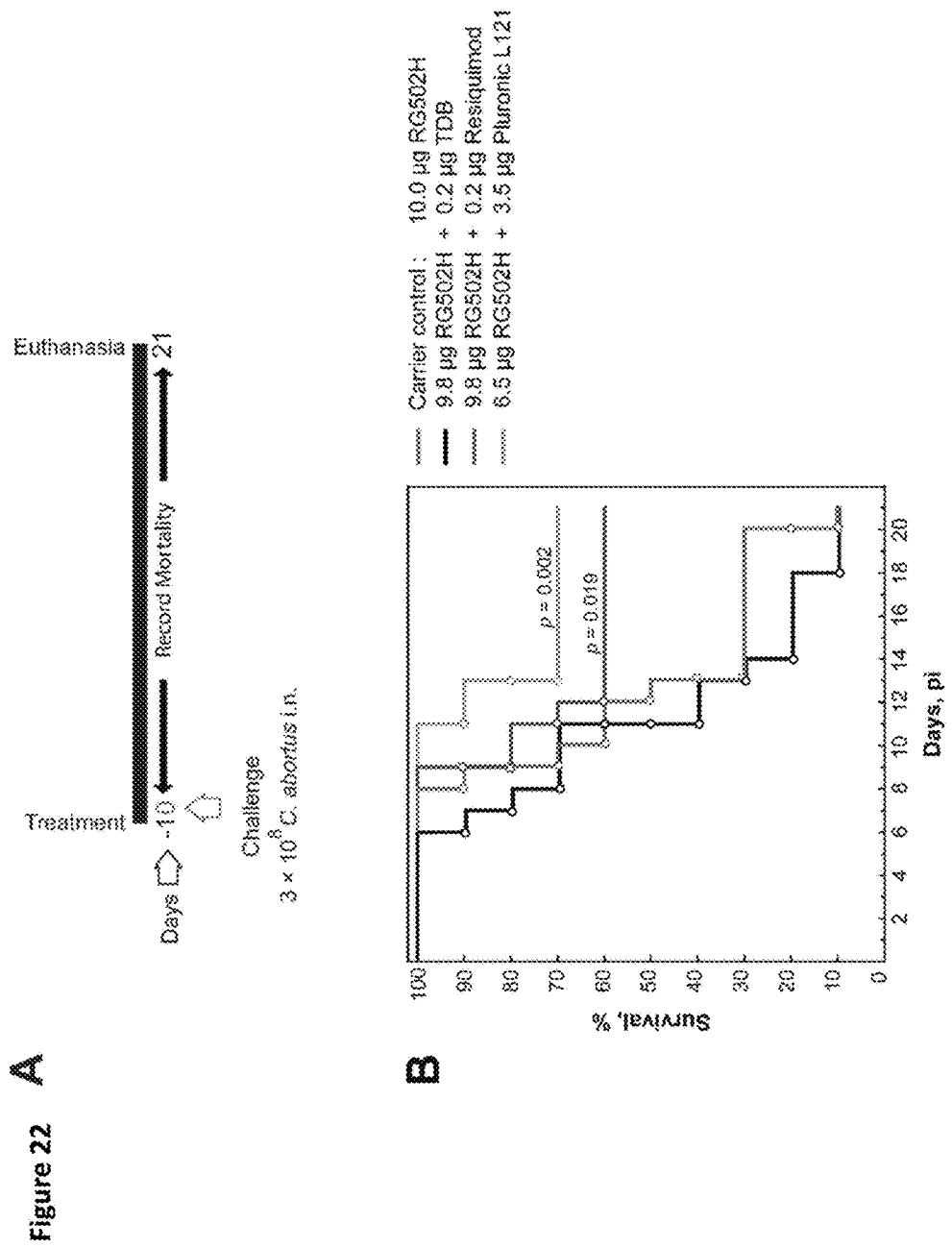
FIG. 22. Immune modulation by BRM microparticles with Th1 adjuvants Pluronic® L121 block copolymer, TDB, and Resiquimod. (A) Schematic presentation of BRM experimental protocol. Three days before i.n. challenge inoculation with $3 \times 10^8$ C. abortus, C3H/HeJ mice were i.n. inoculated with 10 μg spray-dried RG502H microparticles (carrier control) suspended in 20 μl PBS/0.1% Kolliphor® HS 15 non-ionic solubilizer and emulsifying agent, or with RG502H microparticles containing either one of the three Th1 adjuvants—TDB, Resiquimod, or Pluronic® L121 block copolymer. After challenge mice were monitored daily, and the surviving mice were euthanized on day 21. (B) Survival analysis of mice in different groups (Kaplan-Meier survival estimate; Cox's F test (n=10 mice/group).

Starting from four days after challenge inoculation, the mice carrier control group (received only RG502H microparticles) lost body weight, became progressively sicker, lost approximately 28% of their weight, and 90% of the mice died within 21 days after challenge infection (FIG. 22B). The mice that received the TDB adjuvanted microparticle also followed a similar trend and lost approximately 30% body weight, and 90% of the mice died within 3 weeks after challenge (FIG. 22B). In contrast, mice that received either Pluronic®L121 block copolymer- or Resiquimod adjuvanted microparticles were comparatively healthier. Starting from day 8 they experienced a minor body weight loss until day day 12 of approximately 8% in Pluronic® L121 block copolymer group and 10% in the Resiquimod group. However, beginning day 14 after challenge inoculation, surviving mice in both groups of this group stabilized and steadily gained weight again. Importantly, mice in both groups showed significantly lower mortality by day 21 than the carrier control and TDB groups—30% mortality for Pluronic® L121 block copolymer (p=0.002 vs carrier control) and 40% mortality for Resiquimod (p=0.019 vs carrier control).

Discussion

Limitations of current vaccines, particularly against intracellular pathogens and cancer, have encouraged the application of various vaccine delivery systems in attempts to improve vaccine efficacy. Among proposed vaccine delivery systems, synthetic biodegradable polymeric microparticles have been gaining more attention, specifically regarding their advantages as an antigen/adjuvant delivery vehicle. These advantages include: their inherent features that can be tuned according to the desired antigen release profile, the ease of charge or hydrophobicity modification, and the ability to target uptake by APCs. However, the physicochemical properties of these particulates depend on a number of factors such as: preparation technique, polymer composition, hydrophobicity, molecular weight, and particle size (Allahyari and Mohit, 2015; Lima and Junior, 1999; Tracy, et al., 1999). In this study, through a series of optimization approaches we developed optimal PLGA microparticles, entrapped the Th1 adjuvant Pluronic® L121 block copolymer by spray dry technology, and investigated their immunopotentiation effect in an immunosuppressed C3H/HeJ mouse model. The optimization of microparticles and the in vivo mouse model studies were performed in simultaneous and stepwise approaches to develop a microparticulate delivery platform that can be utilized in low dose vaccine delivery against Chlamydia abortus.

To synthesize microparticles, we used industrially scalable spray drying technology and demonstrated that it is a perfectly suited technique to synthesize suitable microparticles for vaccine delivery. However, as previously described, microparticles characteristics are dependent on different process parameters such as inlet and outlet temperatures, spray-rate of feed, polymer concentration in the organic solvent (Conte et al., 1994), and the nature of the organic solvent (Gander et al., 1995). Through a series of optimization approaches we standardized different spray dry parameters (feed spray rate at 3.2 mL/min, inlet temperature 58±2° C.; outlet temperature 38±2° C.; spray gas flow 6 bar; atomization air flow rate 500 l/h; and aspirator setting 20) to synthesize our desired microparticles with the Büchi-190 spray dryer.

We then performed an in-depth investigation on the size of the microparticles as it is a criterion of overriding importance for phagocytotic uptake of microparticles by APCs. In an early study conducted in the phagocytosis of polystyrene microspheres (0.5-4.6 μm) by mouse peritoneal macrophages, it was reported that maximal phagocytosis occurred for an intermediate particle size of 1.7 μm (Tabata and Ikada, 1988). A recent study by Champion et al. (2008) demonstrated that 2-3 μm polystyrene particles were optimally phagocytosed by rat peritoneal macrophages Therefore in this study we were interested to synthesize 1 to 3 μm PLGA microparticles that would be easily phagocytosed by APCs. We found that the concentration of total solid in the feed solution as well as molecular weight of the polymer greatly influence the size of particles. We performed a concentration titration experiment of solids in feed solution and determined that a 2% concentration is ideal to synthesize optimal microparticles of 1 to 3 μm diameter with a wide range of DL-PL or DL-PLG polymers. In a subsequent in vivo mouse model experiment we found that PLGA-PEG microparticles with 2.66 μm diameter were efficiently engulfed by macrophages in the lung.

The ultimate goal of our approach was to utilize the microparticles as vaccine delivery vehicle in our low antigen dose vaccine platform against Chlamydia abortus. Therefore in this study we investigated their potential as immunostimulant while delivering a Th1 adjuvant. To evaluate the immunopotentiating effect we used C3H/HeJ mice in the C. abortus respiratory disease model. As this mouse has a truncated Tlr4 protein, they fail to respond to LPS, including chlamydial LPS. This results in a lack of a protective innate immune response against chlamydial challenge inoculation, and subsequent disease with high mortality within 2 to 3 weeks. We found that administration of PLGA-PEG or PLG (RG502H) microparticles containing the Th1 adjuvant Pluronic® L121 block copolymer, one or three days before challenge inoculation of lethal *C. abortus*, significantly reduces the mortality of these mice. Therefore these microbeads at least partially substituted for the absent LPS response in these mice. We also demonstrated that the immunopotentiang effect can be obtained by administration either by the subcutaneous, intraperitoneal, or intranasal route. However, the effect is highly dose dependent, with an optimal dose range of 5 to 10 μg per mouse, and lower as well as higher doses were actually counterproductive. Similarly, only one treatment, one or three days before challenge inoculation was sufficient, while multiple dosages failed to induce protection, and even exacerbated disease, most like due to an aberrant inflammatory response derived from overstimulation. Finally, we also demonstrated that the particulate delivery is effective with resiquimod, a different Th1 adjuvant.

In conclusion, microparticles based on synthetic biodegradable polymers are an extensive area of research for effective delivery of vaccine antigens and pharmaceutical drugs in human and veterinary medicine. In the current study we focused on the synthesis of DL-PL and DL-PLG microparticles using spray drying technology. The optimization of spray drying parameters and in vitro and in vivo characterization of microparticles that have been performed in this study will significantly benefit in immune studies of polymeric microparticles synthesize by an industrially scalable spray dry technology.

Materials and Methods

Preparation of Microparticles with or without an Adjuvant.

Chemicals and Reagents.

The following chemicals were obtained from commercial suppliers and used as received: dichloromethane (Sigma Aldrich, St. Louis, Mo., USA), Kolliphor® HS 15 non-ionic solubilizer and emulsifying agent [synonym: Macrogol (15)-hydroxystearate, Polyethylene glycol (15)-hydroxystearate, Polyoxyethylated 12-hydroxystearic acid, Solutol® HS 15 non-ionic solubilizer and emulsifying agent] (BASF Corp., Germany), Lactopress® Anhydrous Microfine (DFE Pharma, Germany), Benzalkonium chloride (Sigma Aldrich, St. Louis, Mo., USA).

Adjuvants.

The adjuvants used in this experiment were: Poly(ethylene glycol)-block-poly(propylene glycol)-block-poly(ethylene glycol) (Synonym—PEG-PPG-PEG, Pluronic® L-121 block copolymer) (a product of BASF Corp., Germany, obtained from Sigma Aldrich, St. Louis, Mo., USA), Trehalose Dibehenate (TDB) (Avanti Polar Lipid, Inc., Alabaster, Ala. 35007); and Resiquimod (R848) (Invivogen, San Diego, Calif., USA).

Polymers.

A list of synthetic biodegradable polymers used in this study is shown in Table. 15, with their physiochemical properties as indicated by the manufacturers.

TABLE 15

Lactic/glycolic acid polymer samples used in this study

| Chemical Name | Abbreviation | Source | Synonym | IV (dL/g) | Mw (Da) | Tg [° C.] | Degradation timeframe |
|---|---|---|---|---|---|---|---|
| 50:50 Poly(DL-lactide-co-glycolide) | 50:50 DL-PLG | Durect Corp. | Lactel® B6010-1 | 0.26-0.54 | 8,000-30,000 | | |
| 50:50 Poly(DL-lactide-co-glycolide) | 50:50 DL-PLG | Durect Corp. | Lactel® B6010-2 | 0.55-0.75 | 30,000-60,000 | 45-50 | 1-2 months |
| Methoxy poly(ethylene glycol)-50:50 DL-poly(lactide-co-glycolide) | 50:50 DL-PLGA-PEG | Evonik | | 0.79 | 80,200 | 10 | 1 to 4 weeks |
| 75:25 Poly(DL-lactide-co-glycolide) | 75:25 DL-PLG | Durect Corp. | Lactel® B6007-1 | 0.55-0.75 | 66,000-107,000 | 50-55 | 4-5 months |
| Poly(D,L-lactide) | 50:50 DL-PL | Evonik | Resomer® R202S | 0.16-0.24 | 10,000-18,000 | 38-42 | <6 months |
| Poly(D,L-lactide) | 0:50 DL-PL | Evonik | Resomer® R203S | 0.25-0.35 | 18,000-28,000 | 46-50 | <6 months |
| 50:50 Poly(D,L-lactide-co-glycolide) | 50:50 DL-PLG | Evonik | Resomer® RG502H | 0.16-0.24 | 7,000-17,000 | 42-46 | <3 month |

IV—Intrinsic viscosity;
Mw—Molecular weight from Manufacturer (range);
Tg—Glass transition temperature.

Spray Dryer.

Figure 23:
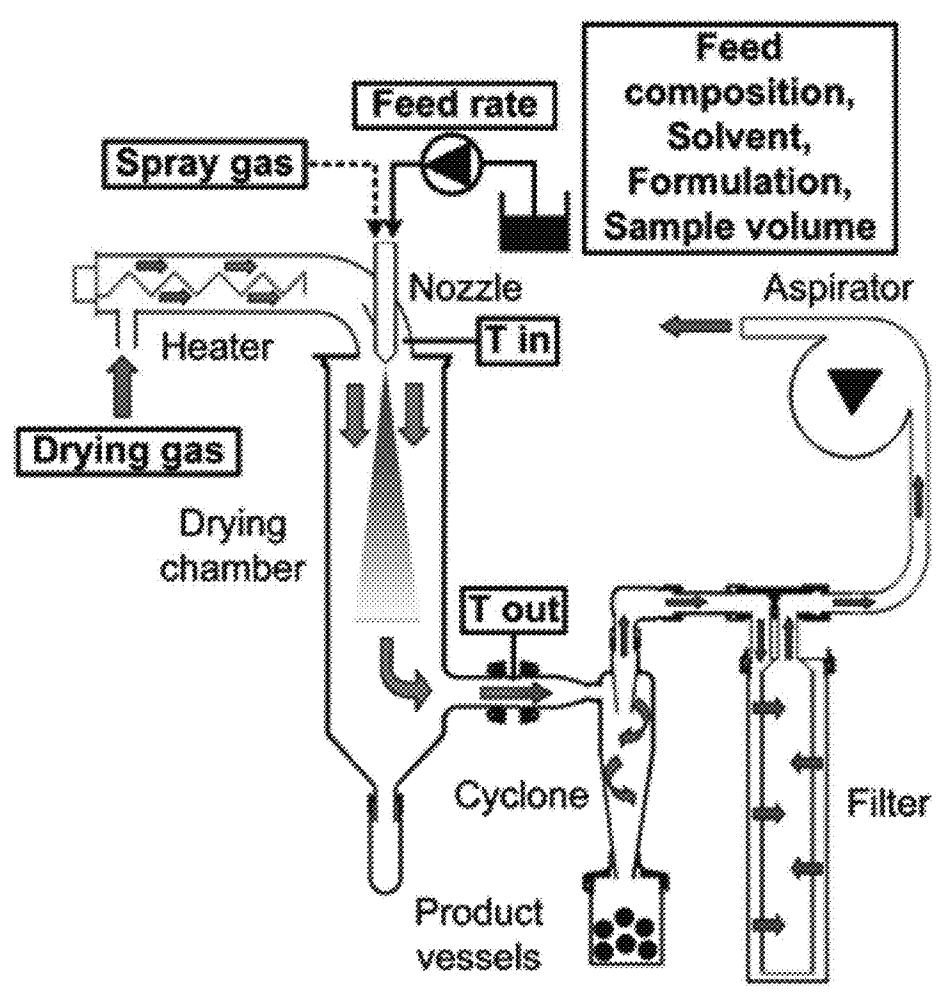

The microencapsulating experiments were carried out by use of a bench-top Büchi mini spray dryer model B-190 (Büchi Labortechnik AG, Flawil, Switzerland). The main components of the system are the feed system of the of the microencapsulating formulation, constituted by a peristaltic pump, a two fluid atomizer (nozzle diameter of 0.7 mm) and an air compressor; the feed system of the drying gas, constituted by a blower, an air filter and a temperature control system. The dried product was collected in a Büchi high performance glass cyclone. FIG. 23 shows the schematic representation of process diagram of the spray dryer used.

Microparticle Production.

Stock solutions of polymers and adjuvant were prepared separately with DCM at 50 mg/ML. Feedstock solutions of adjuvants and/or polymers were prepared in DCM by adding the desired volume of the stock solution at the concentration of either 1%, 1.2%, 2.4%, or 4.8% of total solids, as required for different experiments. The ratio of the polymers and adjuvants were either 2:1 or 6.5:3.5, as needed.

Microparticles were obtained by spraying the prepared feedstock solution through the nozzle of the spray dryer. The spray rate of feed was constant at 3.2 ml/min except for one optimization experiment when 8 ml/min was used. Identical drying conditions (inlet temperature 58±2° C.; outlet temperature 38±2° C.; spray flow 6 bar; atomization air flow rate 500 l/h; and maximum aspirator setting 20) were used for all samples. The spray-dried microparticles obtained were collected in glass vials sealed with Parafilm and stored in a desiccator at room temperature until further characterization.

Microparticle Characterization.

Morphology.

The surface morphology and shape of the spray-dried microparticles was visually assessed by the Zeiss EVO 50 scanning electron microscope (Carl Zeiss, Germany). Briefly, spray-dried microparticles were placed on adhesive carbon tapes mounted on aluminum stubs followed by sputter coating with a thin layer (5 nm) of gold particles for 2 minutes with an EMS 550x auto sputter coater (Electron Microscopy Sciences, Hatfield, Pa.) under an Argon gas purge. The specimens were then imaged at an accelerating voltage of 20 kV energy with magnification of 3000, 5000 and 10000 times.

Particulate Size Analysis.

To quantify the size of the microparticles, the image analysis software, ImageJ (Rasband 2010), was used to measure the Feret's diameter (area-based diameter of non-sperical particles) of at least 100 randomly distributed microparticles per sample. Due to high agglomeration of the particles, as observed in scanning electron microscope (SEM) image, the Feret's diameter of each particle was manually measured in the ImageJ software instead of using automatic measurement procedures.

In Vivo Macrophage Uptake.

Mice received intranasally PLG-PEG-Pluronic® L121 block copolymer microparticles with entrapped *C. abortus* peptide conjugated with Alexa Fluor 488. One day later, mice was anesthetized by intraperitoneal injection of ketamine and xylazine, and the lung was perfused with PBS and fixed with Z-Fix. The fixed lung was treated under vacuum with successive sucrose gradient solutions (10%, 20%, and 30%) for dehydration and cryoprotection. The sucrose infiltrated lung was embedded with 2 ml Neg-50 (Richard-Allan Scientific) in a cryomold boat and the prepared lung cryomold was stored at −80° C. Using a cryostat (HM 550 Series, Richard-Allan Scientific), lung sections were cut to 8 μm, mounted onto Superfrost/Plus microscope slides (Fisher Scientific), air dried in the dark (to avoid photobleaching of fluorescent beads), and blocked with antibody dilution buffer (5% BSA and 10% donkey serum in PBS). Sections were stained with F4/80 rat IgG2b monoclonal antibody (1:500 overnight; Fisher), followed by donkey anti rat IgG Alexa Fluor 594 (1:500 for 1 h; Fisher). Nuclei were counterstained with DAPI (4, 6-diamidino-2-phenylindole) in mounting medium (Invitrogen). Immunofluorescence was examined and digital micrographs were taken using a Nikon Eclipse TE2000-E confocal microscope and analyzed using NIS-Elements software (Nikon).

Immunopotentiating Effect of BRM Microparticles.

*Chlamydia abortus.*

*C. abortus* strain B577 (ATCC V-656) was grown in Buffalo Green Monkey Kidney monolayer cell cultures, purified by differential centrifugation, and quantified as previously published (Li et al., 2005). Purified infectious EBs were suspended in sucrose-phosphate-glutamate (SPG) buffer, stored in aliquots at −80° C., and their infectivity was confirmed in female A/J mice.

Animal and BRM Microparticles Administration.

Inbred female C3H/HeJ mice were sourced from the Jackson Laboratory (Bar Harbor, Me.) at 5 weeks of age. Udel "shoebox" type cages with spun fiber filter tops were maintained in static air or ventilated cage racks. Five to ten animals were housed per cage in a temperature-controlled room on a 12-hour light/dark cycle, with ad libitum access to water and standard rodent chow. All animal experiments were approved by the Auburn University Institutional Animal Care and Use Committee (IACUC). Each group was consisted of 10 mice. Mice received the BRM preparation under light isoflurane inhalation anesthesia by intranasal administration of 20 μl or subcutaneous (between the shoulder blades) or intraperitoneal injection of 200 μl of BRM microparticles dissolved in suspension buffer at 6 weeks of age at different time and dosage as required for different experiment set up.

Control Animals.

Mice that received either only PBS (naïve) or microparticles without adjuvant (carrier control) served as controls.

Intranasal *C. abortus* Challenge and Monitoring.

All mice were challenged with $1 \times 10^8$ or $3 \times 10^8$ *C. abortus* elementary bodies suspended in 20 μl sucrose-phosphate-glutamate buffer. In the first experiment for model analysis, all animals were weighed during challenge infection and every second subsequent day until euthanasia on day 10 post challenge. Mice were monitored every day and death, if any, was recorded. Ten days after challenge, mice were sacrificed by $CO_2$ inhalation and weighed. Lungs were collected, weighed, snap frozen in liquid nitrogen, and stored at −80° C. until further processing. Percent lung weight increase was based on naïve lung weights of 134 mg for adult female C3H/HeJ mice. Subsequently, in all experiments mice were monitored daily after challenge, mortality was recorded, and surviving mice were euthanized 21 days after challenge inoculation.

Data Analysis.

All analyses were performed with the Statistica 7.1 software package (StatSoft, Tulsa, Okla.). Results were analyzed by survival analysis, Student's t-test, linear regression, ne-way ANOVA with Tukey's honest significant differences test for correction of the p value in multiple comparisons. P values≤0.05 were considered significant.

REFERENCES

Allahyari M and Mohit E. 2016. Peptide/protein vaccine delivery system based on PLGA particles. *Hum Vaccines Immunother* 12:806-828.

Baldelli A, Powe R M r, Miles R E H, Reid J P, and Vehring R. 2016. Effect of crystallization kinetics on the properties of spray dried microparticles. *Aerosol Sci Technol* 7: 693-704.

Carver K A and Yang D. 2016. N-Acetylcysteine Amide Protects Against Oxidative Stress-Induced Microparticle Release From Human Retinal Pigment Epithelial Cells. *Invest Ophthalmol Vis Sci.* 57:360-371.

Champion J, Walker A, and Mitragotri S. 2008. Role of particle size in phagocytosis of polymeric microspheres. *Pharm Res* 25:1815-1821.

Conte U, Conti B, Giunchedi P, and Maggi L. 1994. Spray dried polylactide microsphere preparation: influence of the technological parameters. *Drug Dev Ind Pharm.* 20:235-258.

Dawes G J S, Fratila-Apachitei L E, Mulia K, Apachitei I, Witkamp G J, and Duszczyk J. 2009. Size effect of PLGA spheres on drug loading efficiency and release profiles. *J Mater Sci Mater Med* 20:1089-1094.

Eldridge J H, Staas J K, Meulbroek J A, Tice T R, and Gilley R M. 1991. Biodegradable and biocompatible poly(DL-lactide-co-glycolide) microspheres as an adjuvant for staphylococcal enterotoxin B toxoid which enhances the level of toxin-neutralizing antibodies. *Infect Immun* 59:2978-2986.

Gander B, Wehrli E, Alder R, and Merkle H P. 1995. Quality improvement of spray-dried protein loaded DL-PLA microspheres by appropriate polymer solvent selection. *J Microencapsul* 12:83-97.

Kamaly N, Yameen B, Wu J, and Farokhzad O C. 2016. Degradable Controlled-Release Polymers and Polymeric Nanoparticles: Mechanisms of Controlling Drug Release. *Chem Rev* 116:2602-63.

Larson MC1, Luthi M R, Hogg N, and Hillery C A. 2013. Calcium-phosphate microprecipitates mimic microparticles when examined with flow cytometry. *Cytometry A* 83:242-250.

Lima K M and Junior J M R. 1999. Poly-DL-lactide-co-glycolide microspheres as a controlled release antigen delivery system. *Braz J Med Biol Res* 32:171-180.

Liu W, Wu W D, Selomulya C, and Chen X D. 2011. Uniform Chitosan Microparticles Prepared by a Novel Spray-Drying Technique. *Int J Chem Eng* 2011: 267218.

McCall R L and Sirianni R W. 2013. PLGA nanoparticles formed by single- or double-emulsion with vitamin E-TPGS. *J Vis Exp* 27:51015.

Nakaoka R, Inoue Y, Tabata Y, and Ikada Y. 1996. Size effect on the antibody production induced by biodegradable microspheres containing antigen. *Vaccine* 14:1251-1256.

O'Hagan DT1, Jeffery H, and Davis S S. 1993. Long-term antibody responses in mice following subcutaneous immunization with ovalbumin entrapped in biodegradable microparticles. *Vaccine* 11:965-969.

Pacheco P, White D, and Sulchek T. 2013. Effects of Microparticle Size and Fc Density on Macrophage Phagocytosis *PLoS One* 8:e60989.

Sameni J, Krigstin S, and Sain M. 2015. Effect of Preparation Parameters on the Formation of Lignin Acetate Microspheres. *Int J Eng Innov Tech* 4: 102-113.

Tabata Y and Ikada Y. 1988. Effect of the size and surface charge of polymer microspheres on their phagocytosis by macrophage. *Biomaterials* 9:356-362.

Tabata Y, Inoue Y, and Ikada Y. 1996. Size effect on systemic and mucosal immune responses induced by oral administration of biodegradable microspheres. *Vaccine* 14:1677-1685.

Tracy M A, Ward K L, Firouzabadian L, Wang Y, Dong N, Qian R, and Zhang Y. 1999. Factors affecting the degradation rate of poly (lactide-co-glycolide) microspheres in vivo and in vitro. *Biomaterials* 20:1057-1062.

Xie H1 and Smith J W. 2010. Fabrication of PLGA nanoparticles with a fluidic nanoprecipitation system. *J Nanobiotechnology* 13:8:18.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for improving feed conversion rate in an animal in need thereof, the method comprising administering orally to the animal a composition comprising biodegradable particles, the biodegradable particles comprising a polymer or a co-polymer comprising polylactide (PLA) and having an effective average diameter of 0.5-5 µm, wherein the animal is administered a dose of the biodegradable particles that is effective for improving feed conversion rate in the animal in comparison to an animal that is not administered the composition.

2. The method of claim 1, wherein the biodegradable particles have an effective average diameter of 0.5-3 µm.

3. The method of claim 1, comprising administering the biodegradable particles to the subject at dose between $(BW/20)^{3/4}$ µg and $100 \times ((BW/20)^{3/4})$ µg, wherein BW is the body weight of the subject in grams.

4. The method of claim 1, wherein the animal is a fowl.

5. The method of claim 4, wherein the fowl is a chicken.

6. The method of claim 5, comprising administering the biodegradable particles to the chicken at dose between $(BW/20)^{3/4}$ µg and $100 \times ((BW/20)^{3/4})$ µg, wherein BW is the body weight of the chicken in grams.

7. The method of claim 5, wherein the chicken is administered a dose of 26.7-270 µg of the biodegradable particles.

8. The method of claim 1, wherein the polymer or the co-polymer further comprises poly(lactic-co-glycolic acid) (PLGA).

9. The method of claim 1, wherein the biodegradable particles are prepared via performing spray-drying of a mixture consisting of (i) the polymer or co-polymer and (ii) a surfactant.

10. The method of claim 9, wherein the surfactant is a co-polymer adjuvant.

11. A method for improving feed conversion rate in a chicken hatchling in need thereof, the method comprising administering orally to the chicken hatchling a composition comprising biodegradable particles, the biodegradable particles comprising a polymer or a co-polymer comprising polylactide (PLA) and having an effective average diameter of 0.5-5 µm, wherein the chicken hatchling is administered a dose of the biodegradable particles that is effective for improving feed conversion rate in the chicken hatchling in comparison to a chicken hatchling that is not administered the composition.

12. The method of claim 11, wherein the polymer or the co-polymer further comprises poly(lactic-co-glycolic acid) (PLGA).

13. The method of claim 11, comprising administering the biodegradable particles to the chicken hatchling at dose between $(BW/20)^{3/4}$ µg and $100 \times ((BW/20)^{3/4})$ µg, wherein BW is the body weight of the chicken hatchling in grams.

14. The method of claim 11, wherein the chicken hatchling is administered a dose of 26.7-270 µg of the biodegradable particles.

15. The method of claim 11, wherein the biodegradable particles are prepared via performing spray-drying of a mixture consisting of (i) the polymer or co-polymer and (ii) a surfactant.

16. The method of claim 15, wherein the surfactant is a co-polymer adjuvant.

17. A method for improving feed conversion rate in a swine in need thereof, the method comprising administering orally to the swine a composition comprising biodegradable particles, the biodegradable particles comprising a polymer or a co-polymer comprising polylactide (PLA) and having an effective average diameter of 0.5-5 µm, wherein the swine is administered a dose of the biodegradable particles that is effective for improving feed conversion rate in the swine in comparison to a swine that is not administered the composition.

18. The method of claim 17, comprising administering the biodegradable particles to the swine at dose between $(BW/20)^{3/4}$ µg and $100 \times ((BW/20)^{3/4})$µg, wherein BW is the body weight of the swine in grams.

19. The method of claim 17, wherein the biodegradable particles are prepared via performing spray-drying of a mixture consisting of (i) the polymer or co-polymer and (ii) a surfactant.

20. The method of claim 19, wherein the surfactant is a co-polymer adjuvant.

\* \* \* \* \*